US008859751B2

(12) United States Patent
Avkin-Nachum et al.

(10) Patent No.: US 8,859,751 B2
(45) Date of Patent: Oct. 14, 2014

(54) OLIGONUCLEOTIDE COMPOUNDS COMPRISING NON-NUCLEOTIDE OVERHANGS

(75) Inventors: Sharon Avkin-Nachum, Nes Zionna (IL); Elena Feinstein, Rehovot (IL)

(73) Assignee: Quark Pharmaceuticals, Inc., Fremont, CA (US)

( * ) Notice: Subject to any disclaimer, the term of this patent is extended or adjusted under 35 U.S.C. 154(b) by 5 days.

(21) Appl. No.: 13/521,033

(22) PCT Filed: Jan. 6, 2011

(86) PCT No.: PCT/US2011/020298
§ 371 (c)(1),
(2), (4) Date: Jul. 6, 2012

(87) PCT Pub. No.: WO2011/085056
PCT Pub. Date: Jul. 14, 2011

(65) Prior Publication Data
US 2013/0035368 A1    Feb. 7, 2013

Related U.S. Application Data

(60) Provisional application No. 61/292,878, filed on Jan. 7, 2010.

(51) Int. Cl.
| | |
|---|---|
| A01N 43/04 | (2006.01) |
| C07H 21/02 | (2006.01) |
| C07H 21/04 | (2006.01) |
| C12P 19/34 | (2006.01) |
| C12Q 1/68 | (2006.01) |

(52) U.S. Cl.
USPC .......... 536/24.5; 435/6; 435/91.1; 435/91.31; 435/455; 514/44; 536/23.1

(58) Field of Classification Search
USPC .......... 435/6.1, 91.1, 91.31, 6, 455; 536/23.1, 536/24.5, 24.31; 514/44
See application file for complete search history.

(56) References Cited

U.S. PATENT DOCUMENTS

| | | | |
|---|---|---|---|
| 5,898,031 | A | 4/1999 | Crooke |
| 5,998,203 | A | 12/1999 | Matulic-Adamic et al. |
| 6,107,094 | A | 8/2000 | Crooke |
| 6,117,657 | A | 9/2000 | Usman et al. |
| 6,235,886 | B1 | 5/2001 | Manoharan et al. |
| 6,251,666 | B1 | 6/2001 | Beigelman |
| 6,506,559 | B1 | 1/2003 | Fire et al. |
| 6,586,238 | B1 | 7/2003 | Matulic-Adamic et al. |
| 6,602,858 | B2 | 8/2003 | Beigelman |
| 7,056,704 | B2 | 6/2006 | Tuschl et al. |
| 7,078,196 | B2 | 7/2006 | Tuschl et al. |
| 7,282,564 | B2 | 10/2007 | Mello et al. |
| 7,452,987 | B2 | 11/2008 | Giese et al. |
| 7,459,547 | B2 | 12/2008 | Zamore et al. |
| 7,582,744 | B2 | 9/2009 | Manoharan et al. |
| 7,595,387 | B2 | 9/2009 | Leake et al. |
| 7,741,299 | B2 | 6/2010 | Feinstein et al. |
| 7,812,002 | B2 | 10/2010 | Feinstein |
| 7,829,693 | B2 | 11/2010 | Kreutzer et al. |
| 7,888,325 | B2 | 2/2011 | Li et al. |
| 7,893,245 | B2 | 2/2011 | Giese et al. |
| 8,084,600 | B2 | 12/2011 | Natt et al. |
| 8,090,542 | B2 | 1/2012 | Khvorova et al. |
| 8,097,710 | B2 | 1/2012 | Baulcombe et al. |
| 8,101,584 | B2 | 1/2012 | Kreutzer et al. |
| 8,202,979 | B2 | 6/2012 | McSwiggen et al. |
| 8,309,704 | B2 | 11/2012 | Zamore et al. |
| 2003/0027783 | A1 | 2/2003 | Zernicka-Goetz et al. |
| 2003/0108923 | A1 | 6/2003 | Tuschl et al. |
| 2003/0166282 | A1 | 9/2003 | Brown et al. |
| 2004/0086884 | A1 | 5/2004 | Beach et al. |
| 2005/0004064 | A1 | 1/2005 | Tei et al. |
| 2005/0020525 | A1 | 1/2005 | McSwiggen et al. |
| 2005/0080246 | A1 | 4/2005 | Allerson et al. |
| 2005/0096289 | A1 | 5/2005 | Prydz et al. |
| 2005/0233342 | A1 | 10/2005 | Manoharan et al. |
| 2005/0255487 | A1 | 11/2005 | Khvorova et al. |
| 2006/0241072 | A1 | 10/2006 | Baker |
| 2007/0032441 | A1 | 2/2007 | McSwiggen et al. |
| 2007/0185047 | A1 | 8/2007 | Bhat et al. |
| 2007/0259827 | A1 | 11/2007 | Aronin et al. |
| 2009/0176725 | A1* | 7/2009 | Morrissey et al. ............. 514/44 |
| 2009/0186410 | A1 | 7/2009 | Aronin et al. |

(Continued)

FOREIGN PATENT DOCUMENTS

| | | |
|---|---|---|
| JP | 2000/290185 | * 10/2000 |
| WO | WO 03/070918 A2 | 8/2003 |

(Continued)

OTHER PUBLICATIONS

Van Aerschot et al., Bull. Soc. Chim. Belf., vol. 104, No. 12, pp. 717-720 (1995).*
Pandolfi et al., Nucleosides & Nucleotides, vol. 18, No. 9, pp. 2051-2069 (1999).*
Koizumi structure appendix (structures provided by the PTO STIC library which were derived from JP 2000/290185), pp. 88-92, 2000.*
Barik (2005). Silence of the transcripts: RNA interference in medicine. *J Mol Med*, 83, 764-773.
Bass (2001). The short answer. *Nature*, 411, 428-429.
Braasch et al. (2003). RNA interference in mammalian cells by chemically-modified RNA. *Biochemistry*, 42, 7967-7975.
Caplen et al. (2001). Specific inhibition of gene expression by small double-stranded RNAs in invertebrate and vertebrate systems. *Proc Natl Acad Sci*, 98(17), 9742-9747.

(Continued)

*Primary Examiner* — Jane Zara
(74) *Attorney, Agent, or Firm* — JMB Davis Ben-David

(57) ABSTRACT

The invention relates to siRNA compounds comprising one non-nucleotide moiety covalently attached to at least one of the sense or antisense strands to down-regulate the expression of human genes. The invention also relates to pharmaceutical compositions comprising such compounds and a pharmaceutically acceptable carrier and to methods of treating and/or preventing the incidence or severity of various diseases or conditions associated with the target genes and/or symptoms associated with such diseases or conditions.

22 Claims, 8 Drawing Sheets

(56) References Cited

U.S. PATENT DOCUMENTS

| | | |
|---|---|---|
| 2009/0209626 A1 | 8/2009 | Khvorova et al. |
| 2010/0292301 A1 | 11/2010 | Feinstein et al. |
| 2011/0112168 A1 | 5/2011 | Feinstein et al. |
| 2011/0178157 A1 | 7/2011 | Jin et al. |
| 2012/0283309 A1 | 11/2012 | Avkin-Nachum |

FOREIGN PATENT DOCUMENTS

| | | |
|---|---|---|
| WO | WO 03/074654 A2 | 9/2003 |
| WO | WO 2007/031877 A2 | 3/2007 |
| WO | WO 2012/078536 A2 | 6/2012 |

OTHER PUBLICATIONS

Chakraborty (2007). Potentiality of small interfering RNAs (siRNA) as recent therapeutic targets for gene-silencing. *Current Drug Targets*, 8(3), 469-482.

Chiu & Rana (2002). RNAi in human cells: basic structural and functional features of small interfering RNA. *Molecular Cell*, 10(3), 549-561.

Chiu & Rana (2003). siRNA function in RNAi: a chemical modification analysis. *RNA*, 9(9), 1034-1048.

Elbashir et al. (2001). RNA interference is mediated by 21- and 22-nucleotide RNAs. *Genes & Development*, 15, 188-200.

Elbashir et al. (2001). Functional anatomy of siRNAs for mediating efficient RNAi in *Drosophila melanogaster* embryo lysate. *EMBO Journal*, 20(23), 6877-6888.

Elbashir et al. (2001). Duplexes of 21-nucleotide RNAs mediate RNA interference in cultured mammalian cells. *Nature*, 411, 494-498.

Elmén et al. (2005). Locked nucleic acid (LNA) mediated improvements in siRNA stability and functionality. *Nucleic Acids Research*, 33(1), 439-447.

Fire et al. (1998). Potent and specific genetic interference by double-stranded RNA in *Caenorhabditis elegans*. *Nature*, 391, 806-811.

Ghosh et al. (2009). Comparing 2-nt 3' overhangs against blunt-ended siRNAs: a systems biology based study. *BMC Genomics*, 10(Suppl 1), S17.

Holen et al. (2002). Positional effects of short interfering RNAs targeting the human coagulation trigger Tissue Factor. *Nucleic Acids Research*, 30(8), 1757-1766.

Mahato et al. (2005). Modulation of gene expression by antisense and antigene oligodeoxynucleotides and small interfering RNA. *Expert Opin. Drug Deliv.*, 2(1), 3-28.

McManus & Sharp (2002). Gene silencing in mammals by small interfering RNAs. *Nature Reviews Genetics*, 3(10), 737-747.

Pandolfi et al. (1999). Evaluation of different types of end-capping modifications on the stability of oligonucleotides toward 3'- and 5'-exonucleases. *Nucleosides & Nucleotides*, 18(9), 2051-2069.

Prakash et al. (2005). Positional effect of chemical modifications on short interference RNA activity in mammalian cells. *J. Med Chem.*, 48(13), 4247-4253.

Scherer & Rossi (2004). Therapeutic applications of RNA interference: recent advances in siRNA Design. *Advances in Genetics*, 52, 1-21.

Schmitz & Chu (2011). Effect of small interfering RNA 3'-end overhangs on chemosensitivity to thymidylate synthase inhibitors. *Silence*, 2(1), 1-10.

Seela & Kaiser (1987). Oligodeoxyribonucleotides containing 1,3-propanediol as nucleoside substitute. *Nucleic Acids Research*, 15(7), 3113-3129.

Sioud & Leirdal (2004). Potential design rules and enzymatic synthesis of siRNAs. *Methods Mol Biol*, 252, 457-468.

Ui-Tei et al. (2006). Essential notes regarding the design of functional siRNAs for efficient mammalian RNAi. *J Biomed Biotechnol*, 2006, 65052.

Ui-Tei et al. (2008). DNA-modified siRNA-dependent gene silencing with reduced off-target effect is induced through a pathway parallel to that for siRNA-mediated RNA interference. Proceedings from *Micro-NanoMechatronics and Human Science*, 2008 (MHS 2008), 339-345.

Ui-Tei et al. (2008). Functional dissection of siRNA sequence by systematic DNA substitution: modified siRNA with a DNA seed arm is a powerful tool for mammalian gene silencing with significantly reduced off-target effect. *Nucleic Acids Research*, 36(7), 2136-2151.

Zamore et al. (2000). RNAi: double-stranded RNA directs the ATP-dependent cleavage of mRNA at 21 to 23 nucleotide intervals. *Cell*, 101, 25-33.

Van Aerschot et al. (1995) Conjugation of Oligonucleotides to 3'-Polar Moieties. Bull. SOC. Chum. Belg. vol. 104, No. 12.

Czauderna et al. (2003). Structural variations and stabilising modifications of synthetic siRNAs in mammalian cells. *Nucleic Acids Research*, 31(11), 2705-2716.

Hamada et al. (2002). Effects of RNA interference in gene expression (RNAi) in cultured mammalian cells of mismatches and the introduction of chemical modifications at the 3'-ends of siRNAs. *Antisense & Nucleic Acid Drug Development*, 12(5), 301-309.

Amarzguioui et al. (2003). Tolerance for mutations and chemical modifications in a siRNA. *Nucleic Acids Research*, 31(2), 589-595.

Dande et al. (2006). Improving RNA interference in mammalian cells by 4'-thio-modified small interfering RNA (siRNA): effect on siRNA activity and nuclease stability when used in combination with 2'-O-alkyl modifications. Journal of Medicinal Chemistry, 49(5), 1624-1634.

International Search Report, mailed Apr. 14, 2011 in connection with PCT International Application No. PCT/US2011/020298, filed Jan. 6, 2011.

* cited by examiner

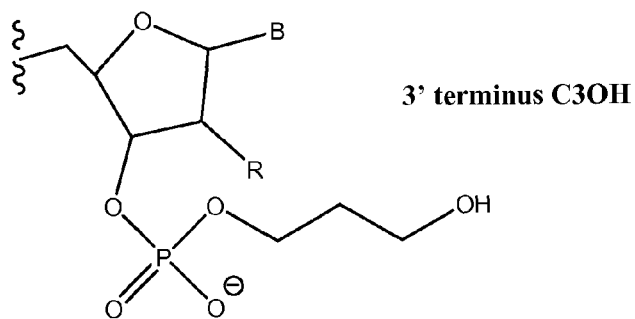
FIG.1A  3' terminus C3OH
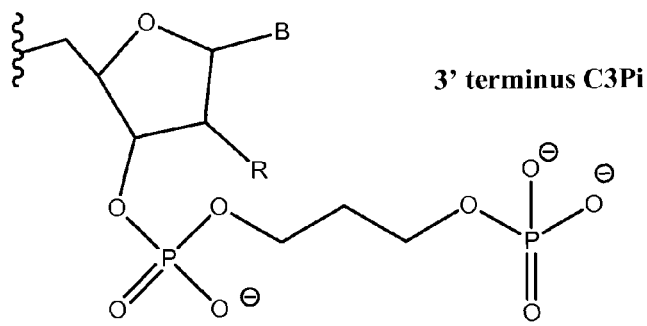
FIG.1B  3' terminus C3Pi
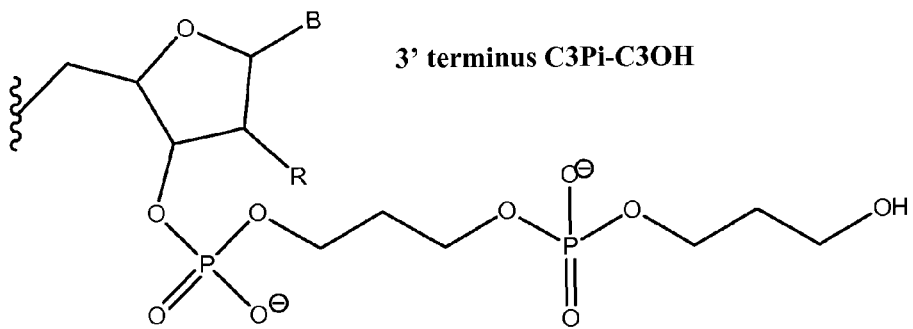
FIG.1C  3' terminus C3Pi-C3OH
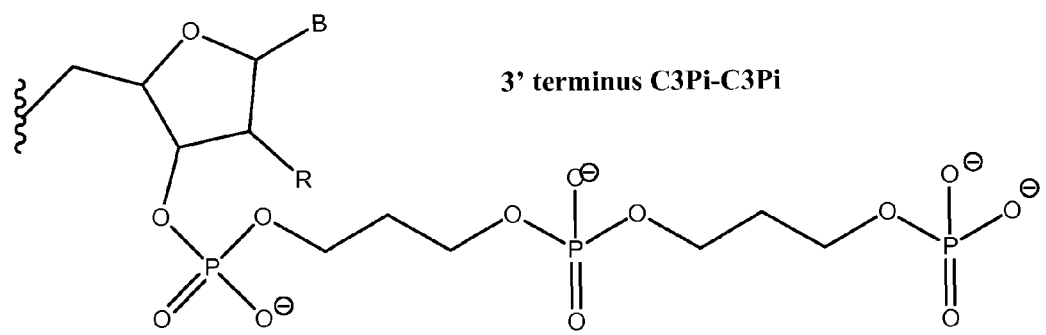
FIG.1D  3' terminus C3Pi-C3Pi

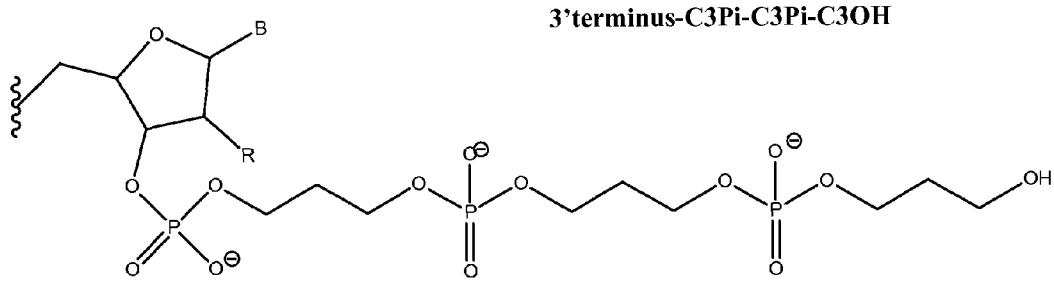
FIG.1E 3'terminus-C3Pi-C3Pi-C3OH
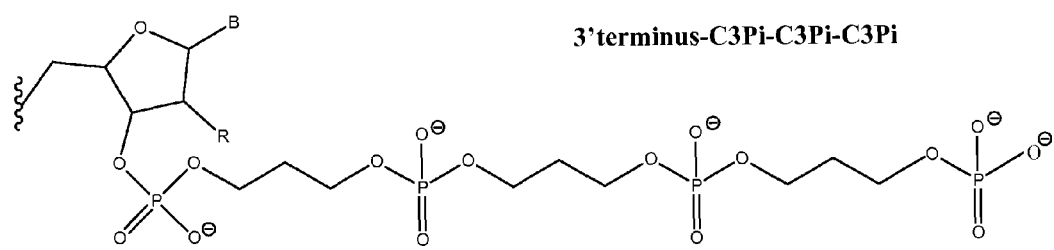
FIG.1F 3'terminus-C3Pi-C3Pi-C3Pi
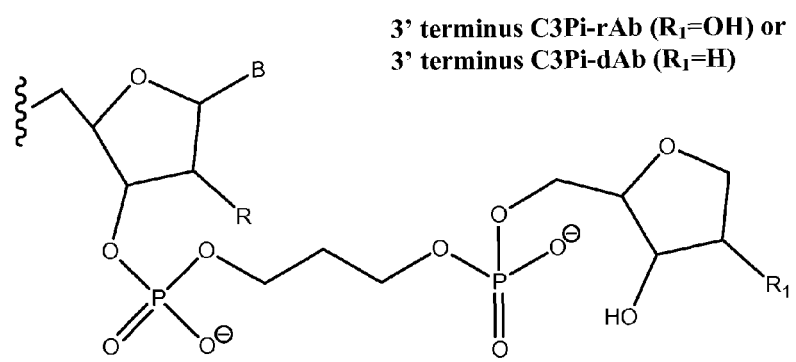
FIG.1G 3' terminus C3Pi-rAb ($R_1$=OH) or 3' terminus C3Pi-dAb ($R_1$=H)

2' terminus C3Pi-C3Pi-C3OH

2' terminus C3Pi-C3Pi-C3OH

OLIGONUCLEOTIDE COMPOUNDS COMPRISING NON-NUCLEOTIDE OVERHANGS

RELATED APPLICATIONS

This application is a §371 national stage of PCT International Application No. PCT/US2011/020298, filed Jan. 6, 2011, claiming priority of PCT International Application No. PCT/US2010/049047, filed Sep. 16, 2010 and the benefit of U.S. Provisional Application No. 61/292,878, filed Jan. 7, 2010, the contents of each of which are hereby incorporated by reference in their entirety.

Throughout this application various patent and scientific publications are cited. The disclosures for these publications in their entireties are hereby incorporated by reference into this application to more fully describe the state of the art to which this invention pertains.

REFERENCE TO SEQUENCE LISTING

This application incorporates-by-reference nucleotide and/or amino acid sequences which are present in the file named "120706_2094_84192_Substitute_Sequence_Listing_GC.txt," which is 5.45 kilobytes in size, and which was created Jul. 5, 2012 in the IBM-PC machine format, having an operating system compatibility with MS-Windows, which is contained in the text file filed Jul. 6, 2012 as part of this application.

FIELD OF THE INVENTION

Disclosed herein are modified double stranded nucleic acid molecules, pharmaceutical compositions comprising same and methods of use thereof for the inhibition of mammalian and non-mammalian target genes. The compounds and compositions are thus useful in the treatment of subjects suffering from diseases or conditions and or symptoms associated with such diseases or conditions in which gene expression has adverse consequences. In particular embodiments the invention provides compositions comprising same and methods of use thereof.

BACKGROUND OF THE INVENTION

RNA interference (RNAi) in mammals is mediated by small interfering RNAs (siRNAs) (Fire et al, Nature 1998, 391:806) or microRNAs (miRNAs) (Ambros, Nature 2004, 431(7006):350-355; Bartel, Cell 2004, 116(2): 281-97). The corresponding process in plants is commonly referred to as specific post-transcriptional gene silencing (PTGS) or RNA silencing and is also referred to as quelling in fungi.

A siRNA is a double-stranded RNA or modified RNA molecule which down-regulates or silences (prevents) the expression of a gene/mRNA of its endogenous (cellular) counterpart. The mechanism of RNA interference is detailed infra.

PCT Publication No. WO 2008/050329 and U.S. Ser. No. 11/978,089 to the assignee of the present invention relate to inhibitors of pro-apoptotic genes, and are incorporated by reference in their entirety. PCT Patent Publication Nos. WO 2008/104978 and WO 2009/044392 to the assignee of the present invention relate to chemically modified siRNA structures, and are incorporated by reference in their entirety.

SUMMARY OF THE INVENTION

The invention provides chemically and or structurally modified siRNA compounds for the inhibition of gene expression in general and of mammalian and prokaryotic genes, in particular. Provided herein are novel structural motifs useful in the preparation of siRNA oligonucleotides comprising one or more non-nucleotide moieties as a 3' (or 2') overhang at the 3'-terminus, compositions comprising same and methods of use thereof. The applicant has determined that the addition of one, and preferably two or three, non-nucleotide moieties to the 3' terminus of a siRNA provides advantageous properties to the siRNA in terms of activity and or stability and or delivery. Accordingly, an existing siRNA can be advantageously modified and future siRNA can be designed and produced to take advantage of this finding. Without wishing to be bound to theory, the nucleic acid molecules disclosed herein and having a 3' non-nucleotide overhang (Z or Z' i.e. C3Pi-C3Ps; C3Pi-C3OH; C3Pi-C3Pi; C3Pi-rAb; C3Pi-dAb) are recognized by the PAZ domain of Argonaute and are able to perform RNAi, while exhibiting good stability and activity.

It will be appreciated that although the term "3' terminus" is used throughout this application to refer to the end of the siRNA strand to which the non-nucleotide moieties are attached, unless explicitly stated otherwise the non-nucleotide moieties, or "overhangs" may be attached at the 3' position of the (deoxy)ribose moiety at the 3'-terminus of the oligonucleotide strand or at the 2' position of the (deoxy)ribose moiety at the 3'-terminus of the oligonucleotide strand, e.g.

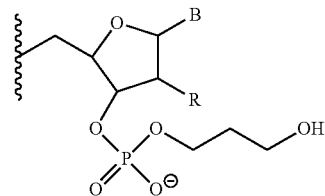

(attachment at the 3' position of the 3'-terminus (deoxy)ribose moiety; in the drawing, B is a nucleotide base and R is H or OH) or

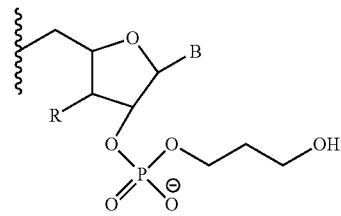

(attachment at the 2' position of the 3'-terminus (deoxy)ribose moiety).

Provided herein are novel structures of double stranded nucleic acid molecules, having advantageous properties and which may be applied to siRNA to any target sequence, comprising non-nucleotide overhangs at one or both 3' termini of the duplex. The chemically modified siRNA modifications disclosed herein are useful in the preparation of stable and active siRNA compounds useful in RNA interference (RNAi).

The application also provides pharmaceutical compositions comprising one or more such oligonucleotides and methods for treating or preventing the incidence or severity of a disease or condition in a subject in need thereof wherein the disease or condition and/or symptoms associated therewith is associated with expression of the target gene. In some embodiments the disease or condition is selected from the group consisting of hearing loss, acute renal failure (ARF), glaucoma, acute respiratory distress syndrome (ARDS) and other acute lung and respiratory injuries, ischemia-reperfusion injury following lung transplantation, ocular ischemic conditions, organ transplantation including lung, liver, heart, pancreas, and kidney transplantation including delayed graft function (DGF), nephro- and neurotoxicity, spinal cord injury, pressure sores, age-related macular degeneration (AMD), dry eye syndrome, oral mucositis, ischemic ocular neuropathy (ION) and chronic obstructive pulmonary disease (COPD). Such methods involve administering to a mammal in need of such treatment a prophylactically or therapeutically effective amount of one or more such compounds, which inhibit or reduce expression or activity of at least one such gene. Such compounds can be administered concurrently or in place of other treatments.

The oligonucleotide is selected to target any mammalian or non-mammalian gene. In various embodiments the modified compound comprises an oligonucleotide sequence set forth in any one of SEQ ID NOS:97-68654 (disclosed in U.S. Ser. No. 11/978,089 and PCT Patent Application No. PCT/IL 2007/001278, which are hereby incorporated by reference in their entirety).

In one aspect a double stranded siRNA compound comprising at least one non-nucleotide 3' terminal overhang is provided. The application provides a synthetic double stranded siRNA compound comprising a sense strand and an antisense strand, wherein at least one of the sense or antisense strands comprises 1, 2, 3, 4, or 5 non-nucleotide moieties, preferably 2 or 3, covalently attached at the 3' terminal end wherein the non-nucleotide moiety is selected from an inverted abasic moiety, an abasic moiety, an alkyl (hydrocarbon) moiety or derivatives thereof, and a phosphate based moiety. In some embodiments the non-nucleotide moiety is selected from an inverted abasic moiety, an alkyl (hydrocarbon) moiety or derivatives thereof and a phosphate based moiety. In some embodiments the non-nucleotide moiety comprises an alkyl (hydrocarbon) moiety or a derivative thereof. Provided herein is a double stranded nucleic acid molecule which includes a sense strand and an antisense strand, wherein at least one strand comprises a non-nucleotide moiety covalently attached at a 3' or a 2' position of the sugar residue at the 3' terminal nucleotide of the strand in which it is present; wherein the non-nucleotide moiety is selected from the group consisting of propanol, a C3 alkyl moiety linked to a phosphodiester, a C3 alkyl moiety linked to a phosphorothioate, a deoxyriboabasic moiety a riboabasic moiety and a combination thereof.

In some embodiments the non-nucleotide moiety is attached to the sugar residue via a phosphate base linkage, preferably a phosphodiester or a phosphorothioate linkage. In some embodiments the non-nucleotide moiety includes a C3 alkyl moiety covalently attached at a 3' or a 2' position of the sugar residue at the 3' terminus of the antisense strand. In various embodiments the C3 alkyl moiety is selected from C3Pi and C3OH.

In some embodiments the molecule includes two or three C3 alkyl moieties covalently linked by a phosphodiester or phosphorothioate linkage or one C3 alkyl moiety covalently linked by a phosphodiester or phosphorothioate linkage to an abasic moiety. In preferred embodiments the molecule includes two C3 alkyl moieties covalently linked by a phosphodiester or phosphorothioate linkage.

In some embodiments the C3 alkyl moieties are selected from C3Pi-C3OH, C3Pi-C3Pi, C3Pi-C3Ps, C3Pi-C3Pi-C3OH, C3Ps-C3Ps-C3OH, C3Pi-C3Ps-C3OH, C3Ps-C3Pi-C3OH, C3Pi-C3Pi-C3Pi, C3Ps-C3Ps-C3Ps, C3Pi-C3Ps-C3Ps, C3Ps-C3Pi-C3Ps, C3Ps-C3Ps-C3Pi, C3Pi-C3Pi-C3Ps, C3Ps-C3Pi-C3Pi or C3Pi-C3Ps-C3Pi moieties.

In other embodiments the molecule includes a C3 alkyl moiety covalently linked by a phosphodiester or phosphorothioate linkage to an abasic moiety wherein the abasic moiety is selected from a deoxyriboabasic moiety or a riboabasic moiety. In some embodiments the C3 alkyl moiety covalently linked by a phosphodiester or phosphorothioate linkage to an abasic moiety is selected from C3Pi-rAb, C3Pi-dAb, rAb-C3OH, rAb-C3Pi, dAb-C3OH, or dAb-C3Pi.

In some embodiments, provided are double stranded nucleic acid molecules having the structure (A1):

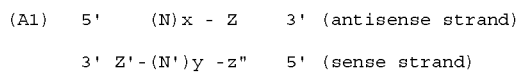

wherein each of N and N' is a nucleotide which may be unmodified or modified, or an unconventional moiety;
wherein each of (N)x and (N')y is an oligonucleotide in which each consecutive N or N' is joined to the next N or N' by a covalent bond;
wherein at least one of Z or Z' is present and comprises a non-nucleotide moiety covalently attached at the 3' terminus of the strand in which it is present;
wherein z" may be present or absent, but if present is a capping moiety covalently attached at the 5' terminus of (N') y;
wherein each of x and y is independently an integer between 18 and 40;
wherein the sequence of (N')y has complementarity to the sequence of (N)x; and wherein the sequence of (N)x has complementarity to a consecutive sequence in a target RNA.

In some embodiments the covalent bond joining each consecutive N or N' is a phosphodiester bond.

In some embodiments x=y=19 to 27, for example 19, 20, 21, 22, 23, 24, 25, 26, 27. In some embodiments x=y and each of x and y is 19, 20, 21, 22 or 23. In various embodiments x=y=19.

In some embodiments x=y=19 and one of Z or Z' is present and consists of two non-nucleotide moieties.

In some embodiments x=y=19 and Z' is present and consists of two non-nucleotide moieties.

In preferred embodiments x=y=19 and Z is present and consists two non-nucleotide moieties.

In preferred embodiments x=y=19 and Z is present and consists of two non-nucleotide moieties; and Z' is present and consists of one non-nucleotide moiety.

In additional embodiments x=y=19 and Z and Z' are present and each independently comprises two non-nucleotide moieties.

In some embodiments the double stranded nucleic acid molecules comprise a DNA moiety or a mismatch to the target at position 1 of the antisense strand (5' terminus). Such a structure is described herein. According to one embodiment provided are double stranded nucleic acid molecules having a structure (A2) set forth below:

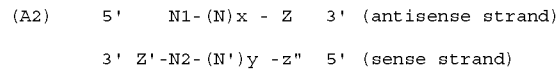

wherein each of N2, N and N' is an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y has complementarity to the sequence of (N)x and (N)x has complementarity to a consecutive sequence in a target RNA;

wherein N1 is covalently bound to (N)x and is mismatched to the target RNA or is a complementary DNA moiety to the target RNA;

wherein N1 is a moiety selected from the group consisting of natural or modified uridine, deoxyribouridine, ribothymidine, deoxyribothymidine, adenosine or deoxyadenosine;

wherein z" may be present or absent, but if present is a capping moiety covalently attached at the 5' terminus of N2-(N')y; and wherein at least one of Z or Z' is present and comprises a non-nucleotide moiety covalently attached at the 3' terminus of the strand in which it is present.

In some embodiments x=y=18 and one of Z or Z' is present and consists of two non-nucleotide moieties.

In some embodiments x=y=18 and Z' is present and consists of two non-nucleotide moieties.

In preferred embodiments x=y=18 and Z is present and consists two non-nucleotide moieties.

In preferred embodiments x=y=18 and Z is present and consists of two non-nucleotide moieties; and Z' is present and consists of one non-nucleotide moiety.

In additional embodiments x=y=18 and Z and Z' are present and each independently comprises two non-nucleotide moieties.

In some embodiments the sequence of (N')y is fully complementary to the sequence of (N)x. In various embodiments sequence of N2-(N')y is complementary to the sequence of N1-(N)x. In some embodiments (N)x comprises an antisense that is fully complementary to about 17 to about 39 consecutive nucleotides in a target RNA. In other embodiments (N)x comprises an antisense that is substantially complementary to about 17 to about 39 consecutive nucleotides in a target RNA.

In some embodiments N1 and N2 form a Watson-Crick base pair. In some embodiments N1 and N2 form a non-Watson-Crick base pair. In some embodiments a base pair is formed between a ribonucleotide and a deoxyribonucleotide.

In some embodiments x=y=18, x=y=19 or x=y=20. In preferred embodiments x=y=18. When x=18 in N1-(N)x, N1 refers to position 1 and positions 2-19 are included in (N)18 When y=18 in N2-(N')y N2, refers to position 19 and positions 1-18 are included in (N')18

In some embodiments N1 is covalently bound to (N)x and is mismatched to the target RNA. In various embodiments N1 is covalently bound to (N)x and is a DNA moiety complementary to the target RNA.

In some embodiments N1 and N2 form a base pair between uridine or deoxyuridine and adenosine or deoxyadenosine (rU-rA, rU-dA, dU-rA, dU-dA). In other embodiments N1 and N2 form a base pair between deoxyuridine and adenosine.

In some embodiments the double stranded nucleic acid molecule is a siRNA, siNA or a miRNA. The double stranded nucleic acid molecules as provided herein are also referred to as "duplexes".

In certain preferred embodiments x=y=18. In some embodiments N1 and N2 form a Watson-Crick base pair. In other embodiments N1 and N2 form a non-Watson-Crick base pair. In certain embodiments N1 is selected from the group consisting of riboadenosine, modified riboadenosine, deoxyriboadenosine, modified deoxyriboadenosine. In other embodiments N1 is selected from the group consisting of ribouridine, deoxyribouridine, modified ribouridine, and modified deoxyribouridine.

In some embodiments each of N and N' is an unmodified nucleotide. In some embodiments at least one of N or N' includes a chemically modified nucleotide or an unconventional moiety. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments at least one of N or N' includes a 2'OMe sugar-modified ribonucleotide.

In some embodiments the sequence of (N')y is fully complementary to the sequence of (N)x. In other embodiments the sequence of (N')y is substantially complementary to the sequence of (N)x.

In some embodiments (N)x includes an antisense sequence that is fully complementary to about 17 to about 39 consecutive nucleotides in a target RNA. In other embodiments (N)x includes an antisense that is substantially complementary to about 17 to about 39 consecutive nucleotides in a target RNA.

In some embodiments the nucleic acid molecules disclosed herein are siRNA, siNA or miRNA.

In some embodiments of Structures A1 and A2, Z is present and Z' is absent. In other embodiments Z' is present and Z is absent. In additional embodiments both Z and Z' are present. In some embodiments Z and Z' are present and are identical. In further embodiments Z and Z' are present and are different. In some embodiments Z and Z' are independently 2, 3, 4 or 5 non-nucleotide moieties or a combination of 2, 3, 4, or 5 non-nucleotide moieties and nucleotides. In some embodiments each of Z and or Z' consist of two (2) non-nucleotide moieties covalently attached to the 3' terminus of the siRNA strand via a phosphodiester bond.

A non-nucleotide moiety is selected from the group consisting of an abasic moiety, an inverted abasic moiety, an alkyl moiety or derivative thereof, and an inorganic phosphate. In some embodiments a non-nucleotide moiety is an alkyl moiety or derivative thereof. In some embodiments the alkyl moiety comprises a terminal functional group selected from the group consisting of an alcohol, a terminal amine, a terminal phosphate and a terminal phosphorothioate moiety.

In some embodiments Z is present and comprises one or more non-nucleotide moieties selected from the group consisting of an abasic moiety, an inverted abasic moiety, hydrocarbon moiety or derivative thereof, and an inorganic phosphate. In some embodiments Z is present and consists of two alkyl moieties or derivatives thereof.

In additional embodiments Z' is present and comprises one or more non-nucleotide moieties selected from the group consisting of an abasic moiety, an inverted abasic moiety, a hydrocarbon moiety, and an inorganic phosphate. In some embodiments Z' is present and comprises one or more alkyl moieties or derivatives thereof.

In some embodiments Z is present and consists of two alkyl moieties or derivatives thereof and Z' is present and consists of a single alkyl moiety or derivative thereof.

In some embodiments each of Z and Z' includes an abasic moiety, for example a deoxyriboabasic moiety (referred to herein as "dAb") or riboabasic moiety (referred to herein as "rAb"). In some embodiments each of Z and/or Z' comprises two covalently linked abasic moieties and is for example 5'>3' dAb-dAb or rAb-rAb or dAb-rAb or rAb-dAb. Each moiety is covalently conjugated to an adjacent moiety via a covalent bond, preferably a phospho-based bond. In some embodiments the phospho-based bond is a phosphorothioate, a phosphonoacetate or a phosphodiester bond.

In some embodiments each of Z and/or Z' independently includes a C2, C3, C4, C5 or C6 alkyl moiety, optionally a C3 [propane, —(CH2)$_3$—] moiety or a derivative thereof e.g. propanol (C3-OH), propanediol, or phosphodiester derivative of propanediol ("C3Pi"). In preferred embodiments each of Z and/or Z' includes two hydrocarbon moieties and in some examples is C3-C3. Each C3 is covalently conjugated to an adjacent C3 via a covalent bond, preferably a phospho-based bond. In some embodiments the phospho-based bond is a phosphorothioate, a phosphonoacetate or a phosphodiester bond.

In some embodiments of Structure A1 and Structure A2 at least one of Z or Z' is present and comprises at least two non-nucleotide moieties covalently attached to the strand in which it is present. In some embodiments each of Z and Z' independently includes a C3 alkyl, C3 alcohol or C3 ester moiety. In some embodiments Z' is absent and Z is present and includes a non-nucleotide C3 moiety. In some embodiments Z is absent and Z' is present and includes a non-nucleotide C3 moiety.

In some embodiments of Structures A1 and A2, each of N and N' is an unmodified nucleotide. In some embodiments at least one of N or N' includes a chemically modified nucleotide or an unconventional moiety. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments at least one of N or N' includes a 2'OMe sugar-modified ribonucleotide.

In some embodiments the sequence of (N')y is fully complementary to the sequence of (N)x. In other embodiments the sequence of (N')y is substantially complementary to the sequence of (N)x.

In other embodiments the compound of Structure A1 or Structure A2 includes at least one ribonucleotide modified in the sugar residue. In some embodiments the compound includes a modification at the 2' position of the sugar residue. In some embodiments the modification in the 2' position includes the presence of an amino, a fluoro, an alkoxy or an alkyl moiety. In certain embodiments the 2' modification includes an alkoxy moiety, In preferred embodiments the alkoxy moiety is a methoxy moiety (also known as 2'-O-methyl; 2'OMe; 2'-OCH3). In some embodiments the nucleic acid compound includes 2' OMe sugar modified alternating ribonucleotides in one or both of the antisense and the sense strands. In other embodiments the compound includes 2'OMe sugar modified ribonucleotides in the antisense strand, (N)x or N1-(N)x, only. In certain embodiments the middle ribonucleotide of the antisense strand; e.g. ribonucleotide in position 10 in a 19-mer strand is unmodified. In various embodiments the nucleic acid compound includes at least 5 alternating 2'OMe sugar modified and unmodified ribonucleotides. In additional embodiments the compound of Structure A1 or Structure A2 includes modified ribonucleotides in alternating positions wherein each ribonucleotide at the 5' and 3' termini of (N)x or N1-(N)x are modified in their sugar residues, and each ribonucleotide at the 5' and 3' termini of (N')y or N2-(N)y are unmodified in their sugar residues.

In some embodiments the double stranded molecule includes one or more of the following modifications
a) N in at least one of positions 5, 6, 7, 8, or 9 from the 5' terminus of the antisense strand is selected from a 2'5' nucleotide or a mirror nucleotide;

b) N' in at least one of positions 9 or 10 from the 5' terminus of the sense strand is selected from a 2'5' nucleotide and a pseudoUridine; and
c) N' in 4, 5, or 6 consecutive positions at the 3' terminus positions of (N')y comprises a 2'5' nucleotide.

In some embodiments the double stranded molecule includes a combination of the following modifications
a) the antisense strand includes a 2'5' nucleotide or a mirror nucleotide in at least one of positions 5, 6, 7, 8, or 9 from the 5' terminus; and
b) the sense strand includes at least one of a 2'5' nucleotide and a pseudoUridine in positions 9 or 10 from the 5' terminus.

In some embodiments the double stranded molecule includes a combination of the following modifications
a) the antisense strand includes a 2'5' nucleotide or a mirror nucleotide in at least one of positions 5, 6, 7, 8, or 9 from the 5' terminus; and
c) the sense strand includes 4, 5, or 6 consecutive 2'5' nucleotides at the 3' penultimate or 3' terminal positions.

In some embodiments, the sense strand [(N)x or N1-(N)x] includes 1, 2, 3, 4, 5, 6, 7, 8, or 9 2'OMe sugar modified ribonucleotides. In some embodiments, the antisense strand includes 2'OMe modified ribonucleotides at positions 2, 4, 6, 8, 11, 13, 15, 17 and 19. In other embodiments antisense strand includes 2'OMe modified ribonucleotides at positions 1, 3, 5, 7, 9, 11, 13, 15, 17 and 19. In other embodiments the antisense strand includes 2'OMe modified ribonucleotides at positions 3, 5, 7, 9, 11, 13, 15, 17 and 19. In some embodiments the antisense strand includes one or more 2'OMe sugar modified pyrimidines. In some embodiments all the pyrimidine nucleotides in the antisense strand are 2'OMe sugar modified. In some embodiments the sense strand includes 2'OMe sugar modified pyrimidines.

In some embodiments of Structure A1 and Structure A2, the sense strand and the antisense strand are independently phosphorylated or unphosphorylated at the 3' terminus and at the 5' terminus. In some embodiments of Structure A1 and Structure A2, the sense strand and the antisense strand are unphosphorylated at the 3' and 5' termini. In other embodiments the sense strand and the antisense strand are phosphorylated at the 3' termini.

In some embodiments of Structure A1 and Structure A2 (N)y includes at least one unconventional moiety selected from a mirror nucleotide, a 2'5' nucleotide and a TNA. In some embodiments the unconventional moiety is a mirror nucleotide. In various embodiments the mirror nucleotide is selected from an L-ribonucleotide (L-RNA) and an L-deoxyribonucleotide (L-DNA). In preferred embodiments the mirror nucleotide is L-DNA. In certain embodiments the sense strand comprises an unconventional moiety in position 9 or 10 (from the 5' terminus). In preferred embodiments the sense strand includes an unconventional moiety in position 9 (from the 5' terminus). In some embodiments the sense strand is 19 nucleotides in length and comprises 4, 5, or 6 consecutive unconventional moieties in positions 15, (from the 5' terminus). In some embodiments the sense strand includes 4 consecutive 2'5' ribonucleotides in positions 15, 16, 17, and 18. In some embodiments the sense strand includes 5 consecutive 2'5' ribonucleotides in positions 15, 16, 17, 18 and 19. In various embodiments the sense strand further comprises Z'. In some embodiments Z' includes a C3OH moiety or a C3Pi moiety.

In some embodiments of Structure A1 (N')y includes at least one L-DNA moiety. In some embodiments x=y=19 and (N')y, consists of unmodified ribonucleotides at positions 1-17 and 19 and one L-DNA at the 3' penultimate position (position 18). In other embodiments x=y=19 and (N')y consists of unmodified ribonucleotides at positions 1-16 and 19 and two consecutive L-DNA at the 3' penultimate position (positions 17 and 18). In various embodiments the unconventional moiety is a nucleotide joined to an adjacent nucleotide by a 2'-5' internucleotide phosphate linkage. According to various embodiments (N')y includes 2, 3, 4, 5, or 6 consecutive ribonucleotides at the 3' terminus linked by 2'-5' internucleotide linkages. In one embodiment, four consecutive nucleotides at the 3' terminus of (N')y are joined by three 2'-5' phosphodiester bonds, wherein one or more of the 2'-5' nucleotides which form the 2'-5' phosphodiester bonds further includes a 3'-O-methyl (3'OMe) sugar modification. Preferably the 3' terminal nucleotide of (N')y includes a 2'OMe sugar modification. In certain embodiments x=y=19 and (N')y includes two or more consecutive nucleotides at positions 15, 16, 17, 18 and 19 include a nucleotide joined to an adjacent nucleotide by a 2'-5' internucleotide bond (2'-5' nucleotide). In various embodiments the nucleotide forming the 2'-5' internucleotide bond includes a 3' deoxyribose nucleotide or a 3' methoxy nucleotide (3' H or 3'OMe in place of a 3' OH). In some embodiments x=y=19 and (N')y includes 2'-5' nucleotides at positions 15, 16 and 17 such that adjacent nucleotides are linked by a 2'-5' internucleotide bond between positions 15-16, 16-17 and 17-18; or at positions, 15, 16, 17, 18, and 19 such that adjacent nucleotides are linked by a 2'-5' internucleotide bond between positions 15-16, 16-17, 17-18 and 18-19 and a 3'OH is available at the 3' terminal nucleotide or at positions 16, 17 and 18 such that adjacent nucleotides are linked by a 2'-5' internucleotide bond between positions 16-17, 17-18 and 18-19. In some embodiments x=y=19 and (N')y includes 2'-5' nucleotides at positions 16 and 17 or at positions 17 and 18 or at positions 15 and 17 such that adjacent nucleotides are linked by a 2'-5' internucleotide bond between positions 16-17 and 17-18 or between positions 17-18 and 18-19 or between positions 15-16 and 17-18, respectively. In other embodiments the pyrimidine ribonucleotides (rU, rC) in (N')y are substituted with nucleotides joined to the adjacent nucleotide by a 2'-5' internucleotide bond. In some embodiments x=y=19 and (N')y comprises five consecutive nucleotides at the 3' terminus joined by four 2'-5' linkages, specifically the linkages between the nucleotides position 15-16, 16-17, 17-18 and 18-19.

In some embodiments x=y=19 and (N')y comprises five consecutive nucleotides at the 3' terminus joined by four 2'-5' linkages and optionally further includes Z' and z' independently selected from an inverted abasic moiety and a C3 alkyl [C3; 1,3-propanediol mono(dihydrogen phosphate)] cap. The C3 alkyl cap is covalently linked to the 3' or 5' terminal nucleotide. In some embodiments the 3' C3 terminal cap further comprises a 3' phosphate. In some embodiments the 3' C3 terminal cap further comprises a 3' terminal hydroxyl group.

In some embodiments x=y=19 and (N')y comprises an L-DNA position 18; and (N')y optionally further includes Z' and z' independently selected from an inverted abasic moiety and a C3 alkyl [C3; 1,3-propanediol mono(dihydrogen phosphate)] cap.

In some embodiments (N')y comprises a 3' terminal phosphate (i.e. phosphorylated at the 3' terminus). In some embodiments (N')y comprises a 3' terminal hydroxyl.

In some embodiments x=y=19 and (N)x includes 2'OMe sugar modified ribonucleotides at positions 1, 3, 5, 7, 9, 11, 13, 15, 17, 19 or at positions 2, 4, 6, 8, 11, 13, 15, 17, 19. In some embodiments x=y=19 and (N)x includes 2'OMe sugar modified pyrimidines. In some embodiments all pyrimidines in (N)x include the 2'OMe sugar modification.

In some embodiments of structure A2 x=y=18 and N2 is a riboadenosine moiety. In some embodiments x=y=18, and N2-(N')y comprises five consecutive nucleotides at the 3' terminus joined by four 2'-5' linkages, specifically the linkages between the nucleotides position 15-16, 16-17, 17-18 and 18-19. In some embodiments the linkages include phosphodiester bonds. In some embodiments x=y=18 and N2-(N')y comprises five consecutive nucleotides at the 3' terminus joined by four 2'-5' linkages and optionally further includes Z' and z' independently selected from an inverted abasic moiety and a C3 alkyl [C3; 1,3-propanediol mono (dihydrogen phosphate)] cap. In some embodiments x=y=18 and N2-(N')y comprises an L-DNA position 18; and (N')y optionally further includes Z' and z' independently selected from an inverted abasic moiety and a C3 alkyl [C3; 1,3-propanediol mono(dihydrogen phosphate)] cap. In some embodiments N2-(N')y comprises a 3' terminal phosphate. In some embodiments N2-(N')y comprises a 3' terminal hydroxyl. In some embodiments x=y=18 and N1-(N)x includes 2'OMe sugar modified ribonucleotides in positions 1, 3, 5, 7, 9, 11, 13, 15, 17, 19 or in positions 1, 3, 5, 9, 11, 13, 15, 17, 19, or in positions 3, 5, 9, 11, 13, 15, 17, or in positions 2, 4, 6, 8, 11, 13, 15, 17, 19. In some embodiments x=y=18 and N1-(N)x includes 2'OMe sugar modified ribonucleotides at positions 11, 13, 15, 17 and 19 (from 5' terminus). In some embodiments x=y=18 and N1-(N)x includes 2'OMe sugar modified ribonucleotides in positions 1, 3, 5, 7, 9, 11, 13, 15, 17, 19 or in positions 3, 5, 7, 9, 11, 13, 15, 17, 19. In some embodiments x=y=18 and N1-(N)x includes 2'OMe sugar modified ribonucleotides in positions 2, 4, 6, 8, 11, 13, 15, 17, 19.

In some embodiments x=y=18 and N1-(N)x includes 2'OMe sugar modified pyrimidines. In some embodiments all pyrimidines in (N)x include the 2'OMe sugar modification. In some embodiments the antisense strand further comprises an L-DNA or a 2'-5' nucleotide in position 5, 6 or 7 (5'>3'). In other embodiments the antisense strand further comprises a ribonucleotide, which generates a 2'5' internucleotide linkage in between the ribonucleotides in positions 5-6 or 6-7 (5'>3').

In additional embodiments N1-(N)x further includes Z wherein Z comprises a non-nucleotide overhang. In some embodiments the non-nucleotide overhang is C3-C3 [1,3-propanediol mono(dihydrogen phosphate)]2.

In some embodiments of Structure A2, (N)y includes at least one L-DNA moiety. In some embodiments x=y=18 and (N')y consists of unmodified ribonucleotides at positions 1-16 and 18 and one L-DNA at the 3' penultimate position (position 17). In other embodiments x=y=18 and (N')y consists of unmodified ribonucleotides at position 1-15 and 18 and two consecutive L-DNA at the 3' penultimate position (positions 16 and 17). In various embodiments the unconventional moiety is a nucleotide joined to an adjacent nucleotide by a 2'-5' internucleotide phosphate linkage. According to various embodiments (N')y includes 2, 3, 4, 5, or 6 consecutive ribonucleotides at the 3' terminus linked by 2'-5' internucleotide linkages. In one embodiment, four consecutive nucleotides at the 3' terminus of (N')y are joined by three 2'-5' phosphodiester bonds, wherein one or more of the 2'-5' nucleotides which form the 2'-5' phosphodiester bonds further includes a 3'-O-methyl (3'OMe) sugar modification. Preferably the 3' terminal nucleotide of (N')y includes a 2'OMe sugar modification. In certain embodiments x=y=18 and in (N')y two or more consecutive nucleotides at positions 14, 15, 16, 17, and 18 include a nucleotide joined to an adjacent nucleotide by a 2'-5' internucleotide bond. In various embodiments the nucleotide forming the 2'-5' internucleotide bond includes a 3' deoxyribose nucleotide or a 3' methoxy nucleotide. In some embodiments x=y=18 and (N')y includes nucleotides joined to the adjacent nucleotide by a 2'-5' internucleotide bond between positions 15-16, 16-17 and 17-18 or between positions 16-17 and 17-18. In some embodiments x=y=18 and (N')y includes nucleotides joined to the adjacent nucleotide by a 2'-5' internucleotide bond between positions 14-15, 15-16, 16-17, and 17-18 or between positions 15-16, 16-17, and 17-18 or between positions 16-17 and 17-18 or between positions 17-18 or between positions 15-16 and 17-18. In other embodiments the pyrimidine ribonucleotides (rU, rC) in (N')y are substituted with nucleotides joined to the adjacent nucleotide by a 2'-5' internucleotide bond.

The C3 alkyl moiety may be covalently linked to the 3' terminus of (N')y and/or the 3' terminus of (N)x via a phosphodiester bond. In some embodiments the alkyl moiety comprises propanol, propyl phosphate or propyl phosphorothioate. In some embodiments each of Z and Z' is independently selected from propanol, propyl phosphate, propyl phosphorothioate combinations thereof or multiples thereof in particular 2 or 3 covalently linked propanol, propyl phosphate, propyl phosphorothioate or combinations thereof.

In some embodiments each of Z and Z' is independently selected from propyl phosphate, propyl phosphorothioate, propyl phospho-propanol; propyl phospho-propyl phosphorothioate; propylphospho-propyl phosphate; (propyl phosphate)$_3$, (propyl phosphate)-2-propanol, (propyl phosphate)$_2$-propyl phosphorothioate. Any propane or propanol conjugated moiety can be included in Z or Z'.

In additional embodiments each of Z and/or Z' comprises a combination of an abasic moiety and an unmodified deoxyribonucleotide or ribonucleotide or a combination of a hydrocarbon moiety and an unmodified deoxyribonucleotide or ribonucleotide or a combination of an abasic moiety (deoxyribo or ribo) and a hydrocarbon moiety. In such embodiments, each of Z and/or Z' comprises C3Pi-rAb, C3Ps-rAb, C3Ps-dAb or C3Pi-dAb.

According to certain embodiments the invention provides an siRNA compound further comprising one or more modified ribonucleotide or unconventional moiety, wherein the modified nucleotide possesses a modification in the sugar moiety, in the base moiety or in the internucleotide linkage moiety. In some embodiments one or more of N or N' comprises a 2'OMe modified ribonucleotide, a 2'5' or an L-nucleotide.

In some embodiments (N)x comprises modified and unmodified ribonucleotides, each modified ribonucleotide having a 2'-O-methyl on its sugar (2'OMe modified or 2'OMe sugar modified), wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide.

In some embodiments at least one of $(N)_x$ and $(N')_y$ comprises at least one mirror nucleotide. In some embodiments in (N')y at least one unconventional moiety is present, which unconventional moiety is selected from an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond. In some embodiments at least one of N' is a mirror nucleotide.

In some embodiments the unconventional moiety is an L-DNA mirror nucleotide. In additional embodiments x=y=19 and at least one unconventional moiety is present at one of positions 15, 16, 17, or 18 in (N')y. In some embodiments the unconventional moiety is a mirror nucleotide, preferably an L-DNA moiety. In some embodiments the L-DNA moiety is present at position 17, position 18 or positions 17 and 18.

In some embodiments the unconventional moiety is a nucleotide joined to an adjacent nucleotide by a 2'-5' internucleotide phosphate bond. In additional embodiments x=y=19 and the nucleotides at positions 15-19 or 16-19 or 17-19 in (N')y are joined to adjacent nucleotides by 2'-5' internucleotide phosphate bonds. In some embodiments x=y=19 and the nucleotides at positions 15-19 or 16-19 or 17-19 or 15-18 or 16-18 in (N')y are joined to the adjacent nucleotides by 2'-5' internucleotide phosphate bonds.

In some embodiments (N)x comprises nine alternating modified ribonucleotides. In other embodiments (N)x comprises nine alternating modified ribonucleotides further comprising a 2'OMe modified nucleotide at position 2. In some embodiments x=19 and (N)x comprises 2'OMe modified ribonucleotides at the odd numbered positions 1, 3, 5, 7, 9, 11, 13, 15, 17, 19. In other embodiments (N)x further comprises a 2'OMe modified ribonucleotide at one or both of positions 2 and 18. In yet other embodiments (N)x comprises 2'OMe modified ribonucleotides at positions 2, 4, 6, 8, 11, 13, 15, 17, 19. In some embodiments at least one pyrimidine nucleotide in (N)x comprises a 2'OMe sugar modification. In some embodiments all pyrimidine nucleotides in (N)x comprises a 2'OMe sugar modification. In some embodiments 2, 3, 4, 5, 6, 7, 8, 9, 1'0, 11, 12, 13, 14, or 15 pyrimidine nucleotides in N(x) comprise a 2'OMe sugar modification In various embodiments z" is present and is selected from an abasic ribose moiety, an abasic deoxyribose moiety, a deoxyribose moiety; an inverted abasic ribose moiety; a C3 moiety, C6-amino-Pi; a mirror nucleotide.

In certain embodiments (N)x is fully complementary to a target sequence. In other embodiments (N)x is substantially complementary to a target sequence. In some embodiments (N)x comprises one mismatch to the target sequence. In preferred embodiments (N)x comprises a one-nucleotide mismatch to the target sequence at the 5' terminus of (N)x; i.e. position 1.

In certain embodiments (N)x and (N')y are fully complementary. In other embodiments (N)x and (N')y are substantially complementary.

In some embodiments (N)x comprises one mismatch to the target sequence at position 1 and (N)x and (N')y are fully complementary. In some embodiments (N)x comprises one nucleotide mismatch to the target sequence at position 1 and (N')y comprises one nucleotide mismatch to (N)x at position 1.

In some embodiments x=y=19 and in (N)x eighteen consecutive nucleotides at positions 2-19 are complementary to eighteen consecutive nucleotides in the target RNA and the nucleotide at position 1 is mismatched to the target RNA sequence. In various embodiments the nucleotide at position 1 in (N)x is substituted with a moiety selected from the group consisting of ribouracil, modified ribouracil, deoxyribouracil, modified deoxyribouracil, pseudouracil, deoxypseudouracil, deoxyribothymidine, modified deoxyribothymidine, ribocytosine, modified ribocytosine, deoxyribocytosine, modified deoxyribocytosine, an abasic ribose moiety and an abasic deoxyribose moiety. In some embodiments the nucleotide at position 1 in (N)x is substituted with a moiety selected from the group consisting of ribouracil, modified ribouracil, deoxyribouracil, modified deoxyribouracil.

In some embodiments x=y=19 and in (N)x 18 consecutive nucleotides at positions 2-19 are complementary to 18 consecutive nucleotides in the target RNA and the nucleotide at position 1 is mismatched to the target RNA sequence and the nucleotide at position 19 of (N')y is complementary to the nucleotide at position 1 of (N)x. In other embodiments x=y=19 and the nucleotide at position 1 of (N)x is mismatched to the target mRNA sequence and the nucleotide at position 19 of (N')y is mismatched to the nucleotide at position 1 of (N)x.

The double stranded nucleic acid molecules disclosed herein are advantageous in that they exhibit improved stability and/or improved activity and/or reduced off target effects and/or reduced immune response and/or enhanced uptake by cells when compared to blunt ended, or molecules with 3' dTdT.

Other embodiments are envisaged wherein x=y=21 or wherein x=y=23. Structure (A1) and (A(2) are useful with known and future oligonucleotide pairs (sense and antisense strands) to a mammalian or non-mammalian (e.g. viral, bacterial, plant) gene. In some embodiments the mammalian gene is a human gene. In various embodiments the mRNA of the human gene is set forth in PCT Patent Publication No. WO 2009/044392. In additional embodiments the oligonucleotide pair is set forth in PCT Patent Publication No. WO 2009/044392. In further embodiments Structures (A1) or (A2) further comprise modifications and motifs set forth in PCT Patent Publication No. WO 2009/044392.

In another aspect the invention provides a pharmaceutical composition comprising a molecule of the invention, in an amount effective to inhibit human gene expression; and a pharmaceutically acceptable carrier.

More specifically, the invention provides methods and compositions useful in treating a subject suffering from acute renal failure (ARF), hearing loss, glaucoma, acute respiratory distress syndrome (ARDS) and other acute lung and respiratory injuries, injury (e.g. ischemia-reperfusion injury) in organ transplant including lung, kidney, bone marrow, heart, pancreas, cornea or liver transplantation and including Delayed Graft Function (DGF) nephrotoxicity, spinal cord injury, pressure sores, dry eye syndrome, oral mucositis, ischemic ocular neuropathy (ION) and chronic obstructive pulmonary disease (COPD).

The methods of the invention comprise administering to the subject one or more siRNA compounds which inhibit expression of a gene. The novel structures disclosed herein, when integrated into antisense and corresponding sense nucleic acid sequences to any target gene, provides siRNA compound useful in reducing expression of that target gene. The target gene is a mammalian or non-mammalian gene.

BRIEF DESCRIPTION OF THE FIGURES

FIGS. 1A-1I show chemical structures of some possible 3' alkyl/alkyl derivative overhangs as covalently attached to the 3' terminal nucleotide (DNA or RNA) of the oligonucleotide strand via a phosphodiester bond. B on the nucleotide moiety refers to nucleotide "base"; R in each instance is either H or OH; FIG. 1A shows a 3' terminal nucleotide covalently linked to a propanol moiety via a phosphodiester linkage; FIG. 1B shows a 3' terminal nucleotide covalently linked via a phosphodiester linkage to a C3Pi moiety; FIG. 1C shows a 3' terminal nucleotide covalently linked via a phosphodiester linkage to a C3Pi-C3OH moiety (C3 is covalently linked to the C3OH via a phosphodiester bond); FIG. 1D shows a 3' terminal nucleotide covalently linked to a C3Pi-C3Pi moiety via a phosphodiester linkage; FIG. 1E shows a 3' terminal nucleotide covalently linked to C3Pi-C3Pi-C3OH via a phosphodiester linkage. FIG. 1F shows a 3' terminal nucleotide covalently linked to C3Pi-C3Pi-C3Pi via a phosphodiester linkage. FIG. 1G shows a 3' terminal nucleotide covalently linked to C3Pi-rAb or C3Pi-dAb via a phosphodiester linkage. FIG. 1H shows a 3' terminal nucleotide covalently linked to rAb-C3Pi (R1=OH) or dAb-C3Pi (R1=H) via a phosphodiester linkage. FIG. 1I shows a 3' terminal nucleotide covalently linked to rAb-rAb (R1=R2=OH) or dAb-rAb (R1=H, R2=OH) or rAb-dAb (R1=OH, R2=H) or dAb-dAb (R1=R2=H) via a phosphodiester linkage.

DETAILED DESCRIPTION OF THE INVENTION

Figure 1H:
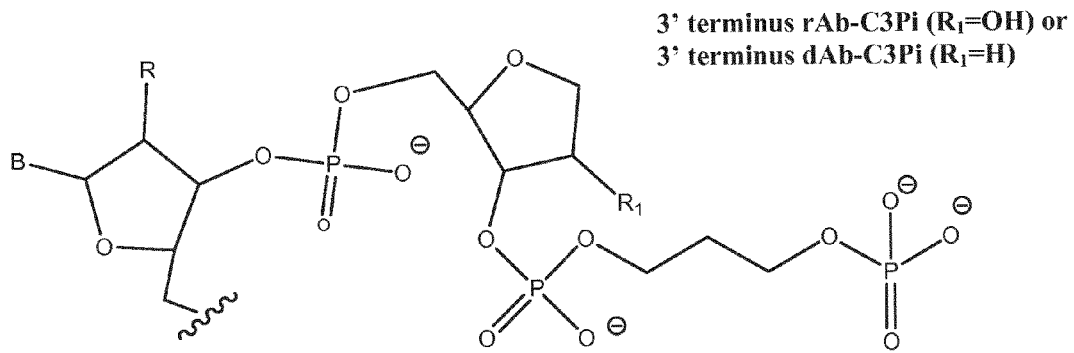
Figure 1I:
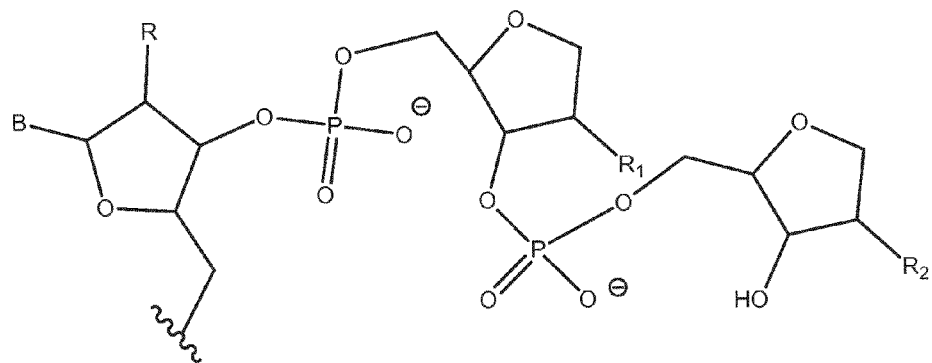
Figure 2A:
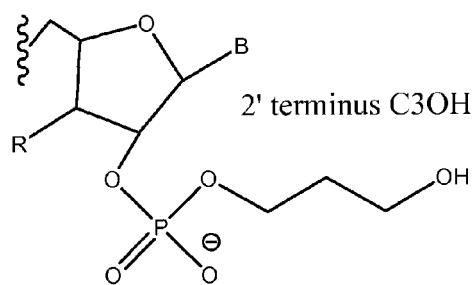
FIGS. 2A-2F are analogous to FIGS. 1A-1F, except that the 3'-terminus non-nucleotide overhangs are attached to the 2' position of the ribose moiety rather than the 3'-position.
Figure 2B:
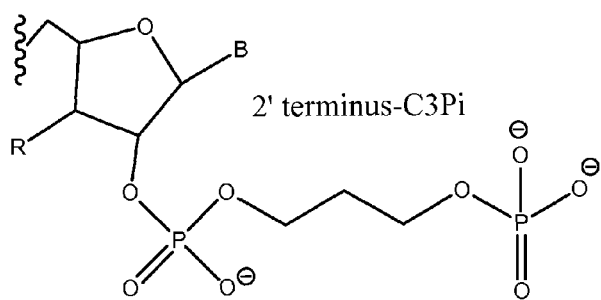
Figure 2C:
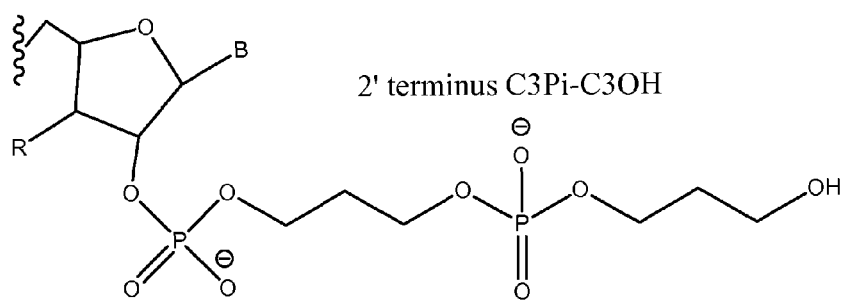
Figure 2D:
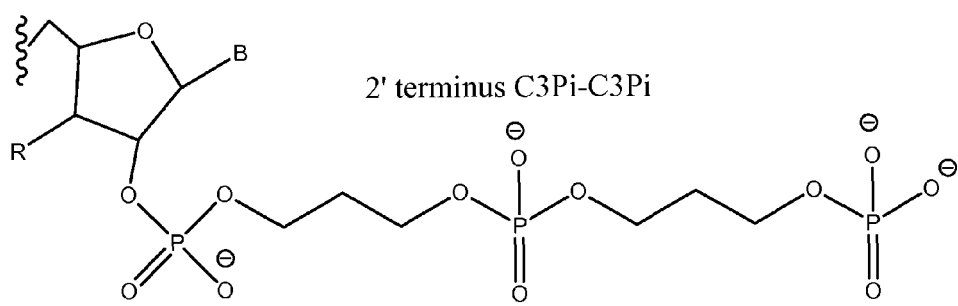
Figure 2E:
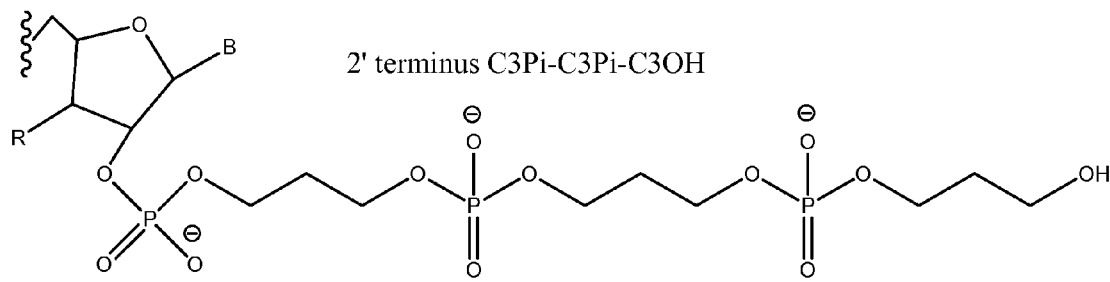
Figure 2F:
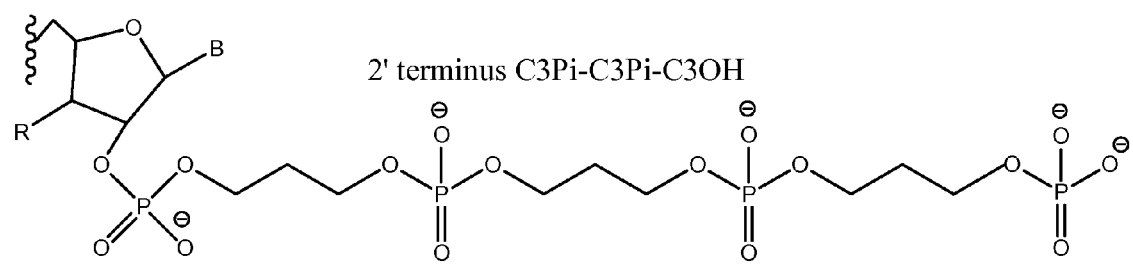
Figure 3A:
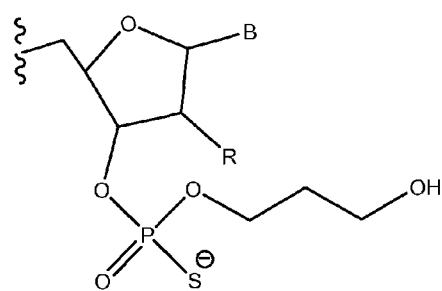
FIGS. 3A-3I illustrate some specific examples of 3'-terminus nucleotides with overhangs in accordance with embodiments of the invention, in some cases in which an oxygen atom attached to phosphorous has been replaced with sulfur.
Figure 3B:
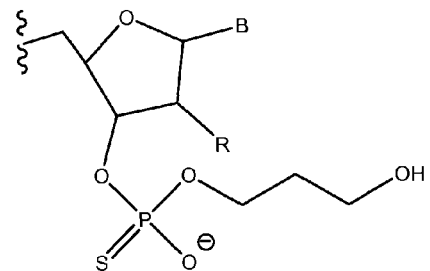
Figure 3C:
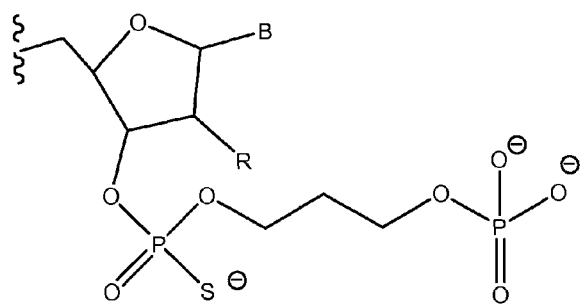
Figure 3D:
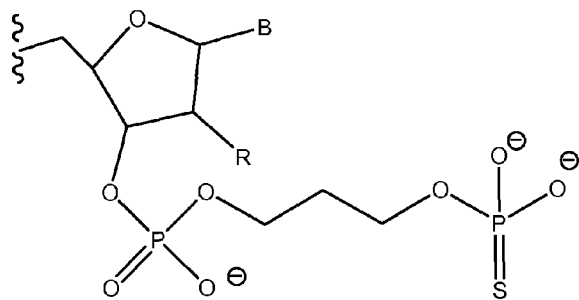
Figure 3E:
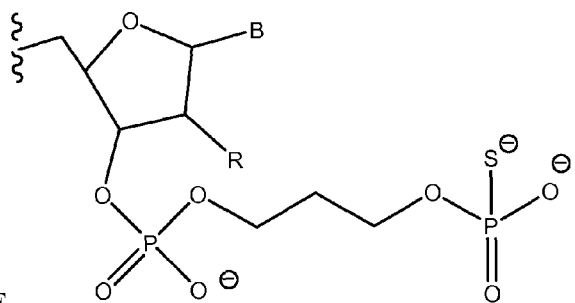
Figure 3F:
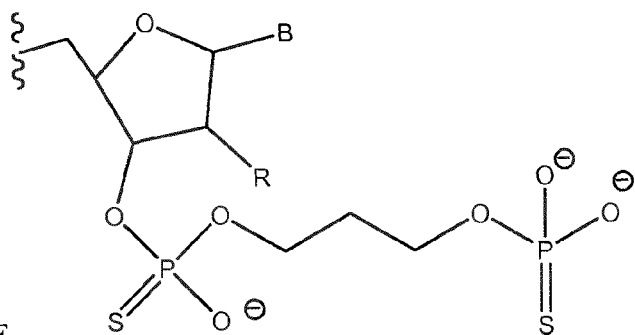
Figure 3G:
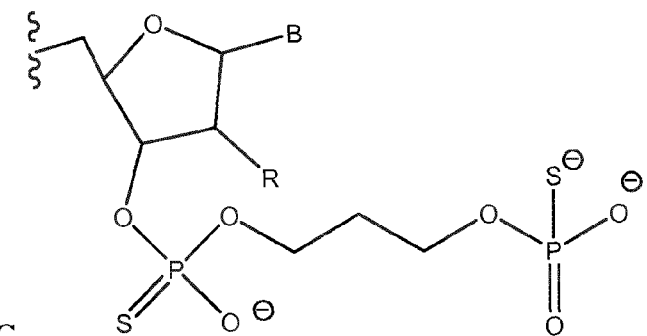
Figure 3H:
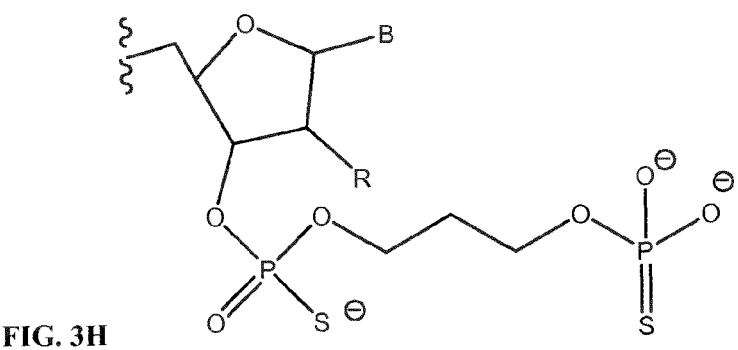
Figure 3I:
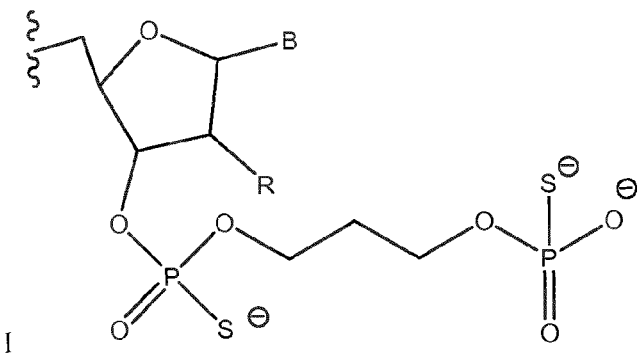

The present application relates to double stranded siRNA compounds comprising at least one non-nucleotide moiety covalently attached at the 3' terminus of one or both of the sense and antisense strands. The non-nucleotide moiety is selected from an abasic moiety, an inverted abasic moiety, an alkyl moiety or derivative thereof, and an inorganic phosphate.

Structural Design

In one aspect the provided herein are double stranded nucleic acid molecules comprising a sense strand and an antisense strand, wherein at least one strand comprises 1, 2, 3, 4, or 5 non-nucleotide moieties covalently attached at the 3' terminal end; wherein the non-nucleotide moiety is selected from an alkyl (hydrocarbon) moiety or a derivative thereof and a phosphate based moiety. In certain preferred embodiment the non-nucleotide moiety includes an alkyl moiety or an alkyl derivative moiety. In some embodiments the at least one strand is the antisense stand. In preferred embodiments the antisense strand comprises two non-nucleotide moieties covalently attached at the 3' terminal end, including C3-C3; C3-C3-Pi; C3-C3-Ps; idAb-idAb In some embodiments, provided are double stranded nucleic acid molecules having the structure (A1):

(A1)　　5'　　(N)x - Z　　　3' (antisense strand)

3' Z'-(N')y -z"　　5' (sense strand)

wherein each of N and N' is a nucleotide which may be unmodified or modified, or an unconventional moiety;
wherein each of (N)x and (N')y is an oligonucleotide in which each consecutive N or N' is joined to the next N or N' by a covalent bond;
wherein at least one of Z or Z' is present and comprises a non-nucleotide moiety covalently attached at the 3' terminus of the strand in which it is present;

wherein z" may be present or absent, but if present is a capping moiety covalently attached at the 5' terminus of (N') y;

wherein each of x and y is independently an integer between 18 and 40;

wherein the sequence of (N')y has complementarity to the sequence of (N)x; and wherein the sequence of (N)x has complementarity to a consecutive sequence in a target RNA.

In some embodiments the covalent bond joining each consecutive N or N' is a phosphodiester bond.

In some embodiments x=y=19 to 27, for example 19, 20, 21, 22, 23, 24, 25, 26, 27. In some embodiments x=y and each of x and y is 19, 20, 21, 22 or 23. In various embodiments x=y=19.

In some embodiments x=y=19 and one of Z or Z' is present and consists of two non-nucleotide moieties.

In some embodiments x=y=19 and Z' is present and consists of two non-nucleotide moieties.

In preferred embodiments x=y=19 and Z is present and consists two non-nucleotide moieties.

In preferred embodiments x=y=19 and Z is present and consists of two non-nucleotide moieties; and Z' is present and consists of one non-nucleotide moiety.

In additional embodiments x=y=19 and Z and Z' are present and each independently comprises two non-nucleotide moieties.

In some embodiments the double stranded nucleic acid molecules comprise a DNA moiety or a mismatch to the target at position 1 of the antisense strand (5' terminus). Such a structure is described herein. According to one embodiment provided are double stranded nucleic acid molecules having a structure (A2) set forth below:

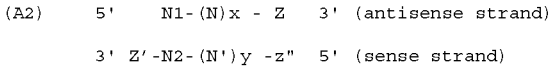

(A2)   5'   N1-(N)x - Z    3' (antisense strand)
       3'   Z'-N2-(N')y -z" 5' (sense strand)

wherein each of N2, N and N' is an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y has complementarity to the sequence of (N)x and (N)x has complementarity to a consecutive sequence in a target RNA;

wherein N1 is covalently bound to (N)x and is mismatched to the target RNA or is a complementary DNA moiety to the target RNA;

wherein N1 is a moiety selected from the group consisting of natural or modified uridine, deoxyribouridine, ribothymidine, deoxyribothymidine, adenosine or deoxyadenosine;

wherein z" may be present or absent, but if present is a capping moiety covalently attached at the 5' terminus of N2-(N')y; and wherein at least one of Z or Z' is present and comprises a non-nucleotide moiety covalently attached at the 3' terminus of the strand in which it is present.

In some embodiments x=y=18 and one of Z or Z' is present and consists of two non-nucleotide moieties.

In some embodiments x=y=18 and Z' is present and consists of two non-nucleotide moieties.

In preferred embodiments x=y=18 and Z is present and consists two non-nucleotide moieties.

In preferred embodiments x=y=18 and Z is present and consists of two non-nucleotide moieties; and Z' is present and consists of one non-nucleotide moiety.

In additional embodiments x=y=18 and Z and Z' are present and each independently comprises two non-nucleotide moieties.

In some embodiments the sequence of (N')y is fully complementary to the sequence of (N)x. In various embodiments sequence of N2-(N')y is complementary to the sequence of N1-(N)x. In some embodiments (N)x comprises an antisense that is fully complementary to about 17 to about 39 consecutive nucleotides in a target RNA. In other embodiments (N)x comprises an antisense that is substantially complementary to about 17 to about 39 consecutive nucleotides in a target RNA.

In some embodiments N1 and N2 form a Watson-Crick base pair. In some embodiments N1 and N2 form a non-Watson-Crick base pair. In some embodiments a base pair is formed between a ribonucleotide and a deoxyribonucleotide.

In some embodiments x=y=18, x=y=19 or x=y=20. In preferred embodiments x=y=18. When x=18 in N1-(N)x, N1 refers to position 1 and positions 2-19 are included in (N)18 When y=18 in N2-(N')y, N2 refers to position 19 and positions 1-18 are included in (N')18.

In some embodiments N1 is covalently bound to (N)x and is mismatched to the target RNA. In various embodiments N1 is covalently bound to (N)x and is a DNA moiety complementary to the target RNA.

In some embodiments a uridine in position 1 of the antisense strand is substituted with an N1 selected from adenosine, deoxyadenosine, deoxyuridine (dU), ribothymidine or deoxythymidine. In various embodiments N1 selected from adenosine, deoxyadenosine or deoxyuridine.

In some embodiments guanosine in position 1 of the antisense strand is substituted with an N1 selected from adenosine, deoxyadenosine, uridine, deoxyuridine, ribothymidine or deoxythymidine. In various embodiments N1 is selected from adenosine, deoxyadenosine, uridine or deoxyuridine.

In some embodiments cytidine in position 1 of the antisense strand is substituted with an N1 selected from adenosine, deoxyadenosine, uridine, deoxyuridine, ribothymidine or deoxythymidine. In various embodiments N1 is selected from adenosine, deoxyadenosine, uridine or deoxyuridine.

In some embodiments adenosine in position 1 of the antisense strand is substituted with an N1 selected from deoxyadenosine, deoxyuridine, ribothymidine or deoxythymidine. In various embodiments N1 selected from deoxyadenosine or deoxyuridine.

In some embodiments N1 and N2 form a base pair between uridine or deoxyuridine, and adenosine or deoxyadenosine. In other embodiments N1 and N2 form a base pair between deoxyuridine and adenosine.

In some embodiments the double stranded nucleic acid molecule is a siRNA, siNA or a miRNA. The double stranded nucleic acid molecules as provided herein are also referred to as "duplexes".

In certain preferred embodiments x=y=18. In some embodiments N1 and N2 form a Watson-Crick base pair. In other embodiments N1 and N2 form a non-Watson-Crick base pair. In certain embodiments N1 is selected from the group consisting of riboadenosine, modified riboadenosine, deoxyriboadenosine, modified deoxyriboadenosine. In other embodiments N1 is selected from the group consisting of ribouridine, deoxyribouridine, modified ribouridine, and modified deoxyribouridine.

In certain embodiments position 1 in the antisense strand (5' terminus) comprises deoxyribouridine (dU) or adenosine.

In some embodiments N1 is selected from the group consisting of riboadenosine, modified riboadenosine, deoxyriboadenosine, modified deoxyriboadenosine and N2 is selected from the group consisting of ribouridine, deoxyribouridine, modified ribouridine, and modified deoxyribouridine. In certain embodiments N1 is selected from the group consisting of riboadenosine and modified riboadenosine and N2 is selected from the group consisting of ribouridine and modified ribouridine.

In certain embodiments N1 is selected from the group consisting of ribouridine, deoxyribouridine, modified ribouridine, and modified deoxyribouridine and N2 is selected from the group consisting of riboadenosine, modified riboadenosine, deoxyriboadenosine, modified deoxyriboadenosine. In certain embodiments N1 is selected from the group consisting of ribouridine and deoxyribouridine and N2 is selected from the group consisting of riboadenosine and modified riboadenosine. In certain embodiments N1 is ribouridine and N2 is riboadenosine. In certain embodiments N1 is deoxyribouridine and N2 is riboadenosine.

In some embodiments of Structure (A2), N1 includes 2'OMe sugar-modified ribouracil or 2'OMe sugar-modified riboadenosine. In certain embodiments of structure (A2), N2 includes a 2'OMe sugar modified ribonucleotide or deoxyribonucleotide.

In some embodiments of Structure (A2), N1 includes 2'OMe sugar-modified ribouracil or 2'OMe sugar-modified ribocytosine. In certain embodiments of structure (A2), N2 includes a 2'OMe sugar modified ribonucleotide.

In some embodiments each of N and N' is an unmodified nucleotide. In some embodiments at least one of N or N' includes a chemically modified nucleotide or an unconventional moiety. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments at least one of N or N' includes a 2'OMe sugar-modified ribonucleotide.

In some embodiments the sequence of (N')y is fully complementary to the sequence of (N)x. In other embodiments the sequence of (N')y is substantially complementary to the sequence of (N)x.

In some embodiments (N)x includes an antisense sequence that is fully complementary to about 17 to about 39 consecutive nucleotides in a target RNA. In other embodiments (N)x includes an antisense that is substantially complementary to about 17 to about 39 consecutive nucleotides in a target RNA.

In some embodiments the nucleic acid molecules disclosed herein are siRNA, siNA or miRNA.

In some embodiments of Structures A1 and A2, Z is present and Z' is absent. In other embodiments Z' is present and Z is absent. In additional embodiments both Z and Z' are present. In some embodiments Z and Z' are present and are identical. In further embodiments Z and Z' are present and are different. In some embodiments Z and Z' are independently 2, 3, 4 or 5 non-nucleotide moieties or a combination of 2, 3, 4, or 5 non-nucleotide moieties and nucleotides. In some embodiments each of Z and or Z' consist of two (2) non-nucleotide moieties covalently attached to the 3' terminus of the siRNA strand via a phosphodiester bond.

A non-nucleotide moiety is selected from the group consisting of an abasic moiety, an inverted abasic moiety, an alkyl moiety or derivative thereof, and an inorganic phosphate. In some embodiments a non-nucleotide moiety is an alkyl moiety or derivative thereof. In some embodiments the alkyl moiety comprises a terminal functional group selected from the group consisting of an alcohol, a terminal amine, a terminal phosphate and a terminal phosphorothioate moiety.

In some embodiments Z is present and comprises one or more non-nucleotide moieties selected from the group consisting of an abasic moiety, an inverted abasic moiety, hydrocarbon moiety or derivative thereof, and an inorganic phosphate. In some embodiments Z is present and consists of two alkyl moieties or derivatives thereof.

In additional embodiments Z' is present and comprises one or more non-nucleotide moieties selected from the group consisting of an abasic moiety, an inverted abasic moiety, a hydrocarbon moiety, and an inorganic phosphate. In some embodiments Z' is present and comprises one or more alkyl moieties or derivatives thereof.

In some embodiments Z is present and consists of two alkyl moieties or derivatives thereof and Z' is present and consists of a single alkyl moiety or derivative thereof.

In some embodiments each of Z and Z' includes an abasic moiety, for example a deoxyriboabasic moiety (referred to herein as "dAb") or riboabasic moiety (referred to herein as "rAb"). In some embodiments each of Z and/or Z' comprises two covalently linked abasic moieties and is for example 5'>3' dAb-dAb or rAb-rAb or dAb-rAb or rAb-dAb. Each moiety is covalently conjugated to an adjacent moiety via a covalent bond, preferably a phospho-based bond. In some embodiments the phospho-based bond is a phosphorothioate, a phosphonoacetate or a phosphodiester bond.

In some embodiments each of Z and/or Z' independently includes a C2, C3, C4, C5 or C6 alkyl moiety, optionally a C3 [propane, —(CH2)$_3$-] moiety or a derivative thereof e.g. propanol (C3-OH), propanediol, or phosphodiester derivative of propanediol ("C3Pi"). In preferred embodiments each of Z and/or Z' includes two hydrocarbon moieties and in some examples is C3-C3. Each C3 is covalently conjugated to an adjacent C3 via a covalent bond, preferably a phospho-based bond. In some embodiments the phospho-based bond is a phosphorothioate, a phosphonoacetate or a phosphodiester bond.

In some embodiments of Structure A1 and Structure A2 at least one of Z or Z' is present and comprises at least two non-nucleotide moieties covalently attached to the strand in which it is present. In some embodiments each of Z and Z' independently includes a C3 alkyl, C3 alcohol or C3 ester moiety. In some embodiments Z' is absent and Z is present and includes a non-nucleotide C3 moiety. In some embodiments Z is absent and Z' is present and includes a non-nucleotide C3 moiety.

In some embodiments of Structures A1 and A2, each of N and N' is an unmodified nucleotide. In some embodiments at least one of N or N' includes a chemically modified nucleotide or an unconventional moiety. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments at least one of N or N' includes a 2'OMe sugar-modified ribonucleotide.

In some embodiments the sequence of (N')y is fully complementary to the sequence of (N)x. In other embodiments the sequence of (N')y is substantially complementary to the sequence of (N)x.

In other embodiments the compound of Structure A1 or Structure A2 includes at least one ribonucleotide modified in the sugar residue. In some embodiments the compound includes a modification at the 2' position of the sugar residue. In some embodiments the modification in the 2' position includes the presence of an amino, a fluoro, an alkoxy or an alkyl moiety. In certain embodiments the 2' modification includes an alkoxy moiety, In preferred embodiments the alkoxy moiety is a methoxy moiety (also known as 2'-O-methyl; 2'OMe; 2'-OCH3). In some embodiments the nucleic acid compound includes 2'OMe sugar modified alternating ribonucleotides in one or both of the antisense and the sense strands. In other embodiments the compound includes 2'OMe sugar modified ribonucleotides in the antisense strand, (N)x or N1-(N)x, only. In certain embodiments the middle ribonucleotide of the antisense strand; e.g. ribonucleotide in position 10 in a 19-mer strand is unmodified. In various embodiments the nucleic acid compound includes at least 5 alternating 2'OMe sugar modified and unmodified ribonucleotides. In additional embodiments the compound of Structure A1 or Structure A2 includes modified ribonucleotides in alternating positions wherein each ribonucleotide at the 5' and 3' termini of (N)x or N1-(N)x are modified in their sugar residues, and each ribonucleotide at the 5' and 3' termini of (N')y or N2-(N)y are unmodified in their sugar residues.

In some embodiments the double stranded molecule includes one or more of the following modifications
a) N in at least one of positions 5, 6, 7, 8, or 9 from the 5' terminus of the antisense strand is selected from a 2'5' nucleotide or a mirror nucleotide;
b) N' in at least one of positions 9 or 10 from the 5' terminus of the sense strand is selected from a 2'5' nucleotide and a pseudoUridine; and
c) N' in 4, 5, or 6 consecutive positions at the 3' terminus positions of (N')y comprises a 2'5' nucleotide.

In some embodiments the double stranded molecule includes a combination of the following modifications
a) the antisense strand includes a 2'5' nucleotide or a mirror nucleotide in at least one of positions 5, 6, 7, 8, or 9 from the 5' terminus; and
b) the sense strand includes at least one of a 2'5' nucleotide and a pseudoUridine in positions 9 or 10 from the 5' terminus.

In some embodiments the double stranded molecule includes a combination of the following modifications
a) the antisense strand includes a 2'5' nucleotide or a mirror nucleotide in at least one of positions 5, 6, 7, 8, or 9 from the 5' terminus; and
c) the sense strand includes 4, 5, or 6 consecutive 2'5' nucleotides at the 3' penultimate or 3' terminal positions.

In some embodiments, the sense strand [(N)x or N1-(N)x] includes 1, 2, 3, 4, 5, 6, 7, 8, or 9 2'OMe sugar modified ribonucleotides. In some embodiments, the antisense strand includes 2'OMe modified ribonucleotides at positions 2, 4, 6, 8, 11, 13, 15, 17 and 19. In other embodiments antisense strand includes 2'OMe modified ribonucleotides at positions 1, 3, 5, 7, 9, 11, 13, 15, 17 and 19. In other embodiments the antisense strand includes 2'OMe modified ribonucleotides at positions 3, 5, 7, 9, 11, 13, 15, 17 and 19. In some embodiments the antisense strand includes one or more 2'OMe sugar modified pyrimidines. In some embodiments all the pyrimidine nucleotides in the antisense strand are 2'OMe sugar modified. In some embodiments the sense strand includes 2'OMe sugar modified pyrimidines.

In some embodiments of Structure A1 and Structure A2, the sense strand and the antisense strand are independently phosphorylated or unphosphorylated at the 3' terminus and at the 5' terminus. In some embodiments of Structure A1 and Structure A2, the sense strand and the antisense strand are unphosphorylated at the 3' and 5' termini. In other embodiments the sense strand and the antisense strand are phosphorylated at the 3' termini.

In some embodiments of Structure A1 and Structure A2 (N)y includes at least one unconventional moiety selected from a mirror nucleotide, a 2'5' nucleotide and a TNA. In some embodiments the unconventional moiety is a mirror nucleotide. In various embodiments the mirror nucleotide is selected from an L-ribonucleotide (L-RNA) and an L-deoxyribonucleotide (L-DNA). In preferred embodiments the mirror nucleotide is L-DNA. In certain embodiments the sense strand comprises an unconventional moiety in position 9 or 10 (from the 5' terminus). In preferred embodiments the sense strand includes an unconventional moiety in position 9 (from the 5' terminus). In some embodiments the sense strand is 19 nucleotides in length and comprises 4, 5, or 6 consecutive unconventional moieties in positions 15, (from the 5' terminus). In some embodiments the sense strand includes 4 consecutive 2'5' ribonucleotides in positions 15, 16, 17, and 18. In some embodiments the sense strand includes 5 consecutive 2'5' ribonucleotides in positions 15, 16, 17, 18 and 19. In various embodiments the sense strand further comprises Z'. In some embodiments Z' includes a C3OH moiety or a C3Pi moiety.

In some embodiments of Structure A1 (N')y includes at least one L-DNA moiety. In some embodiments x=y=19 and (N')y, consists of unmodified ribonucleotides at positions 1-17 and 19 and one L-DNA at the 3' penultimate position (position 18). In other embodiments x=y=19 and (N')y consists of unmodified ribonucleotides at positions 1-16 and 19 and two consecutive L-DNA at the 3' penultimate position (positions 17 and 18). In various embodiments the unconventional moiety is a nucleotide joined to an adjacent nucleotide by a 2'-5' internucleotide phosphate linkage. According to various embodiments (N')y includes 2, 3, 4, 5, or 6 consecutive ribonucleotides at the 3' terminus linked by 2'-5' internucleotide linkages. In one embodiment, four consecutive nucleotides at the 3' terminus of (N')y are joined by three 2'-5' phosphodiester bonds, wherein one or more of the 2'-5' nucleotides which form the 2'-5' phosphodiester bonds further includes a 3'-O-methyl (3'OMe) sugar modification. Preferably the 3' terminal nucleotide of (N')y includes a 2'OMe sugar modification. In certain embodiments x=y=19 and (N')y includes two or more consecutive nucleotides at positions 15, 16, 17, 18 and 19 include a nucleotide joined to an adjacent nucleotide by a 2'-5' internucleotide bond (2'-5' nucleotide). In various embodiments the nucleotide forming the 2'-5' internucleotide bond includes a 3' deoxyribose nucleotide or a 3' methoxy nucleotide (3' H or 3'OMe in place of a 3' OH). In some embodiments x=y=19 and (N')y includes 2'-5' nucleotides at positions 15, 16 and 17 such that adjacent nucleotides are linked by a 2'-5' internucleotide bond between positions 15-16, 16-17 and 17-18; or at positions, 15, 16, 17, 18, and 19 such that adjacent nucleotides are linked by a 2'-5' internucleotide bond between positions 15-16, 16-17, 17-18 and 18-19 and a 3'OH is available at the 3' terminal nucleotide or at positions 16, 17 and 18 such that adjacent nucleotides are linked by a 2'-5' internucleotide bond between positions 16-17, 17-18 and 18-19. In some embodiments x=y=19 and (N')y includes 2'-5' nucleotides at positions 16 and 17 or at positions 17 and 18 or at positions 15 and 17 such that adjacent nucleotides are linked by a 2'-5' internucleotide bond between positions 16-17 and 17-18 or between positions 17-18 and 18-19 or between positions 15-16 and 17-18, respectively. In other embodiments the pyrimidine ribonucleotides (rU, rC) in (N')y are substituted with nucleotides joined to the adjacent nucleotide by a 2'-5' internucleotide bond. In some embodiments x=y=19 and (N')y comprises five consecutive nucleotides at the 3' terminus joined by four 2'-5' linkages, specifically the linkages between the nucleotides position 15-16, 16-17, 17-18 and 18-19.

In some embodiments x=y=19 and (N')y comprises five consecutive nucleotides at the 3' terminus joined by four 2'-5' linkages and optionally further includes Z' and z' independently selected from an inverted abasic moiety and a C3 alkyl [C3; 1,3-propanediol mono(dihydrogen phosphate)] cap. The C3 alkyl cap is covalently linked to the 3' or 5' terminal nucleotide. In some embodiments the 3' C3 terminal cap further comprises a 3' phosphate. In some embodiments the 3' C3 terminal cap further comprises a 3' terminal hydroxyl group.

In some embodiments x=y=19 and (N')y comprises an L-DNA position 18; and (N')y optionally further includes Z' and z' independently selected from an inverted abasic moiety and a C3 alkyl [C3; 1,3-propanediol mono(dihydrogen phosphate)] cap.

In some embodiments (N')y comprises a 3' terminal phosphate (i.e. phosphorylated at the 3' terminus). In some embodiments (N')y comprises a 3' terminal hydroxyl.

In some embodiments x=y=19 and (N)x includes 2'OMe sugar modified ribonucleotides at positions 1, 3, 5, 7, 9, 11, 13, 15, 17, 19 or at positions 2, 4, 6, 8, 11, 13, 15, 17, 19. In some embodiments x=y=19 and (N)x includes 2'OMe sugar modified pyrimidines. In some embodiments all pyrimidines in (N)x include the 2'OMe sugar modification.

In some embodiments of structure A2 x=y=18 and N2 is a riboadenosine moiety. In some embodiments x=y=18, and N2-(N')y comprises five consecutive nucleotides at the 3' terminus joined by four 2'-5' linkages, specifically the linkages between the nucleotides position 15-16, 16-17, 17-18 and 18-19. In some embodiments the linkages include phosphodiester bonds. In some embodiments x=y=18 and N2-(N')y comprises five consecutive nucleotides at the 3' terminus joined by four 2'-5' linkages and optionally further includes Z' and z' independently selected from an inverted abasic moiety and a C3 alkyl [C3; 1,3-propanediol mono (dihydrogen phosphate)] cap. In some embodiments x=y=18 and N2-(N')y comprises an L-DNA position 18; and (N')y optionally further includes Z' and z' independently selected from an inverted abasic moiety and a C3 alkyl [C3; 1,3-propanediol mono(dihydrogen phosphate)] cap. In some embodiments N2-(N')y comprises a 3' terminal phosphate. In some embodiments N2-(N')y comprises a 3' terminal hydroxyl. In some embodiments x=y=18 and N1-(N)x includes 2'OMe sugar modified ribonucleotides in positions 1, 3, 5, 7, 9, 11, 13, 15, 17, 19 or in positions 1, 3, 5, 9, 11, 13, 15, 17, 19, or in positions 3, 5, 9, 11, 13, 15, 17, or in positions 2, 4, 6, 8, 11, 13, 15, 17, 19. In some embodiments x=y=18 and N1-(N)x includes 2'OMe sugar modified ribonucleotides at positions 11, 13, 15, 17 and 19 (from 5' terminus). In some embodiments x=y=18 and N1-(N)x includes 2'OMe sugar modified ribonucleotides in positions 1, 3, 5, 7, 9, 11, 13, 15, 17, 19 or in positions 3, 5, 7, 9, 11, 13, 15, 17, 19. In some embodiments x=y=18 and N1-(N)x includes 2'OMe sugar modified ribonucleotides in positions 2, 4, 6, 8, 11, 13, 15, 17, 19.

In some embodiments x=y=18 and N1-(N)x includes 2'OMe sugar modified pyrimidines. In some embodiments all pyrimidines in (N)x include the 2'OMe sugar modification. In some embodiments the antisense strand further comprises an L-DNA or a 2'-5' nucleotide in position 5, 6 or 7 (5'>3'). In other embodiments the antisense strand further comprises a ribonucleotide, which generates a 2'5' internucleotide linkage in between the ribonucleotides in positions 5-6 or 6-7 (5'>3').

In additional embodiments N1-(N)x further includes Z wherein Z comprises a non-nucleotide overhang. In some embodiments the non-nucleotide overhang is C3-C3 [1,3-propanediol mono(dihydrogen phosphate)]2.

In some embodiments of Structure A2, (N)y includes at least one L-DNA moiety. In some embodiments x=y=18 and (N')y consists of unmodified ribonucleotides at positions 1-16 and 18 and one L-DNA at the 3' penultimate position (position 17). In other embodiments x=y=18 and (N')y consists of unmodified ribonucleotides at position 1-15 and 18 and two consecutive L-DNA at the 3' penultimate position (positions 16 and 17). In various embodiments the unconventional moiety is a nucleotide joined to an adjacent nucleotide by a 2'-5' internucleotide phosphate linkage. According to various embodiments (N')y includes 2, 3, 4, 5, or 6 consecutive ribonucleotides at the 3' terminus linked by 2'-5' internucleotide linkages. In one embodiment, four consecutive nucleotides at the 3' terminus of (N')y are joined by three 2'-5' phosphodiester bonds, wherein one or more of the 2'-5' nucleotides which form the 2'-5' phosphodiester bonds further includes a 3'-O-methyl (3'OMe) sugar modification. Preferably the 3' terminal nucleotide of (N')y includes a 2'OMe sugar modification. In certain embodiments x=y=18 and in (N')y two or more consecutive nucleotides at positions 14, 15, 16, 17, and 18 include a nucleotide joined to an adjacent nucleotide by a 2'-5' internucleotide bond. In various embodiments the nucleotide forming the 2'-5' internucleotide bond includes a 3' deoxyribose nucleotide or a 3' methoxy nucleotide. In some embodiments x=y=18 and (N')y includes nucleotides joined to the adjacent nucleotide by a 2'-5' internucleotide bond between positions 15-16, 16-17 and 17-18 or between positions 16-17 and 17-18. In some embodiments x=y=18 and (N')y includes nucleotides joined to the adjacent nucleotide by a 2'-5' internucleotide bond between positions 14-15, 15-16, 16-17, and 17-18 or between positions 15-16, 16-17, and 17-18 or between positions 16-17 and 17-18 or between positions 17-18 or between positions 15-16 and 17-18. In other embodiments the pyrimidine ribonucleotides (rU, rC) in (N')y are substituted with nucleotides joined to the adjacent nucleotide by a 2'-5' internucleotide bond.

In some embodiments of Structure A1 and Structure A2 each N consists of an unmodified ribonucleotide. In some embodiments of Structure A1 and Structure A2 each N' consists of an unmodified nucleotide. In preferred embodiments, at least one of N and N' is a modified ribonucleotide or an unconventional moiety.

In other embodiments the molecule of Structure A1 or Structure A2 includes at least one ribonucleotide modified in the sugar residue. In some embodiments the compound includes a modification at the 2' position of the sugar residue. In some embodiments the modification at the 2' position includes the presence of an amino, a fluoro, an alkoxy or an alkyl moiety. In certain embodiments the 2' modification includes an alkoxy moiety, In preferred embodiments the alkoxy moiety is a methoxy moiety (also known as 2'-O-methyl; 2'OMe; 2'-OCH3). In some embodiments the nucleic acid compound includes 2'OMe sugar modified alternating ribonucleotides in one or both of the antisense and the sense strands. In other embodiments the compound includes 2'OMe sugar modified ribonucleotides in the antisense strand, (N)x or N1-(N)x, only. In certain embodiments the middle ribonucleotide of the antisense strand; e.g. ribonucleotide in position 10 in a 19-mer strand is unmodified. In various embodiments the nucleic acid compound includes at least 5 alternating 2'OMe sugar modified and unmodified ribonucleotides.

In additional embodiments the compound of Structure A1 or Structure A2 includes modified ribonucleotides in alternating positions wherein each ribonucleotide at the 5' and 3' termini of (N)x or N1-(N)x are modified in their sugar residues, and each ribonucleotide at the 5' and 3' termini of (N')y or N2-(N)y are unmodified in their sugar residues.

In some embodiments, (N)x or N1-(N)x includes 2'OMe modified ribonucleotides at positions 2, 4, 6, 8, 11, 13, 15, 17 and 19. In other embodiments (N)x (N)x or N1-(N)x includes 2'OMe modified ribonucleotides at positions 1, 3, 5, 7, 9, 11, 13, 15, 17 and 19. In some embodiments (N)x or N1-(N)x includes 2'OMe modified pyrimidines. In some embodiments all the pyrimidine nucleotides in (N)x or N1-(N)x are 2'OMe modified. In some embodiments (N')y or N2-(N')y includes 2'OMe modified pyrimidines. In additional embodiments the compound of Structure A1 or Structure A2 includes modified ribonucleotides in alternating positions wherein each ribonucleotide at the 5' and 3' termini of (N)x or N1-(N)x are modified in their sugar residues, and each ribonucleotide at the 5' and 3' termini of (N')y or N2-(N)y are unmodified in their sugar residues.

The nucleic acid molecules disclosed herein may have a blunt end on one end, for example when Z and z" are absent or wherein Z' is absent. The nucleic acid molecule may be modified with modified nucleotides or unconventional moieties that may be located at any position along either the sense or antisense strand. The nucleic acid molecule may include about 1, 2, 3, 4, 5, 6, 7, 8, 9, 10, 11, 12, 13, 14, or 15 modified nucleotides. The nucleic acid molecule may include about 1, 2, 3, 4, 5, 6, 7, or 8 unconventional moieties. The nucleic acid molecule may include a group of about 1, 2, 3, 4, 5, 6, 7, or 8, preferably 1, 2, 3 or 4 contiguous modified nucleotides or unconventional moieties. Modified nucleic acids may be present in the sense strand only, the antisense strand only, or in both the sense strand and the antisense strand. In some embodiments the modified nucleotide comprises a 2' sugar modified nucleotide, including 2'O-methyl modified nucleotide, 2' deoxyfluoro modified nucleotide, 2'-amino modified nucleotide. In some embodiments the unconventional moiety comprises a mirror nucleotide (i.e. L-DNA or L-RNA) or a nucleotide able to form a 2'-5' linkage (2'5' nucleotide).

As used herein, the term "duplex region" refers to the region in the double stranded molecule in which two complementary or substantially complementary oligonucleotides form base pairs with one another, typically by Watson-Crick base pairing or by any other manner that allows for a duplex formation. For example, an oligonucleotide strand having 19 nucleotide units can base pair with a complementary oligonucleotide of 19 nucleotide units, or can base pair with 15, 16, 17 or 18 bases on each strand such that the "duplex region" consists of 15, 16, 17 or 18 base pairs. The remaining base pairs may, for example, exist as 5' and 3' overhangs. Further, within the duplex region, 100% complementarity is not required; substantial complementarity is allowable within a duplex region. The overhang region may consist of nucleotide or non-nucleotide moieties. As disclosed herein at least one overhang region consists of one or more non-nucleotide moieties.

Generic non-limiting nucleic acid molecule patterns are shown below where N'=sense strand nucleotide in the duplex region; z"=5'-capping moiety covalently attached at the 5' terminus of the sense strand; C3=3 carbon non-nucleotide moiety; N=antisense strand nucleotide in the duplex region; 1 dB=inverted abasic deoxyribonucleotide non-nucleotide moiety. Each N,N', is independently modified or unmodified or an unconventional moiety. The sense and antisense strands are each independently 18-40 nucleotides in length. The examples provided below have a duplex region of 19 nucleotides; however, nucleic acid molecules disclosed herein can have a duplex region anywhere between 18 and 40 nucleotides and where each strand is independently between 18 and 40 nucleotides in length. In each duplex the antisense strand (N)x is shown on top.

In some embodiments a double stranded nucleic acid molecule has the following structure:

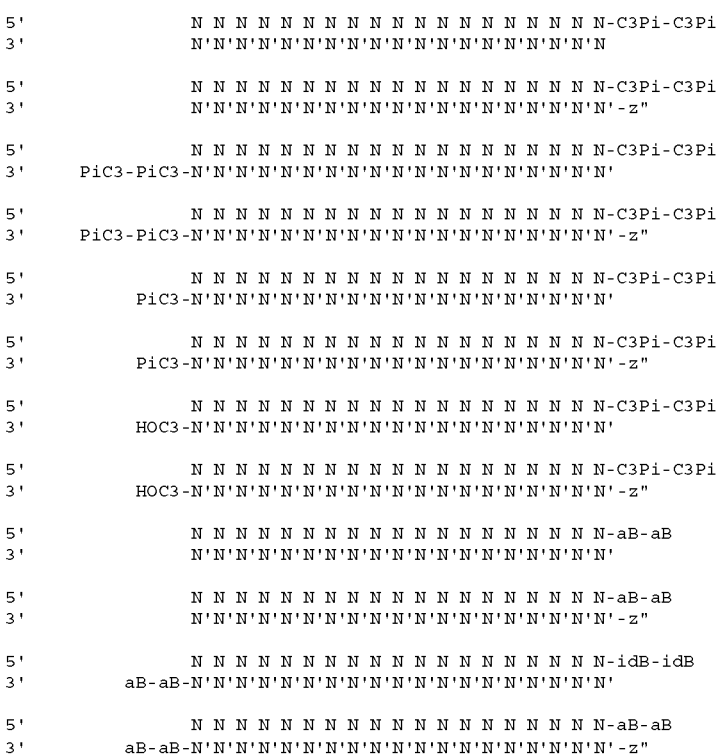

```
5'          N N N N N N N N N N N N N N N N N N-C3Pi-C3Pi
3'   PiC3-N'N'N'N'N'N'N'N'N'N'N'N'N'N'N'N'N'N

5'          N N N N N N N N N N N N N N N N N N-C3Pi-C3Pi
3'   aB-aB-N'N'N'N'N'N'N'N'N'N'N'N'N'N'N'N'N'N'

5'          N N N N N N N N N N N N N N N N N N-C3Pi-C3OH
3'          N'N'N'N'N'N'N'N'N'N'N'N'N'N'N'N'N'N

5'          N N N N N N N N N N N N N N N N N N-C3Pi-C3OH
3'          N'N'N'N'N'N'N'N'N'N'N'N'N'N'N'N'N'N'-z"

5'          N N N N N N N N N N N N N N N N N N-C3Pi-C3OH
3'   PiC3-PiC3-N'N'N'N'N'N'N'N'N'N'N'N'N'N'N'N'N'N'

5'          N N N N N N N N N N N N N N N N N N-C3Pi-C3OH
3'   PiC3-PiC3-N'N'N'N'N'N'N'N'N'N'N'N'N'N'N'N'N'N'-z"

5'          N N N N N N N N N N N N N N N N N N-C3Pi-C3OH
3'   PiC3-N'N'N'N'N'N'N'N'N'N'N'N'N'N'N'N'N'N'

5'          N N N N N N N N N N N N N N N N N N-C3Pi-C3OH
3'   PiC3-N'N'N'N'N'N'N'N'N'N'N'N'N'N'N'N'N'N'-z"

5'          N N N N N N N N N N N N N N N N N N-C3Pi-C3OH
3'   HOC3-N'N'N'N'N'N'N'N'N'N'N'N'N'N'N'N'N'N'

5'          N N N N N N N N N N N N N N N N N N-C3Pi-C3OH
3'   HOC3-N'N'N'N'N'N'N'N'N'N'N'N'N'N'N'N'N'N'-z"

5'          N N N N N N N N N N N N N N N N N N-C3Pi-C3Ps
3'          N'N'N'N'N'N'N'N'N'N'N'N'N'N'N'N'N'N

5'          N N N N N N N N N N N N N N N N N N-C3Pi-C3Ps
3'          N'N'N'N'N'N'N'N'N'N'N'N'N'N'N'N'N'N'-z"

5'          N N N N N N N N N N N N N N N N N N-C3Pi-C3Ps
3'   OHC3-PiC3-N'N'N'N'N'N'N'N'N'N'N'N'N'N'N'N'N'N'

5'          N N N N N N N N N N N N N N N N N N-C3Pi-C3Ps
3'   OHC3-PiC3-N'N'N'N'N'N'N'N'N'N'N'N'N'N'N'N'N'N'-z"
                                                    35
```

In some preferred embodiment nucleic acid molecules disclosed herein have the following structure

```
5'          N N N N N N N N N N N N N N N N N N-C3Pi-C3OH
3'   HOC3-N'N'N'N'N'N'N'N'N'N'N'N'N'N'N'N'N'N'-z"
or

5'          N N N N N N N N N N N N N N N N N N-C3Pi-C3OH
3'   iPC3-N'N'N'N'N'N'N'N'N'N'N'N'N'N'N'N'N'N'-z"
                                                    45
``` wherein of N and N' is independently a ribonucleotide which may be unmodified or modified, or is an unconventional moiety;
wherein each N is linked to the adjacent N by a covalent bond;
wherein each N' is linked to the adjacent N' by a covalent bond; and
wherein z" is a capping moiety covalently attached to the 5' terminus of the sense strand. The term "aB" refers to an abasic moiety which can be riboabasic moiety or a deoxyriboabasic moiety, or an inverted riboabasic moiety or an inverted deoxyriboabasic moiety.

In some embodiments the nucleic acid molecules disclosed herein comprise Z. In other embodiments the nucleic acid molecules disclosed herein comprise Z'. In additional embodiments both Z and Z' are present. In some embodiments Z and Z' are both present and identical. In further embodiments both Z and Z' are present and are different. In some embodiments Z and Z' independently comprise 1 or 2 non-nucleotide moieties. In some embodiments Z and Z' independently comprise 2 non-nucleotide moieties.

In some embodiments Z is present and comprises one or more non-nucleotide moieties selected from an abasic moiety an inverted abasic moiety, an alkyl moiety or derivative thereof, and an inorganic phosphate moiety.

In additional embodiments Z' is present and comprises one or more non-nucleotide moieties selected from an abasic moiety an inverted abasic moiety, an alkyl moiety or derivative thereof or an inorganic phosphate moiety.

In additional embodiments Z and/or Z' are present and independently comprise a combination of one or more nucleotide and one or more non-nucleotide moiety selected from the moieties disclosed herein.

In some embodiments each of Z and Z' includes an abasic moiety, optionally deoxyriboabasic (referred to herein as "dAb") or riboabasic (referred to herein as "rAb") nucleotides. In some embodiments each of Z and/or Z' is dAb-dAb or rAb-rAb.

In some embodiments each of Z and/or Z' independently includes an alkyl moiety, optionally a phosphodiester derivative of propanediol ((CH2)-3-Pi, referred to herein also as "C3Pi") modified moiety. In some embodiments Z and/or Z' are C3Pi-C3Pi. In a specific embodiment x=y=19 and Z comprises two propanediol derivatives, C3-C3 (i.e. —C3-Pi-C3-Pi). In various embodiments the C3 moiety is covalently linked to the 3' terminus of the sense or antisense strand via a phosphodiester bond.

In additional embodiments Z and/or Z' comprise a combination of one or more abasic moieties and unmodified nucleotides or a combination of one or more hydrocarbon moieties and unmodified nucleotides or a combination of one or more abasic and hydrocarbon moieties. In such embodiments, Z and/or Z' are optionally C3-rAb or C3-dAb.

In further embodiments relating to structure A1 or A2, the nucleic acid molecules further comprises a 2'O-Me modification on the sugar of ribonucleotides at positions 2, 4, 6, 8, 11, 13, 15, 17 and 19 of the antisense strand. In additional embodiments the compound also comprises an L-DNA nucleotide at position 18 of the sense strand. In additional embodiments the compound comprises a nucleotide joined to an adjacent nucleotide by a 2'-5' internucleotide phosphate bond. In additional embodiments x=y=19 and the nucleotides at positions 15-19 or 16-19 or 17-19 in (N')y are joined to adjacent nucleotides by 2'-5' internucleotide phosphate bonds. In some embodiments x=y=19 and the nucleotides at positions 15-19 or 16-19 or 17-19 or 15-18 or 16-18 in (N')y are joined to the adjacent nucleotides by 2'-5' internucleotide phosphate bonds.

According to certain embodiments the invention provides an siRNA compound further comprising one or more modified nucleotide, wherein the modified nucleotide possesses a modification in the sugar moiety, in the base moiety or in the internucleotide linkage moiety.

In some embodiments (N)x comprises modified and unmodified ribonucleotides, each modified ribonucleotide having a 2'-O-methyl on its sugar, wherein N at the 3' terminus of (N)x is a modified ribonucleotide, (N)x comprises at least five alternating modified ribonucleotides beginning at the 3' end and at least nine modified ribonucleotides in total and each remaining N is an unmodified ribonucleotide.

In some embodiments at least one of (N)x and (N')y comprises at least one mirror nucleotide. In some embodiments in (N')y at least one unconventional moiety is present, which unconventional moiety may be an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond, or any other unconventional moiety disclosed herein.

In some embodiments an unconventional moiety is an L-DNA mirror nucleotide; in additional embodiments at least one unconventional moiety is present at positions 15, 16, 17, or 18 in (N')y. In some embodiments the unconventional moiety is selected from a mirror nucleotide, an abasic ribose moiety and an abasic deoxyribose moiety. In some embodiments the unconventional moiety is a mirror nucleotide, preferably an L-DNA moiety. In some embodiments the L-DNA moiety is present at position 17, position 18 or positions 17 and 18.

In yet other embodiments (N')y comprises at least five abasic ribose moieties or abasic deoxyribose moieties and at least one of N' is an LNA.

In some embodiments (N)x comprises nine alternating modified ribonucleotides. In other embodiments (N)x comprises nine alternating modified ribonucleotides further comprising a 2' modified nucleotide at position 2. In some embodiments (N)x comprises 2'OMe modified ribonucleotides at the odd numbered positions 1, 3, 5, 7, 9, 11, 13, 15, 17, 19. In other embodiments (N)x further comprises a 2'OMe modified ribonucleotide at one or both of positions 2 and 18. In yet other embodiments (N)x comprises 2'OMe modified ribonucleotides at positions 2, 4, 6, 8, 11, 13, 15, 17, 19. In some embodiments at least one pyrimidine nucleotide in (N)x comprises a 2'OMe sugar modification. In some embodiments all pyrimidine nucleotides in (N)x comprises a 2'OMe sugar modification. In some embodiments 2, 3, 4, 5, 6, 7, 8, 9, 1'0, 11, 12, 13, 14, or 15 pyrimidine nucleotides in N(x) comprise a 2'OMe sugar modification In various embodiments z'' is present and is selected from an abasic ribose moiety, a deoxyribose moiety; an inverted abasic ribose moiety, a deoxyribose moiety; C6-amino-Pi; a mirror nucleotide.

In one embodiment of the nucleic acid molecules (N')y comprises at least two nucleotides at either or both the 5' and 3' termini of (N')y are joined by a 2'-5' phosphodiester bond. In certain embodiments x=y=19; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and three nucleotides at the 3' terminus of (N')y are joined by two 2'-5' phosphodiester bonds. In other embodiments, x=y=19; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; and four consecutive nucleotides at the 5' terminus of (N')y are joined by three 2'-5' phosphodiester bonds. In a further embodiment, an additional nucleotide located in the middle position of (N)y may be modified with 2'-O-methyl on its sugar. In another embodiment, in (N)x the nucleotides alternate between 2'-O-methyl modified ribonucleotides and unmodified ribonucleotides, and in (N')y four consecutive nucleotides at the 5' terminus are joined by three 2'-5' phosphodiester bonds and the 5' terminal nucleotide or two or three consecutive nucleotides at the 5' terminus comprise 3'-O-Me sugar modifications.

In certain embodiments of Structure (A1), x=y=19 and in (N')y the nucleotide in at least one position comprises a mirror nucleotide, a deoxyribonucleotide and a nucleotide joined to an adjacent nucleotide by a 2'-5' internucleotide bond.

In certain embodiments of Structure (A1), x=y=19 and (N')y comprises a mirror nucleotide. In various embodiments the mirror nucleotide is an L-DNA nucleotide. In certain embodiments the L-DNA is L-deoxyribocytidine. In some embodiments (N')y comprises L-DNA at position 18. In other embodiments (N')y comprises L-DNA at positions 17 and 18. In certain embodiments (N')y comprises L-DNA substitutions at positions 2 and at one or both of positions 17 and 18. Other embodiments of Structure (A1) are envisaged in wherein x=y=21 or wherein x=y=23; in these embodiments the modifications for (N')y discussed above instead of being on positions 15, 16, 17, 18 are on positions 17, 18, 19, 20 for 21 mer and on positions 19, 20, 21, 22 for 23 mer; similarly the modifications at one or both of positions 17 and 18 are on one or both of positions 19 or 20 for the 21 mer and one or both of positions 21 and 22 for the 23 mer. All modifications in the 19 mer are similarly adjusted for the 21 and 23 mers.

According to various embodiments of Structure A1 or A2 in 2, 3, 4, 5, 6, 7, 8, 9, 10, 11, 12, 13 or 14 consecutive ribonucleotides at the 3' terminus in (N')y or N2-(N')y are linked by 2'-5' internucleotide linkages. In one embodiment, four consecutive nucleotides at the 3' terminus of (N')y are joined by three 2'-5' phosphodiester bonds, wherein one or more of the 2'-5' nucleotides which form the 2'-5' phosphodiester bonds further comprises a 3'-O-methyl sugar modification. Preferably the 3' terminal nucleotide of (N')y comprises a 2'-O-methyl sugar modification. In certain embodiments of Structure (A1), x=y=19 and in (N')y two or more consecutive nucleotides at positions 15, 16, 17, 18 and 19 comprise a nucleotide joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In some embodiments the nucleotides at positions 17 and 18 in (N')y are joined by a 2'-5' internucleotide bond. In other embodiments the nucleotides at positions 16, 17, 18, 16-17, 17-18, or 16-18 in (N')y are joined by a 2'-5' internucleotide bond.

In certain embodiments (N')y comprises an L-DNA at position 2 and 2'-5' internucleotide bonds at positions 16, 17, 18, 16-17, 17-18, or 16-18. In certain embodiments (N')y comprises 2'-5' internucleotide bonds at positions 16, 17, 18, 16-17, 17-18, or 16-18 and a 5' terminal cap nucleotide.

In one embodiment of the nucleic acid molecules, the 3' terminal nucleotide or two or three consecutive nucleotides at the 3' terminus of (N')y are L-deoxyribonucleotides.

In other embodiments the nucleic acid molecules, in (N')y 2, 3, 4, 5, 6, 7, 8, 9, 10, 11, 12, 13 or 14 consecutive ribonucleotides at either terminus or 2-8 modified nucleotides at each of the 5' and 3' termini are independently 2' sugar modified nucleotides. In some embodiments the 2' sugar modification comprises the presence of an amino, a fluoro, an alkoxy or an alkyl moiety. In certain embodiments the 2' sugar modification comprises a methoxy moiety (2'-OMe).

In one embodiment, three, four or five consecutive nucleotides at the 5' terminus of (N')y comprise the 2'-OMe modification. In another embodiment, three consecutive nucleotides at the 3' terminus of (N')y comprise the 2'-O-Me sugar modification.

In some embodiments of Structure A1 or A2 in (N')y or N2-(N')y 2, 3, 4, 5, 6, 7, 8, 9, 10, 11, 12, 13 or 14 consecutive ribonucleotides at either or 2-8 modified nucleotides at each of the 5' and 3' termini are independently bicyclic nucleotide. In various embodiments the bicyclic nucleotide is a locked nucleic acid (LNA). A 2'-O, 4'-C-ethylene-bridged nucleic acid (ENA) is a species of LNA (see below).

In various embodiments (N')y or N2-(N')y comprises modified nucleotides at the 5' terminus or at both the 3' and 5' termini.

In some embodiments of Structure A1 or A2 at least two nucleotides at either or both the 5' and 3' termini of (N')y are joined by P-ethoxy backbone modifications. In certain embodiments x=y=19 or x=y=23; in (N)x the nucleotides alternate between modified ribonucleotides and unmodified ribonucleotides, each modified ribonucleotide being modified so as to have a 2'-O-methyl on its sugar and the ribonucleotide located at the middle position of (N)x being unmodified; and four consecutive nucleotides at the 3' terminus or at the 5' terminus of (N')y are joined by three P-ethoxy backbone modifications. In another embodiment, three consecutive nucleotides at the 3' terminus or at the 5' terminus of (N')y are joined by two P-ethoxy backbone modifications.

In some embodiments of Structure A1 or A2 in (N')y or N2-(N')y 2, 3, 4, 5, 6, 7 or 8, consecutive ribonucleotides at each of the 5' and 3' termini are independently mirror nucleotides, nucleotides joined by 2'-5' phosphodiester bond, 2' sugar modified nucleotides or bicyclic nucleotide. In one embodiment, the modification at the 5' and 3' termini of (N')y is identical. In one embodiment, four consecutive nucleotides at the 5' terminus of (N')y are joined by three 2'-5' phosphodiester bonds and three consecutive nucleotides at the 3' terminus of (N')y are joined by two 2'-5' phosphodiester bonds. In another embodiment, the modification at the 5' terminus of (N')y is different from the modification at the 3' terminus of (N')y. In one embodiment, the modified nucleotides at the 5' terminus of (N')y are mirror nucleotides and the modified nucleotides at the 3' terminus of (N')y are joined by 2'-5' phosphodiester bond. In another specific embodiment, three consecutive nucleotides at the 5' terminus of (N')y are LNA nucleotides and three consecutive nucleotides at the 3' terminus of (N')y are joined by two 2'-5' phosphodiester bonds. In (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified, or the ribonucleotides in (N)x being unmodified In another embodiment of Structure A1 the invention provides a compound wherein x=y=19; in (N)x the nucleotides alternate between modified ribonucleotides and unmodified ribonucleotides, each modified ribonucleotide being modified so as to have a 2'-O-methyl on its sugar and the ribonucleotide located at the middle of (N)x being unmodified; three nucleotides at the 3' terminus of (N')y are joined by two 2'-5' phosphodiester bonds and three nucleotides at the 5' terminus of (N')y are LNA such as ENA; and Z and/or Z' independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide. In some embodiments Z is selected from C3Pi-C3Pi, C3Pi-C3OH; C3Pi-rAb; C3Pi-dAb; dAb-dAb and rAb-rAb.

In another embodiment five consecutive nucleotides at the 5' terminus of (N')y or N2-(N')y comprise the 2'-O-methyl sugar modification and two consecutive nucleotides at the 3' terminus of (N')y are L-DNA.

According to other embodiments in N')y or N2-(N')y the 5' or 3' terminal nucleotide, or 2, 3, 4, 5 or 6 consecutive nucleotides at either termini or 1-4 modified nucleotides at each of the 5' and 3' termini are independently phosphonocarboxylate or phosphinocarboxylate nucleotides (PACE nucleotides). In some embodiments the PACE nucleotides are deoxyribonucleotides. In some embodiments in N')y or N2-(N')y, 1 or 2 consecutive nucleotides at each of the 5' and 3' termini are PACE nucleotides. Examples of PACE nucleotides and analogs are disclosed in U.S. Pat. Nos. 6,693,187 and 7,067,641 both incorporated by reference.

In one embodiment of Structure (A1), x=y=19; (N)x comprises unmodified ribonucleotides in which two consecutive nucleotides linked by one 2'-5' internucleotide linkage at the 3' terminus; (N')y comprises unmodified ribonucleotides in which two consecutive nucleotides linked by one 2'-5' internucleotide linkage at the 5' terminus; and Z and/or Z' independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide. In some embodiments Z is selected from C3Pi-C3Ps; C3Pi-C3OH; C3Pi-C3Pi; C3Pi-rAb; C3Pi-dAb; dAb-dAb and rAb-rAb, each C3, rAb, dAb covalently linked to the adjacent C3Pi, rAb, dAb via a phospho-based bond. In some embodiments the phospho-based bond is a phosphodiester bond or a phosphorothiophosphate bond.

In some embodiments, x=y=19; (N)x comprises unmodified ribonucleotides in which three consecutive nucleotides at the 3' terminus are joined together by two 2'-5' phosphodiester bonds; (N')y comprises unmodified ribonucleotides in which four consecutive nucleotides at the 5' terminus are joined together by three 2'-5' phosphodiester bonds; and, Z and/or Z' independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide. In some embodiments Z is selected from C3Pi-C3Ps; C3Pi-C3OH; C3Pi-C3Pi; C3Pi-rAb; C3Pi-dAb; dAb-dAb and rAb-rAb wherein each C3Pi, rAb, dAb covalently linked to the adjacent C3Pi, rAb, dAb via a phospho-based bond. In some embodiments the phospho-based bond is a phosphodiester bond or a phosphorothiophosphate bond.

According to one embodiment of Structure A1 or A2 four consecutive nucleotides at the 5' terminus of (N')y or (N')y-N2, respectively are joined by three 2'-5' phosphodiester bonds; three consecutive nucleotides at the 3' terminus of (N')x are joined by two 2'-5' phosphodiester bonds; and Z and/or Z' independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide. In some embodiments Z is selected from C3Pi-C3Ps; C3Pi-C3OH; C3Pi-C3Pi; C3Pi-rAb; C3Pi-dAb; C3-dAb; dAb-dAb and rAb-rAb. Three nucleotides at the 5' terminus of (N')y and two nucleotides at the 3' terminus of (N')x may also comprise 3'-O-Me sugar modifications.

In one embodiment of Structure A1 or A2, five consecutive nucleotides at the 5' terminus of (N')y or (N')y-N2, respectively comprise the 2'-O-Me sugar modification and five consecutive nucleotides at the 3' terminus of (N')x comprise the 2'-O-Me sugar modification. In another embodiment ten consecutive nucleotides at the 5' terminus of (N')y comprise the 2'-O-Me sugar modification and five consecutive nucleotides at the 3' terminus of (N')x comprise the 2'-O-Me sugar modification. In another embodiment thirteen consecutive nucleotides at the 5' terminus of (N')y comprise the 2'-O-Me sugar modification; five consecutive nucleotides at the 3' terminus of (N')x comprise the 2'-O-Me sugar modification; and Z and/or Z' independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide. In some embodiments Z is selected C3Pi-C3Ps; C3Pi-C3OH; C3Pi-C3Pi; C3Pi-rAb; C3Pi-dAb; dAb-dAb and rAb-rAb.

In specific embodiments five consecutive nucleotides at the 5' terminus of (N')y or (N')y-N2, respectively comprise the 2'-O-Me sugar modification and two consecutive nucleotides at the 3' terminus of (N')y are L-DNA. In addition, the compound may further comprise five consecutive 2'-O-methyl modified nucleotides at the 3' terminus of (N')x and Z and/or Z' may independently comprise one or more non-nucleotide moiety selected from the group consisting of an abasic moiety, an inverted abasic moiety, a hydrocarbon moiety, and an inorganic phosphate, or a combination of one or more non-nucleotide moiety and one or more nucleotide. In some embodiments Z is selected from C3Pi-C3Ps; C3Pi-C3OH; C3Pi-C3Pi; C3Pi-rAb; C3Pi-dAb; dAb-dAb and rAb-rAb.

In various embodiments of Structure A1 or A2 the modified nucleotides in (N)x are different from the modified nucleotides in (N')y. For example, the modified nucleotides in (N)x are 2' sugar modified nucleotides and the modified nucleotides in (N')y are nucleotides linked by 2'-5' internucleotide linkages. In another example, the modified nucleotides in (N)x are mirror nucleotides and the modified nucleotides in (N')y are nucleotides linked by 2'-5' internucleotide linkages. In another example, the modified nucleotides in (N)x are nucleotides linked by 2'-5' internucleotide linkages and the modified nucleotides in (N')y are mirror nucleotides.

In some embodiments provided herein is a compound having a structure set forth below:

```
(X1)   5'    (N)x - Z        3' (antisense strand)
       3' Z'-(N')y-z"        5' (sense strand)
``` wherein each of N and N' is a ribonucleotide which may be unmodified or modified, or is an unconventional moiety;
wherein each of (N)x and (N')y is an oligonucleotide in which each consecutive N or N' is joined to the next N or N' by a covalent bond;
wherein Z consists of two non-nucleotide moieties, or a combination of a non-nucleotide moiety and a nucleotide;
wherein Z' may be present or absent but if present comprises one non-nucleotide moiety;
wherein z" may be present or absent but if present is a capping moiety covalently attached at the 5' terminus of (N')y;
wherein each of x and y is independently an integer from 18 to 27;
wherein (N')y comprises at least one mirror nucleotide at the 3' terminus or 3' penultimate position; and
wherein the sequence of (N)x comprises an antisense sequence to a mammalian gene.

In some embodiments x=y=19.

In some embodiments the mirror nucleotides is selected from an L-DNA and an L-RNA moiety. In some embodiments the mirror nucleotide is an L-DNA moiety. In some embodiments either Z or Z' is present and comprises an abasic moiety or hydrocarbon moiety or combination thereof. In some embodiments Z' is absent, Z is present and comprises a hydrophobic moiety.

In some embodiments the mirror nucleotides is selected from an L-DNA and an L-RNA moiety. In some embodiments the mirror nucleotide is an L-DNA moiety.

In some embodiments N'(y) comprises two or 3 mirror nucleotides at the 3' terminus, and N(x) optionally comprises at least one mirror nucleotide at the 3' terminus.

In some embodiments N'(y) comprises two mirror nucleotides at the 3' penultimate position. In some embodiments N(x) comprises one or two mirror nucleotides at the 3' penultimate position and N'(y) optionally further comprises one or two mirror nucleotides at the 5' penultimate position. In some embodiments (N')y comprises one mirror nucleotide at the 5' terminus or 5' penultimate position.

In some embodiments (N)x comprises 2'OMe sugar modified ribonucleotides. In some embodiments (N)x comprises 2'OMe sugar modified pyrimidine ribonucleotides. In some embodiments (N)x comprises 2'OMe sugar modified ribonucleotides alternating with unmodified ribonucleotides. In some embodiments x=y=19 and (N)x comprises 2'OMe sugar modified ribonucleotides in position (5'>3') 3, 5 and 11, 13, 15, 17, and 19. In some embodiments (N)x further comprises a mirror nucleotide or a 2'5' nucleotide in positions 6 or 7.

In some embodiments the sequence of (N)x has complementarity to the sequence of (N')y; and the sequence of (N')y has identity to a sequence within an mRNA encoded by a target gene.

In another embodiment provided herein is a compound having the structure set forth below:

```
(X2)   5' (N)x - Z         3' (antisense strand)
       3' Z'-(N')y-z"      5' (sense strand)
``` wherein each of N and N' is a ribonucleotide which may be unmodified or modified, or is an unconventional moiety;
wherein each of (N)x and (N')y is an oligonucleotide in which each consecutive N or N' is joined to the next N or N' by a covalent bond;

wherein Z consists of two non-nucleotide moieties, or a combination of a non-nucleotide moiety and a nucleotide;
wherein Z' may be present or absent but if present comprises one non-nucleotide moiety;
wherein z" may be present or absent but if present is a capping moiety covalently attached at the 5' terminus of (N')y;
wherein each of x and y is independently an integer from 18 to 27;
wherein (N')y comprises at least one or more 2'OMe modified pyrimidines and
wherein the sequence of (N)x comprises an antisense sequence to a mammalian gene.

In some embodiments x=y=19.

In some embodiments either Z or Z' are present. In some embodiments both Z and Z' are present. In some embodiments Z' is absent, Z is present and comprises a hydrophobic moiety.

In some embodiments (N)x comprises 2'OMe sugar modified ribonucleotides. In some embodiments (N)x comprises 2'OMe sugar modified pyrimidine ribonucleotides. In some embodiments (N)x comprises 2'OMe sugar modified ribonucleotides alternating with unmodified ribonucleotides. In some embodiments x=y=19 and (N)x comprises 2'OMe sugar modified ribonucleotides in position (5'>3') 3, 5 and 11, 13, 15, 17, and 19. In some embodiments (N)x further comprises a mirror nucleotide or a 2'5' nucleotide in positions 6 or 7.

In some embodiments the sequence of (N)x has complementarity to the sequence of (N')y; and the sequence of (N')y has identity to a sequence within an mRNA encoded by a target gene.

In some embodiments provide herein is a compound having a structure set forth below:

```
(X3)    5'  (N)x - Z         3'  (antisense strand)
        3'  Z'-(N')y-z"      5'  (sense strand)
``` wherein each of N and N' is a ribonucleotide which may be unmodified or modified, or wherein the sequence of (N)x comprises an antisense sequence to a mammalian gene.

In some embodiments x=y=19.

In some embodiments N'(y) comprises 2, 3, 4, 5, 6, 7, or 8 nucleotides joined to an adjacent nucleotide by a 2'-5' internucleotide bond.

In some embodiments either Z or Z' is present and comprises an abasic moiety or hydrocarbon moiety or combination thereof. In some embodiments Z' is absent, Z is present and comprises a hydrophobic moiety.

In some embodiments N'(y) comprises 2, 3, 4, 5, 6, 7, or 8 nucleotides joined to an adjacent nucleotide by a 2'-5' internucleotide bond at the 3' terminus. In some embodiments N'(y) comprises 2, 3, 4, 5, 6, 7, or 8 nucleotides joined to an adjacent nucleotide by a 2'-5' internucleotide bond at the 3' penultimate position. In some embodiments x=y=19 and N'(y) comprises 2, 3, 4, or 5 nucleotides joined to an adjacent nucleotide by a 2'-5' internucleotide bond at the 3' terminus. In some embodiments x=y=19 and N'(y) comprises 5 nucleotides joined to an adjacent nucleotide by a 2'-5' internucleotide bond at the 3' terminus i.e. in position 15, 16, 17, 18 and 19 (5'>3'). In some embodiments (N)x comprises 2'OMe sugar modified ribonucleotides. In some embodiments (N)x comprises 2'OMe sugar modified pyrimidine ribonucleotides. In some embodiments (N)x comprises 2'OMe sugar modified ribonucleotides alternating with unmodified ribonucleotides. In some embodiments x=y=19 and (N)x comprises 2'OMe sugar modified ribonucleotides in position (5'>3') 3, 5 and 11, 13, 15, 17, and 19. In some embodiments (N)x further comprises a mirror nucleotide or a 2'5' nucleotide in positions 6 or 7.

In some embodiments the sequence of (N)x has complementarity to the sequence of (N')y; and the sequence of (N')y has identity to a sequence within an mRNA encoded by a target gene.

In some preferred embodiment nucleic acid molecules disclosed herein have the following structure

```
5'       N N N N N N N N N N N N N N N N N N N-C3Pi-C3OH
3'  HOC3-N'N'N'N'N'N'N'N'N'N'N'N'N'N'N'N'N'N'N'-z"
or

5'       N N N N N N N N N N N N N N N N N N N-C3Pi-C3OH
3'  iPC3-N'N'N'N'N'N'N'N'N'N'N'N'N'N'N'N'N'N'N'-z"
``` an unconventional moiety;
wherein each of (N)x and (N')y is an oligonucleotide in which each consecutive N or N' is joined to the next N or N' by a covalent bond;
wherein Z consists of two non-nucleotide moieties, or a combination of a non-nucleotide moiety and a nucleotide;
wherein Z' may be present or absent but if present comprises one non-nucleotide moiety;
wherein z" may be present or absent but if present is a capping moiety covalently attached at the 5' terminus of (N')y;
wherein each of x and y is independently an integer from 18 to 27;
wherein (N')y comprises at least one nucleotide joined to an adjacent nucleotide by a 2'-5' internucleotide bond; and wherein of N and N' is independently a ribonucleotide which may be unmodified or modified, or is an unconventional moiety;
wherein each N is linked to the adjacent N by a covalent bond;
wherein each N' is linked to the adjacent N' by a covalent bond;
wherein 1 to 10 of N are 2'-O Me sugar modified ribonucleotides;
wherein N at position 5, 6, 7, 8 or 9 (5'>3') is a 2'5 nucleotide or a mirror nucleotide;
wherein N' at positions 15-19 (5'>3') are 2'5' ribonucleotides;
wherein z" is a capping moiety covalently attached to the 5' terminus of the sense strand.

In some preferred embodiment nucleic acid molecules disclosed herein have the following structure

```
5'       N N N N N N N N N N N N N N N N N N N-C3Pi-C3OH
3'  HOC3-N'N'N'N'N'N'N'N'N'N'N'N'N'N'N'N'N'N'N'-z"
or
```

```
5'        N N N N N N N N N N N N N N N N N-C3Pi-C3OH
3'  iPC3-N'N'N'N'N'N'N'N'N'N'N'N'N'N'N'N'N'N'-z"
``` wherein of N and N' is independently a ribonucleotide which may be unmodified or modified, or is an unconventional moiety;

wherein each N is linked to the adjacent N by a covalent bond;

wherein each N' is linked to the adjacent N' by a covalent bond;

wherein 1 to 10 of N are 2'-O Me sugar modified ribonucleotides;

wherein N at position 5, 6, 7, 8 or 9 (5'>3') is a 2'5 nucleotide or a mirror nucleotide;

wherein N' comprises one or more 2'-O Me sugar modified pyrimidine ribonucleotides;

wherein N at position 9 or 10 (5'>3') is a 2'5 nucleotide; and wherein z" is a capping moiety covalently attached to the 5' terminus of the sense strand.

In some embodiments of Structures (X1-X3), either the sense strand or the antisense strand or both the sense and the antisense strands comprise one or two inorganic phosphate moieties at the at the 3' termini.

In some embodiments of Structures (X1-X3) in (N)x the N at the 3' terminus is a modified ribonucleotide and (N)x comprises at least 8 modified ribonucleotides. In some embodiments the modified ribonucleotides comprise 2' OMe sugar modified ribonucleotides. In other embodiments at least 5 of the at least 8 modified ribonucleotides are alternating beginning at the 3' end.

In various embodiments of Structures (X1-X3) z" is present and is selected from an abasic ribose moiety, a deoxyribose moiety; an inverted abasic ribose moiety, a deoxyribose moiety; C6-amino-Pi; a mirror nucleotide.

In various embodiments of Structures (X1-X3) in (N')y at least one additional unconventional moiety is present, which unconventional moiety may be an abasic ribose moiety, an abasic deoxyribose moiety, a modified or unmodified deoxyribonucleotide, a mirror nucleotide, a non-base pairing nucleotide analog or a nucleotide joined to an adjacent nucleotide by a 2'-5' internucleotide phosphate bond. In some embodiments, neither (N)x nor (N')y are phosphorylated at the 3' and 5' termini. In other embodiments either or both (N)x and (N')y are phosphorylated at the 3' termini. In yet another embodiment, either or both (N)x and (N')y are phosphorylated at the 3' termini using non-cleavable phosphate groups. In yet another embodiment, either or both (N)x and (N')y are phosphorylated at the terminal 2' termini position using cleavable or non-cleavable phosphate groups.

In certain embodiments for all of the above-mentioned structures, Z is present. In other embodiments Z' is present. In additional embodiments both Z and Z' are present. In some embodiments Z and Z' are both present and identical. In further embodiments both Z and Z' are present and are different. In some embodiments Z and Z' are independently 1, 2, 3, 4 or 5 non-nucleotide moieties, or a combination of a non-nucleotide moiety and a nucleotide.

In some embodiments Z is present and comprises one or more non-nucleotide moiety selected from an abasic moiety, an inverted abasic moiety, a hydrocarbon moiety such as (CH2)3, and an inorganic phosphate moiety.

In additional embodiments Z' is present and comprises one or more non-nucleotide moiety selected from an abasic moiety, an inverted abasic moiety, a hydrocarbon moiety such as (CH2)3, and an inorganic phosphate moiety.

In some embodiments each of Z and/or Z' comprises one or two non-nucleotide moieties and further comprises a nucleotide.

In some embodiments Z and/or Z' comprise abasic moieties, optionally deoxyribo-abasic (referred to herein as "dAb") or riboabasic (referred to herein as "rAb") moieties. In some embodiments each of Z and/or Z' is dAb-dAb or rAb-rAb.

In some embodiments Z and/or Z' comprise one or more hydrocarbon moieties, optionally (CH2)-3-Pi (referred to herein as "C3Pi"). In some embodiments Z and/or Z' is C3Pi-C3Ps; C3Pi-C3OH; or C3Pi-C3Pi.

In additional embodiments Z and/or Z' comprise a combination of abasic moieties and unmodified nucleotides or a combination of hydrocarbon modified moieties and unmodified nucleotides or a combination of abasic moieties and hydrocarbon modified moieties. In such embodiments, Z and/or Z' are optionally C3Pi-rAb. In a particular embodiment only Z is present and is C3Pi-C3Ps; C3Pi-C3OH; C3Pi-C3Pi.

In the embodiments of the above-mentioned Structures, the compound comprises at least one 3' overhang (Z and or Z') comprising at least one non-nucleotide moiety. Z and Z' independently comprises one non-nucleotide moiety and one or more covalently linked modified or non-modified nucleotides or unconventional moiety, for example inverted dT or dA; dT, LNA, mirror nucleotide and the like. The siRNA in which Z and/or Z' is present has improved activity and/or stability and/or off-target activity and or reduced immune response when compared to an siRNA in which Z and/or Z' are absent or in which Z and/or Z' is dTdT.

In certain embodiments for all the above-mentioned Structures, the compound comprises one or more phosphonocarboxylate and/or phosphinocarboxylate nucleotides (PACE nucleotides). In some embodiments the PACE nucleotides are deoxyribonucleotides and the phosphinocarboxylate nucleotides are phosphinoacetate nucleotides. Examples of PACE nucleotides and analogs are disclosed in U.S. Pat. Nos. 6,693,187 and 7,067,641, both incorporated herein by reference.

In certain embodiments for all the above-mentioned Structures, the compound comprises one or more locked nucleic acids (LNA) also defined as bridged nucleic acids or bicyclic nucleotides. Exemplary locked nucleic acids include 2'-O, 4'-C-ethylene nucleosides (ENA) or 2'-O, 4'-C-methylene nucleosides. Other examples of LNA and ENA nucleotides are disclosed in WO 98/39352, WO 00/47599 and WO 99/14226, all incorporated herein by reference.

In certain embodiments for all the above-mentioned Structures, the compound comprises one or more altritol monomers (nucleotides), also defined as 1,5 anhydro-2-deoxy-D-altrito-hexitol (see for example, Allart, et al., 1998. Nucleosides & Nucleotides 17:1523-1526; Herdewijn et al., 1999. Nucleosides & Nucleotides 18:1371-1376; Fisher et al., 2007, NAR 35(4):1064-1074; all incorporated herein by reference).

The present invention explicitly excludes double stranded compounds in which each of N and/or N' is a deoxyribonucleotide (dA, dC, dG, dT). In certain embodiments (N)x and (N')y may comprise independently 1, 2, 3, 4, 5, 6, 7, 8, 9 or more deoxyribonucleotides. In certain embodiments the provided herein a compound wherein each of N is an unmodified ribonucleotide and the 3' terminal nucleotide or 2, 3, 4, 5, 6, 7, 8, 9, 10, 11, 12, 13 or 14 consecutive nucleotides at the 3' terminus of (N')y are deoxyribonucleotides. In yet other embodiments each of N is an unmodified ribonucleotide and the 5' terminal nucleotide or 2, 3, 4, 5, 6, 7, 8, 9, 10, 11, 12, 13 or 14 consecutive nucleotides at the 5' terminus of (N')y are deoxyribonucleotides. In further embodiments the 5' terminal nucleotide or 2, 3, 4, 5, 6, 7, 8, or 9 consecutive nucleotides at the 5' terminus and 1, 2, 3, 4, 5, or 6 consecutive nucleotides at the 3' termini of (N)x are deoxyribonucleotides and each of N' is an unmodified ribonucleotide. In yet further embodiments (N)x comprises unmodified ribonucleotides and 1 or 2, 3 or 4 consecutive deoxyribonucleotides independently at each of the 5' and 3' termini and 1 or 2, 3, 4, 5 or 6 consecutive deoxyribonucleotides in internal positions; and each of N' is an unmodified ribonucleotide. In certain embodiments the 3' terminal nucleotide or 2, 3, 4, 5, 6, 7, 8, 9, 10, 11, 12, 13 or 14 consecutive nucleotides at the 3' terminus of (N')y and the terminal 5' nucleotide or 2, 3, 4, 5, 6, 7, 8, 9, 10, 11, 12, 13 or 14 consecutive nucleotides at the 5' terminus of (N)x are deoxyribonucleotides. In some embodiments the 5' terminal nucleotide of N or 2 or 3 consecutive of N and 1, 2, or 3 of N' is a deoxyribonucleotide. Certain examples of active DNA/RNA siRNA chimeras are disclosed in US patent publication 2005/0004064, and Ui-Tei, 2008 (NAR 36(7):2136-2151) incorporated herein by reference in their entirety.

A covalent bond refers to an internucleotide linkage linking one nucleotide monomer to an adjacent nucleotide monomer. A covalent bond includes for example, a phosphodiester bond, a phosphorothioate bond, a P-alkoxy bond, a P-carboxy bond and the like. The normal internucleoside linkage of RNA and DNA is a 3' to 5' phosphodiester linkage. In certain embodiments a covalent bond is a phosphodiester bond. Covalent bond encompasses non-phosphorous-containing internucleoside linkages, such as those disclosed in WO 2004/041924 inter alia. Unless otherwise indicated, in embodiments of the structures discussed herein the covalent bond between each consecutive N or N' is a phosphodiester bond.

For all of the structures above, in some embodiments the oligonucleotide sequence of (N)x is fully complementary to the oligonucleotide sequence of (N')y. In other embodiments (N)x and (N')y are substantially complementary. In certain embodiments (N)x is fully complementary to a target sequence. In other embodiments (N)x is substantially complementary to a target sequence.

DEFINITIONS

For convenience certain terms employed in the specification, examples and claims are described herein.

It is to be noted that, as used herein, the singular forms "a", "an" and "the" include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

What is referred to herein as the "sense" or "sense strand" or "passenger strand" of a double stranded or duplex siRNA compound, refers to an oligonucleotide having identity to a target nucleic acid, for example target RNA including target mRNA. What is referred to herein as the "antisense" or "antisense strand" or "guide strand" refers to an oligonucleotide having complementarity to a target nucleic acid, for example target mRNA. Without wishing to be bound to theory, the antisense, or guide strand, is incorporated into the RNA-induced silencing complex (RISC) and directs post-transcriptional gene silencing, which occurs when the guide strand base pairs with a complementary sequence of a messenger RNA molecule and mediates cleavage of the mRNA by Argonaute, the catalytic component of RISC complex.

A "pro-apoptotic polypeptide" refers to a polypeptide encoded by any of the above listed genes, including splice variants, isoforms, orthologs, or paralogs and the like.

An "inhibitor" is a compound which is capable of reducing the expression of a gene or the activity of the product of such gene to an extent sufficient to achieve a desired biological or physiological effect. The term "inhibitor" as used herein refers to one or more of an oligonucleotide inhibitor, including siRNA, shRNA, miRNA and ribozymes. Inhibition may also be referred to as down-regulation or, for RNAi, silencing.

The term "inhibit" as used herein refers to reducing the expression of a gene or the activity of the product of such gene to an extent sufficient to achieve a desired biological or physiological effect. Inhibition may be complete or partial.

As used herein, the terms "polynucleotide" and "nucleic acid" may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs. Throughout this application mRNA sequences are set forth as representing the target of their corresponding genes. The terms "mRNA polynucleotide sequence" and mRNA are used interchangeably.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds disclosed herein encompass molecules comprising deoxyribonucleotides, ribonucleotides, modified deoxyribonucleotides, modified ribonucleotides and combinations thereof. As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide.

Provided herein are methods and compositions for inhibiting expression of a target gene in vivo. In general, the method includes administering oligoribonucleotides, in particular small interfering RNAs (i.e., siRNAs) or a nucleic acid material that generates siRNA in a cell, to target a mammalian mRNA in an amount sufficient to down-regulate expression of a target gene by an RNA interference mechanism. In particular, the method is useful for inhibiting expression of the gene for treatment of a subject suffering from a disease related to expression of that gene. As disclosed herein the siRNA molecules or inhibitors of the target gene are used as drugs to treat various pathologies.

"siRNA compound" and "nucleic acid molecule" may be used interchangeably herein.

"Nucleotide" is meant to encompass a compound consisting of a nucleoside (a sugar, usually ribose or deoxyribose, and a purine or pyrimidine base) and a phospho linker; such as a deoxyribonucleotide and a ribonucleotide, which may be natural or synthetic, and be modified or unmodified. Modifications include changes and substitutions to the sugar moiety, the base moiety and/or the internucleotide linkages.

A "phosphate based" moiety includes inorganic phosphate (Pi) and phosphorothioate (Ps).

All analogs of, or modifications to, a nucleotide/oligonucleotide may be employed with the molecules disclosed herein, provided that said analog or modification does not substantially adversely affect the function of the nucleotide/ oligonucleotide. Acceptable modifications include modifications of the sugar moiety, modifications of the base moiety, modifications in the internucleotide linkages and combinations thereof.

What is sometimes referred to as an "abasic nucleotide" or "abasic nucleotide analog" is more properly referred to as a pseudo-nucleotide or an unconventional moiety. A nucleotide is a monomeric unit of nucleic acid, consisting of a ribose or deoxyribose sugar, a phosphate, and a base (adenine, guanine, thymine, or cytosine in DNA; adenine, guanine, uracil, or cytosine in RNA). A modified nucleotide comprises a modification in one or more of the sugar, phosphate and or base. The abasic pseudo-nucleotide lacks a base, and thus is not strictly a nucleotide. Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyabasic 5'-phosphate. In general, an inverted abasic moiety is covalently attached to a 3' terminal nucleotide via a 3'-3' linkage; an inverted abasic moiety is covalently attached to a 5' terminal nucleotide via a 5'-5' linkage; an inverted abasic moiety is generally covalently attached to an inverted abasic moiety via a 5'-3' linkage.

The term "capping moiety" (z") as used herein includes a moiety which can be covalently linked to the 5' terminus of (N')y and includes abasic ribose moiety, abasic deoxyribose moiety, modified abasic ribose and abasic deoxyribose moieties including 2' O alkyl modifications; inverted abasic ribose and abasic deoxyribose moieties and modifications thereof C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain capping moieties are abasic ribose or abasic deoxyribose moieties; inverted abasic ribose or abasic deoxyribose moieties; C6-amino-Pi; a mirror nucleotide including L-DNA and L-RNA. The compounds of the present invention may be synthesized using one or more inverted nucleotides, for example inverted thymidine or inverted adenine (for example see Takei, et al., 2002. JBC 277(26):23800-06.

The term "non-nucleotide moiety" refers to a moiety that is not a nucleotide, i.e. does not include all of the components of a nucleotide: a sugar, a base and a linker The term "unconventional moiety" as used herein refers to the non-nucleotide moieties including an abasic moiety, an inverted abasic moiety, a hydrocarbon (alkyl) moiety, and an inorganic phosphate and further includes a deoxyribonucleotide, a modified deoxyribonucleotide, a mirror nucleotide (L-DNA or L-RNA), a non-base pairing nucleotide analog and a nucleotide joined to an adjacent nucleotide by a 2'-5' internucleotide phosphate bond (also known as 2'5' nucleotide); bridged nucleic acids including LNA and ethylene bridged nucleic acids, linkage modified (e.g. PACE) and base modified nucleotides as well as additional moieties explicitly disclosed herein as unconventional moieties.

When used in reference to the overhangs, an "alkyl moiety" or a "hydrocarbon moiety" refers to a C2, C3, C4, C5 or C6 straight chain or branched alkyl moiety, including for example C2 (ethyl), C3 (propyl). When used in reference to the overhangs, a "derivative" of an alkyl or a hydrocarbon moiety refers to a C2, C3, C4, C5 or C6 straight chain or branched alkyl moiety comprising a functional group which may be selected from among, inter alia, alcohols, phosphodiester, phosphorothioate, phosphonoacetate, amines, carboxylic acids, esters, amides and aldehydes.

When used in reference to modification of the ribose or deoxyribose moiety, "alkyl" is intended to include linear, branched, or cyclic saturated hydrocarbon structures and combinations thereof "Lower alkyl", when used in reference to modification of the ribose or deoxyribose moiety, refers specifically to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic saturated hydrocarbon groups of from 3 to 8 carbon atoms. Examples of cycloalkyl groups include c-propyl, c-butyl, c-pentyl, norbornyl, adamantyl and the like "Terminal functional group" includes halogen, alcohol, amine, carboxylic, ester, amide, aldehyde, ketone, ether groups.

In the context of the present invention, a "mirror" nucleotide (also referred to as a spiegelmer) is a nucleotide analog with reverse chirality to the naturally occurring or commonly employed nucleotide, i.e., a mirror image of the naturally occurring or commonly employed nucleotide. The mirror nucleotide is a ribonucleotide (L-RNA) or a deoxyribonucleotide (L-DNA) and may further comprise at least one sugar or base modification and/or a backbone modification, such as a phosphorothioate or phosphonate moiety. U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate.

Unconventional moieties include bridged nucleic acids including LNA (2'-O,4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged Nucleic Acid adenosine 3' monophosphate, 2'-O,4'-C-ethylene bridged Nucleic Acid 5-methyl-cytidine 3' monophosphate, 2'-O,4'-C-ethylene bridged Nucleic Acid guanosine 3' monophosphate, 5-methyl-uridine (or thymidine) 3' monophosphate).

In some embodiments of the invention the unconventional moiety is an abasic ribose moiety, an abasic deoxyribose moiety, a deoxyribonucleotide, a mirror nucleotide, and a nucleotide joined to an adjacent nucleotide by a 2'-5' internucleotide phosphate bond.

The nucleotides are selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine. siRNA compounds comprising one or more abasic pseudo-nucleotides are encompassed by the present invention. A nucleotide monomer comprising a modified base, including abasic pseudo-nucleotide monomers, may be substituted for one or more ribonucleotides of the oligonucleotide. An abasic pseudo-nucleotide monomer may be included at the one or more of the terminal positions or as a 5' terminal cap. A 5' terminal cap may also be selected from an inverted abasic pseudo-nucleotide analog, an L-DNA nucleotide, and a C6-imine phosphate.

In addition, analogues of polynucleotides are prepared wherein the structure of one or more nucleotide is fundamentally altered and better suited as therapeutic or experimental reagents. An example of a nucleotide analog is a peptide nucleic acid (PNA) wherein the deoxyribose (or ribose) phosphate backbone in DNA (or RNA comprises with a polyamide backbone which is similar to that found in peptides. PNA analogs have been shown to be resistant to enzymatic degradation and to have extended lives in vivo and in vitro.

Possible modifications to the sugar residue are manifold and include 2'-O alkyl, 2'-halo (e.g. 2' deoxy fluoro), locked nucleic acid (LNA), glycol nucleic acid (GNA), threose nucleic acid (TNA), arabinoside; altritol (ANA) and other 6-membered sugars including morpholinos, and cyclohexinyls. Possible modifications on the 2' moiety of the sugar residue include amino, fluoro, methoxy alkoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1. One or more deoxyribonucleotides are also tolerated in the compounds of the present invention. In some embodiments (N') comprises 1, 2, 3, 4, 5, 6, 7, 8, 9 or 10 DNA moieties.

LNA compounds are disclosed in International Patent Publication Nos. WO 00/47599, WO 99/14226, and WO 98/39352. Examples of siRNA compounds comprising LNA nucleotides are disclosed in Elmen et al., (NAR 2005. 33(1): 439-447) and in International Patent Publication No. WO 2004/083430. Six-membered ring nucleotide analogs are disclosed in Allart, et al (Nucleosides & Nucleotides, 1998, 17:1523-1526; and Perez-Perez, et al., 1996, Bioorg. and Medicinal Chem Letters 6:1457-1460) Oligonucleotides comprising 6-membered ring nucleotide analogs including hexitol and altritol nucleotide monomers are disclosed in International patent application publication No. WO 2006/047842.

Backbone modifications, also known as internucleotide linkage modifications, such as ethyl (resulting in a phospho-ethyl triester); propyl (resulting in a phospho-propyl triester); and butyl (resulting in a phospho-butyl triester) are also possible. Other backbone modifications include polymer backbones, cyclic backbones, acyclic backbones, thiophosphate-D-ribose backbones, amidates, phosphonoacetate derivatives. Certain structures include siRNA compounds having one or a plurality of 2'-5' internucleotide linkages (bridges or backbone).

In some embodiments, neither (N)x nor (N')y are phosphorylated at the 3' and 5' termini. In other embodiments either or both (N)x and (N')y are phosphorylated at the 3' termini (3' Pi). In yet another embodiment, either or both (N)x and (N')y are phosphorylated at the 3' termini with non-cleavable phosphate groups. In yet another embodiment, either or both (N)x and (N')y are phosphorylated at the terminal 2' termini position using cleavable or non-cleavable phosphate groups. Further, the inhibitory nucleic acid molecules of the present invention may comprise one or more gaps and/or one or more nicks and/or one or more mismatches. Without wishing to be bound by theory, gaps, nicks and mismatches have the advantage of partially destabilizing the nucleic acid/siRNA, so that it may be more easily processed by endogenous cellular machinery such as DICER, DROSHA or RISC into its inhibitory components.

In the context of the present invention, a gap in a nucleic acid refers to the absence of one or more internal nucleotides in one strand, while a nick in a nucleic acid refers to the absence of an internucleotide linkage between two adjacent nucleotides in one strand. Any of the molecules of the present invention may contain one or more gaps and/or one or more nicks.

Oligonucleotides

In a non-limiting example, Tables B (B1-B74), Tables C(C1-C4) and Tables D (D1-D34) of PCT Patent Application Publication No. WO 2009/044392, assigned to the assignee of the present invention and incorporated by reference in its entirety, comprise nucleic acid sequences of sense and corresponding antisense oligomers, useful in preparing siRNA compounds according to the present application. The compounds are used as chemically and or structurally modified compounds.

The selection and synthesis of siRNA corresponding to known genes has been widely reported; see for example Ui-Tei et al., J Biomed Biotechnol. 2006; 65052; Chalk et al., BBRC. 2004, 319(1):264-74; Sioud & Leirdal, Met. Mol. Biol. 2004, 252:457-69; Levenkova et al., Bioinform. 2004, 20(3):430-2; Ui-Tei et al., NAR. 2004, 32(3):936-48. For examples of the use and production of modified siRNA see for example Braasch et al., Biochem. 2003, 42(26):7967-75; Chiu et al., RNA. 2003, 9(9):1034-48; PCT Publication Nos. WO 2004/015107 and WO 02/44321 and U.S. Pat. Nos. 5,898,031 and 6,107,094.

The present invention provides double-stranded oligonucleotides (e.g. siRNAs), which down-regulate the expression of a desired gene. A siRNA of the invention is a duplex oligoribonucleotide in which the sense strand is derived from the mRNA sequence of the desired gene, and the antisense strand is at least substantially complementary to the sense strand. In general, some deviation from the target mRNA sequence is tolerated without compromising the siRNA activity (see e.g. Czauderna et al., NAR. 2003, 31(11):2705-2716). An siRNA of the invention inhibits gene expression on a post-transcriptional level with or without destroying the mRNA. Without being bound by theory, siRNA may target the mRNA for specific cleavage and degradation and/or may inhibit translation from the targeted message.

In other embodiments at least one of the two strands may have an overhang of at least one nucleotide at the 5'-terminus; the overhang may consist of at least one deoxyribonucleotide. The length of RNA duplex is from about 16 to about 40 ribonucleotides, preferably 19 ribonucleotides. Further, the length of each strand may independently have a length selected from the group consisting of about 16 to about 40 bases, preferably 18 to 23 bases and more preferably 19 ribonucleotides.

In certain embodiments the complementarity between said first strand and the target nucleic acid is perfect. In some embodiments, the strands are substantially complementary, i.e. having one, two or up to five mismatches between said first strand and the target mRNA or between the first and the second strands. Substantially complementary refers to complementarity of greater than about 70%, and less than 100% to another sequence. For example in a duplex region consisting of 19 base pairs one mismatch results in 94.7% complementarity, two mismatches results in about 89.5% complementarity, 3 mismatches results in about 84.2% complementarity, 4 mismatches results in about 79% complementarity and 5 mismatches results in about 74% complementarity, rendering the duplex region substantially complementary. Accordingly, substantially identical refers to identity of greater than about 70%, to another sequence.

The first strand and the second strand may be linked by a loop structure, which may be comprised of a non-nucleic acid polymer such as, inter alia, polyethylene glycol. Alternatively, the loop structure may be comprised of a nucleic acid, including modified and non-modified ribonucleotides and modified and non-modified deoxyribonucleotides.

Further, the 5'-terminus of the first strand of the siRNA may be linked to the 3'-terminus of the second strand, or the 3'-terminus of the first strand may be linked to the 5'-terminus of the second strand, said linkage being via a nucleic acid linker typically having a length between 2-100 nucleobases, preferably about 2 to about 30 nucleobases.

In some embodiments of the compounds of the invention having alternating ribonucleotides modified in at least one of the antisense and the sense strands of the compound, for 19 mer and 23 mer oligomers the ribonucleotides at the 5' and 3' termini of the antisense strand are modified in their sugar residues, and the ribonucleotides at the 5' and 3' termini of the sense strand are unmodified in their sugar residues. For 21 mer oligomers the ribonucleotides at the 5' and 3' termini of the sense strand are modified in their sugar residues, and the ribonucleotides at the 5' and 3' termini of the antisense strand are unmodified in their sugar residues, or may have an optional additional modification at the 3' terminus. As mentioned above, in some embodiments the middle nucleotide of the antisense strand is unmodified.

According to one embodiment of the invention, the antisense and the sense strands of the oligonucleotide/siRNA are phosphorylated only at the 3'-terminus and not at the 5'-terminus. According to another embodiment of the invention, the antisense and the sense strands are non-phosphorylated. According to yet another embodiment of the invention, the 5' most ribonucleotide in the sense strand is modified to abolish any possibility of in vivo 5'-phosphorylation.

Any siRNA sequence disclosed herein are prepared having any of the modifications/structures disclosed herein. The combination of sequence plus structure is novel and is useful used in the treatment of the conditions disclosed herein.

Pharmaceutical Compositions

While it may be possible for the compounds of the present invention to be administered as the raw chemical, it is preferable to present them as a pharmaceutical composition. Accordingly the present invention provides a pharmaceutical composition comprising one or more of the compounds of the invention; and a pharmaceutically acceptable carrier. This composition may comprise a mixture of two or more different oligonucleotides/siRNAs.

The invention further provides a pharmaceutical composition comprising at least one compound of the invention covalently or non-covalently bound to one or more compounds of the invention in an amount effective to inhibit one or more genes as disclosed above; and a pharmaceutically acceptable carrier. The compound may be processed intracellularly by endogenous cellular complexes to produce one or more oligoribonucleotides of the invention.

The invention further provides a pharmaceutical composition comprising a pharmaceutically acceptable carrier and one or more of the compounds of the invention in an amount effective to down-regulate expression in a cell of a target RNA, including target genes and target mRNA, and or target protein, the compound comprising a sequence having complementarity to the sequence of (N)x. In certain embodiments, the target gene is a viral, bacterial or mammalian gene. In various embodiments the target gene is a mammalian gene, preferably a human gene.

Additionally, the invention provides a method of inhibiting the expression of a target gene, by at least 50% as compared to a control, comprising contacting an mRNA transcript of the target gene with one or more of the compounds of the invention. In some embodiments an active siRNA compound inhibits gene expression at a level of at least 50%, 60% or 70% as compared to control. In certain embodiments inhibition is at a level of at least 75%, 80% or 90% as compared to control. In some embodiments the target gene is a pro-apoptotic gene as disclosed herein.

In one embodiment the oligoribonucleotide is inhibiting one or more of the pro-apoptotic genes of the present invention, whereby the inhibition is selected from the group comprising inhibition of gene function, inhibition of polypeptide and inhibition of mRNA expression.

In one embodiment the compound inhibits expression of a polypeptide encoded by a target gene whereby the inhibition is selected from the group comprising inhibition of function (which may be examined by an enzymatic assay or a binding assay with a known interactor of the native gene/polypeptide, inter alia), inhibition of protein (which may be examined by Western blotting, ELISA or immuno-precipitation, inter alia) and inhibition of mRNA expression (which may be examined by Northern blotting, quantitative RT-PCR, in-situ hybridisation or microarray hybridisation, inter alia).

In additional embodiments the invention provides a method of treating a subject suffering from a disease accompanied by an elevated level of the pro-apoptotic genes of the present invention, the method comprising administering to the subject a compound of the invention in a therapeutically effective dose thereby treating the subject.

Delivery

In some embodiments the siRNA molecules of the present invention are delivered to the target tissue by direct application of the naked molecules prepared with a carrier or a diluent.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

However, in some embodiments the siRNA molecules of the invention are delivered in liposome or lipofectin formulations and the like and are prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003. 327: 761-766; Lewis et al., Nat. Gen. 2002, 32: 107-108 and Simeoni et al., NAR 2003, 31, 11: 2717-2724). siRNA has recently been successfully used for inhibition of gene expression in primates (see for example, Tolentino et al., Retina 24(4):660.

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations may be selected. The siRNAs or pharmaceutical compositions of the present invention are administered and dosed in accordance with good medical practice, taking into account the clinical condition of the individual patient, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

In general, Dosage may be from 0.01 mg to 1 g per kg of body weight (e.g., 0.1 mg, 0.25 mg, 0.5 mg, 0.75 mg, 1 mg, 2.5 mg, 5 mg, 10 mg, 25 mg, 50 mg, 100 mg, 250 mg, 500 mg, 1 mg, 2.5 mg, 5 mg, 10 mg, 25 mg, 50 mg, 100 mg, 250 mg, or 500 mg per kg).

A suitable dosage unit of nucleic acid molecules may be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day.

Suitable amounts of nucleic acid molecules may be administered and these amounts can be empirically determined using standard methods. Effective concentrations of individual nucleic acid molecule species in the environment of a cell may be about 1 femtomolar (fmolar), about 50 femtomolar, 100 femtomolar, 1 picomolar, 1.5 picomolar, 2.5 picomolar, 5 picomolar, 10 picomolar, 25 picomolar, 50 picomolar, 100 picomolar, 500 picomolar, 1 nanomolar, 2.5 nanomolar, 5 nanomolar, 10 nanomolar, 25 nanomolar, 50 nanomolar, 100 nanomolar, 500 nanomolar, 1 micromolar, 2.5 micromolar, 5 micromolar, 10 micromolar, 100 micromolar or more.

The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Pharmaceutical compositions that include the nucleic acid molecule disclosed herein may be administered once daily, qid, tid, bid, QD, or at any interval and for any duration that is medically appropriate. However, the therapeutic agent may also be dosed in dosage units containing two, three, four, five, six or more sub-doses administered at appropriate intervals throughout the day. In that case, the nucleic acid molecules contained in each sub-dose may be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. The dosage unit may contain a corresponding multiple of the daily dose. The composition can be compounded in such a way that the sum of the multiple units of a nucleic acid together contain a sufficient dose.

Kits and Containers

Also provided are kits, containers and formulations that include a nucleic acid molecule (e.g., an siNA molecule) as provided herein for reducing expression of a target gene for administering the nucleic acid molecule to a subject. In some embodiments a kit includes at least one container and at least one label. Suitable containers include, for example, bottles, vials, syringes, and test tubes. The containers can be formed from a variety of materials such as glass, metal or plastic. Kits may further include associated indications and/or directions; reagents and other compositions or tools used for such purpose can also be included.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be a nucleic acid molecule capable of specifically binding a target gene and/or modulating the function of a target gene.

A kit may further include a second container that includes a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

The units dosage ampoules or multidose containers, in which the nucleic acid molecules are packaged prior to use, may include an hermetically sealed container enclosing an amount of nucleic acid molecules or solution containing nucleic acid molecules suitable for a pharmaceutically effective dose thereof, or multiples of an effective dose. The nucleic acid molecules are packaged as a sterile formulation, and the hermetically sealed container is designed to preserve sterility of the formulation until use.

The container comprising the nucleic acid molecules may include a package that is labeled, and the label may bear a notice in the form prescribed by a governmental agency, for example the Food and Drug Administration, which notice is reflective of approval by the agency under Federal law, of the manufacture, use, or sale of the polynucleotide material therein for human administration.

Federal or National law requires that the use of pharmaceutical compositions in the therapy of humans be approved by an agency of the Federal or National government. In the United States, enforcement is the responsibility of the Food and Drug Administration, which issues regulations for securing such approval, detailed in 21 U.S.C. §301-392. Similar approval is required by most foreign countries and unique procedures are well known to those in the art and the compositions and methods provided herein preferably comply accordingly.

The dosage to be administered depends to a large extent on the condition and size of the subject being treated as well as the frequency of treatment and the route of administration. Regimens for continuing therapy, including dose and frequency may be guided by the initial response and clinical judgment.

The nucleic acid compounds disclosed herein are administered by any of the conventional routes of administration. It should be noted that the compound is administered as the compound, per se, or as pharmaceutically acceptable salt and is administered alone or as an active ingredient in combination with pharmaceutically acceptable carriers, solvents, diluents, excipients, adjuvants and vehicles. The compounds are administered orally, topically, subcutaneously or parenterally including intravenous, intraarterial, intramuscular, intraperitoneally, and intranasal, inhalation, transtympanic administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, as well as similar pharmaceutical vehicles. In a particular embodiment, the administration comprises intravenous administration. In another embodiment the administration comprises topical or local administration. In some embodiments topical administration includes topical administration to the mammalian ear canal. In some embodiments topical administration includes topical administration to the surface of a mammalian eye.

In addition, in certain embodiments the compositions for use in the novel treatments of the present invention may be formed as aerosols, for example for intranasal administration.

In certain embodiments, oral compositions (such as tablets, suspensions, solutions) may be effective for local delivery to the oral cavity such as oral composition suitable for mouthwash for the treatment of oral mucositis.

In embodiments the subject being treated is a warm-blooded animal and, in particular, mammals including human.

In an additional embodiment, the modification is a modification of the phosphate moiety, whereby the modified phosphate moiety is selected from the group comprising phosphorothioate or lack of a phosphate group.

The molecules of the present invention comprise siRNA, siNA, synthetic siRNAs, synthetic shRNAs, and miRNA in addition to other nucleic acid sequences or molecules which encode such molecules or other inhibitory nucleotide molecules.

In some embodiments the nucleic acid compounds are useful for diagnosis. Without wishing to be bound to theory a double stranded nucleic acid molecule comprising a 3' terminal non-nucleotide can be efficiently delivered to specific cells and tissue and are useful in diagnosis of disorders on the specific cell or tissue. According, end modifications include detectable moieties including colorgenic agents, radiolabeled moieties and enymatic agents. In some embodiments the detectable agent is a biotin group. Such biotin group may preferably be attached to either the most 5' nucleotide of the sense strand or the most 3' nucleotide of the antisense strand or to both of those ends. The various end modifications as disclosed herein are preferably located at the ribose moiety of a nucleotide of the nucleic acid according to the present invention. More particularly, the end modification may be attached to or replace any of the OH-groups of the ribose moiety, including but not limited to the 2'OH, 3'OH and 5'OH position, provided that the nucleotide thus modified is a terminal nucleotide, preferably a 5' terminal nucleotide of the sense strand. It is to be understood that the nucleic acid molecules disclosed herein, or any long double-stranded RNA molecules (typically 25-500 nucleotides in length) which are processed by endogenous cellular complexes (such as DICER—see above) to form the siRNA molecules disclosed herein, or molecules which comprise the siRNA molecules disclosed herein, are incorporated into the molecules of the present invention to form additional novel molecules, and are employed in the treatment of the diseases or disorders described herein.

In particular, it is envisaged that a long oligonucleotide may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide is termed a tandem shRNA construct. It is envisaged that this long oligonucleotide is a single stranded oligonucleotide comprising one or more stem and loop structures, wherein each stem region comprises a sense and corresponding antisense siRNA sequence. Any molecules, such as, for example, antisense DNA molecules which comprise the inhibitory sequences disclosed herein (with the appropriate nucleic acid modifications) are particularly desirable and may be used in the same capacity as their corresponding RNAs/siRNAs for all uses and methods disclosed herein.

Backbone

The nucleoside subunits of the nucleic acid molecules disclosed herein may be linked to each other by phosphodiester bonds. The standard 5'3' phosphodiester bond may be optionally substituted with other linkages. For example, phosphorothioate, thiophosphate-D-ribose entities, triester, thioate, 2'-5' bridged backbone (may also be referred to as 5'-2' or 2'S'), PACE, 3'-(or -5')deoxy-3'-(or -5')thio-phosphorothioate, phosphorodithioate, phosphoroselenates, 3'-(or -5') deoxy phosphinates, borano phosphates, 3'-(or -5')deoxy-3'-(or 5'-)amino phosphoramidates, hydrogen phosphonates, phosphonates, borano phosphate esters, alkyl or aryl phosphonates and phosphotriester modifications such as alkylphosphotriesters, phosphotriester phosphorus linkages, 5'-ethoxyphosphodiester, P-alkyloxyphosphotriester, methylphosphonate, and nonphosphorus containing linkages for example, carbonate, carbamate, silyl, sulfur, sulfonate, sulfonamide, formacetal, thioformacetyl, oxime, methyleneimino, methylenemethylimino, methylenehydrazo, methylenedimethylhydrazo and methyleneoxymethylimino linkages. In addition, analogs of polynucleotides can be prepared wherein the structure of the nucleotide is fundamentally altered and that are better suited as therapeutic or experimental reagents. An example of a nucleotide analog is a peptide nucleic acid (PNA) wherein the deoxyribose (or ribose) phosphate backbone in DNA (or RNA comprises a polyamide backbone which is similar to that found in peptides. PNA analogs have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modified monomers useful in synthesizing the oligonucleotides include moieties having polymer backbones, cyclic backbones, or acyclic backbones.

Methods of Treatment

In another aspect, the present invention relates to a method for the treatment of a subject in need of treatment for a disease or disorder associated with the abnormal expression of a target gene, comprising administering to the subject an amount of an inhibitor which reduces or inhibits expression of the gene.

In certain embodiments the subject being treated is a warm-blooded animal and, in particular, mammals including human.

The methods of the invention comprise administering to the subject one or more inhibitory compounds which down-regulate expression of a gene; and in particular siRNA in a therapeutically effective dose so as to thereby treat the subject.

The term "treatment" refers to both therapeutic treatment and prophylactic or preventative measures, wherein the object is to prevent or slow down (lessen) a disorder as listed herein. Those in need of treatment include those already experiencing the disease or condition, those prone to having the disease or condition, and those in which the disease or condition is to be prevented. The compounds of the invention are administered before, during or subsequent to the onset of the disease or condition or symptoms associated therewith. In cases where treatment is for the purpose of prevention, then the present invention relates to a method for delaying the onset of or averting the development of the disease or disorder.

The present invention relates to the use of compounds which down-regulate the expression of the pro-apoptotic genes of the invention particularly to novel small interfering RNAs (siRNAs), in the treatment of the following diseases or conditions in which inhibition of the expression of the pro-apoptotic genes is beneficial: hearing loss, acute renal failure (ARF), glaucoma, acute respiratory distress syndrome (ARDS) and other acute lung and respiratory injuries, ischemia-reperfusion injury following lung transplantation, organ transplantation including lung, liver, heart, bone marrow, pancreas, cornea and kidney transplantation which includes DGF; spinal cord injury, pressure sores, age-related macular degeneration (AMD), dry eye syndrome, ocular ischemic conditions including ION and NAION; oral mucositis and chronic obstructive pulmonary disease (COPD). Other indications include chemical-induced nephrotoxicity and chemical-induced neurotoxicity, for example toxicity induced by cisplatin and cisplatin-like compounds, by aminoglycosides, by loop diuretics, and by hydroquinone and their analogs.

Methods, molecules and compositions which inhibit the pro-apoptotic genes of the invention are discussed herein at length, and any of said molecules and/or compositions may be beneficially employed in the treatment of a subject suffering from any of said conditions.

In a further aspect an article of manufacture is provided which includes packaging material comprising an oligonucleotide composition according to the invention that is therapeutically effective in treating a subject suffering from any one of the indications disclosed herein, and instructions for use.

Disclosed herein is a method of preparing a double-stranded RNA molecule capable of target-specific inhibition or down-regulating expression of a target gene wherein each RNA strand has a length from 19 to 25 nucleotides, wherein at least one strand has a non-nucleotide moiety covalently attached at a 3' or a 2' position of the sugar residue at the 3' terminal end thereof, comprising (a) synthesizing two RNA strands each having a length from 19 to 25 nucleotides, wherein said RNA strands are capable of forming a double-stranded RNA molecule, (b) combining the synthesized RNA strands under conditions, wherein a double-stranded RNA molecule is formed, wherein said double-stranded RNA molecule consists of a single double stranded region and at least one single stranded region comprising a non-nucleotide moiety covalently attached at a 3' or a 2' position of the sugar residue at the 3' terminal end of the strand in which it is present; wherein the non-nucleotide moiety is selected from propanol, a C3 alkyl moiety linked to a phosphodiester, a C3 alkyl moiety linked to a phosphorothioate, a deoxyriboabasic moiety or a riboabasic moiety and a combination thereof.

Provided herein is a process of preparing a pharmaceutical composition, which comprises:

providing one or more compounds disclosed herein; and admixing said compound with a pharmaceutically acceptable carrier.

The present invention also provides for a process of preparing a pharmaceutical composition, which comprises admixing one or more compounds of the present invention with a pharmaceutically acceptable carrier.

In one embodiment, the compound used in the preparation of a pharmaceutical composition is admixed with a carrier in a pharmaceutically effective dose. In a particular embodiment the compound of the present invention is conjugated to a steroid or to a lipid or to another suitable molecule e.g. to cholesterol.

Synthesis of Modified Compounds

The compounds of the present invention can be synthesized by any of the methods that are well known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Annu Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et. al., in IRL Press 1989 edited by Oliver R. W. A.; Kap. 7: 183-208.

Other synthetic procedures are known in the art e.g. the procedures as described in Usman et al., J. Am. Chem. Soc., 1987, 109:7845; Scaringe et al., NAR, 1990, 18:5433; Wincott et al., NAR 1995, 23:2677-2684; and Wincott et al., Methods Mol. Bio., 1997, 74:59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., Science 1992, 256:9923; International Patent Publication No. WO 93/23569; Shabarova et al., NAR 1991, 19:4247; Bellon et al., Nucleosides & Nucleotides, 1997, 16:951; Bellon et al., Bioconjugate Chem 1997, 8:204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via tandem synthesis methodology, as described for example in US Patent Publication No. 2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker is selected from a polynucleotide linker or a non-nucleotide linker.

The term "Covalent bonding" as used herein refers to chemical bonding that is characterized by the sharing of pairs of electrons between atoms.

The term "Noncovalent bonding" as used herein refers to a variety of interactions that are not covalent in nature between molecules or parts of molecules that provide force to hold the molecules or parts of molecules together, usually in a specific orientation or conformation. These noncovalent interactions include: ionic bonds, hydrophobic interactions, hydrogen bonds, Van der Waals forces and dipole-dipole bonds.

siRNAs and RNA Interference

RNA interference (RNAi) is a phenomenon involving double-stranded (ds) RNA-dependent gene specific posttranscriptional silencing. Initial attempts to study this phenomenon and to manipulate mammalian cells experimentally were frustrated by an active, non-specific antiviral defense mechanism which was activated in response to long dsRNA molecules (Gil et al. Apoptosis, 2000. 5:107-114). Later, it was discovered that synthetic duplexes of 21 nucleotide RNAs could mediate gene specific RNAi in mammalian cells, without stimulating the generic antiviral defense mechanisms (see Elbashir et al. Nature 2001, 411:494-498 and Caplen et al. PNAS USA 2001, 98:9742-9747). As a result, small interfering RNAs (siRNAs) have become powerful tools in attempting to understand gene function.

RNA interference (RNAi) in mammals is mediated by small interfering RNAs (siRNAs) (Fire et al, Nature 1998, 391:806) or microRNAs (miRNAs) (Ambros, Nature 2004, 431(7006):350-355; Bartel, Cell 2004, 116(2): 281-97). The corresponding process in plants is commonly referred to as specific post-transcriptional gene silencing (PTGS) or RNA silencing and is also referred to as quelling in fungi.

An siRNA is a double-stranded RNA or modified RNA molecule which down-regulates or silences (prevents) the expression of a gene/mRNA of its endogenous (cellular) counterpart.

The selection and synthesis of siRNA corresponding to known genes has been widely reported; (see for example Ui-Tei et al., J Biomed Biotech. 2006; 2006: 65052; Chalk et al., BBRC. 2004, 319(1): 264-74; Sioud & Leirdal, Met. Mol. Biol.; 2004, 252:457-69; Levenkova et al., Bioinform. 2004, 20(3):430-2; Ui-Tei et al., NAR. 2004, 32(3):936-48).

For examples of the use of, and production of, modified siRNA see, for example, Braasch et al., Biochem. 2003, 42(26):7967-75; Chiu et al., RNA, 2003, 9(9):1034-48; PCT publications WO 2004/015107 (atugen AG) and WO 02/44321 (Tuschl et al). U.S. Pat. Nos. 5,898,031 and 6,107, 094, teach chemically modified oligomers. US Patent Publication Nos. 2005/0080246 and 2005/0042647 relate to oligomeric compounds having an alternating motif and dsRNA compounds having chemically modified internucleoside linkages, respectively.

Other modifications have been disclosed. The inclusion of a 5'-phosphate moiety was shown to enhance activity of siRNAs in Drosophila embryos (Boutla, et al., Curr. Biol. 2001, 11:1776-1780) and is required for siRNA function in human HeLa cells (Schwarz et al., Mol. Cell, 2002, 10:537-48). Amarzguioui et al., (NAR, 2003, 31(2):589-95) showed that siRNA activity depended on the positioning of the 2'-O-methyl (2'OMe) modifications. Holen et al (NAR. 2003, 31(9): 2401-07) report that an siRNA having small numbers of 2'OMe modified nucleosides gave good activity compared to wild type but that the activity decreased as the numbers of 2'OMe modified nucleosides was increased. Chiu and Rana (RNA. 2003, 9:1034-48) teach that incorporation of 2'OMe modified nucleosides in the sense or antisense strand (fully modified strands) severely reduced siRNA activity relative to unmodified siRNA. The placement of a 2'OMe group at the 5'-terminus on the antisense strand was reported to severely limit activity whereas placement at the 3'-terminus of the antisense and at both termini of the sense strand was tolerated (Czauderna et al., NAR. 2003, 31(11):2705-16; WO 2004/015107).

Several studies have revealed that siRNA therapeutics are effective in vivo in both mammals and in humans. Bitko et al., have shown that specific siRNA molecules directed against the respiratory syncytial virus (RSV) nucleocapsid N gene are effective in treating mice when administered intranasally (Nat. Med. 2005, 11(1):50-55). Recent reviews discussing siRNA therapeutics are available (Batik, et al., J. Mol. Med. 2005, 83:764-773; Dallas and Vlassov, Med. Sci. Monitor 2006, 12(4):RA67-74; Chakraborty, Current Drug Targets 2007, 8(3):469-82; Dykxhoorn et al., Gene Therapy 2006. 13:541-552).

Mucke (IDrugs 2007 10(1):37-41) presents a review of current therapeutics, including siRNA to various targets, for the treatment of ocular diseases, for example age related macular degeneration (AMD) and glaucoma.

A number of PCT applications have recently been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

RNA interference (RNAi) is based on the ability of dsRNA species to enter a cytoplasmic protein complex, where it is then targeted to the complementary cellular RNA and specifically degrade it. The RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir et al., Genes Dev., 2001, 15(2): 188-200). In more detail, longer dsRNAs are digested into short (17-29 bp) dsRNA fragments (also referred to as short inhibitory RNAs, "siRNAs") by type III RNAses (DICER, DROSHA, etc.; Bernstein et al., Nature, 2001, 409(6818): 363-6; Lee et al., Nature, 2003, 425(6956):415-9). The RISC protein complex recognizes these fragments and complementary mRNA. The whole process is culminated by endonuclease cleavage of target mRNA (McManus & Sharp, Nature Rev Genet, 2002, 3(10):737-47; Paddison & Hannon, Curr Opin Mol. Ther. 2003, 5(3):217-24). (For additional information on these terms and proposed mechanisms, see for example Bernstein et al., RNA 2001, 7(11):1509-21; Nishikura, Cell 2001, 107(4):415-8 and PCT publication WO 01/36646).

siRNA Structures

The selection and synthesis of siRNA corresponding to known genes has been widely reported; (see for example Ui-Tei et al., J Biomed Biotech. 2006; 2006: 65052; Chalk et al., BBRC. 2004, 319(1): 264-74; Sioud & Leirdal, Met. Mol. Biol.; 2004, 252:457-69; Levenkova et al., Bioinform. 2004, 20(3):430-2; Ui-Tei et al., NAR. 2004, 32(3):936-48).

For examples of the use of, and production of, modified siRNA see, for example, Braasch et al., Biochem. 2003, 42(26):7967-75; Chiu et al., RNA, 2003, 9(9):1034-48; PCT publications WO 2004/015107 (atugen AG) and WO 02/44321 (Tuschl et al). U.S. Pat. Nos. 5,898,031 and 6,107,094, teach chemically modified oligomers. US Patent Publication Nos. 2005/0080246 and 2005/0042647 relate to oligomeric compounds having an alternating motif and dsRNA compounds having chemically modified internucleoside linkages, respectively.

Other modifications have been disclosed. The inclusion of a 5'-phosphate moiety was shown to enhance activity of siRNAs in Drosophila embryos (Boutla, et al., Curr. Biol. 2001, 11:1776-1780) and is required for siRNA function in human HeLa cells (Schwarz et al., Mol. Cell, 2002, 10:537-48). Amarzguioui et al., (NAR, 2003, 31(2):589-95) showed that siRNA activity depended on the positioning of the 2'-O-methyl (2'OMe) modifications. Holen et al (NAR. 2003, 31(9): 2401-07) report that an siRNA having small numbers of 2'OMe modified nucleosides gave good activity compared to wild type but that the activity decreased as the numbers of 2'OMe modified nucleosides was increased. Chiu and Rana (RNA. 2003, 9:1034-48) teach that incorporation of 2'OMe modified nucleosides in the sense or antisense strand (fully modified strands) severely reduced siRNA activity relative to unmodified siRNA. The placement of a 2'OMe group at the 5'-terminus on the antisense strand was reported to severely limit activity whereas placement at the 3'-terminus of the antisense and at both termini of the sense strand was tolerated (Czauderna et al., NAR. 2003, 31(11):2705-16; WO 2004/015107).

The double stranded RNA molecules disclosed herein possess one 3' non-nucleotide overhang on either the sense or antisense strand and optionally two 3' overhangs, one on each of the sense and antisense strands.

The molecules disclosed herein offer an advantage in that they are non-toxic and are useful in the preparation of pharmaceutical compositions for treatment of various diseases and disorders.

PCT Patent Application No. PCT/IL2007/001278 (PCT Publication No. WO 2008/050329) and U.S. Ser. No. 11/978, 089 to the assignee of the present invention relate to inhibitors of pro-apoptotic genes, and are incorporated by reference in their entirety.

The present invention relates generally to compounds which down-regulate expression of various genes, particularly to novel small interfering RNAs (siRNAs), and to the use of these novel siRNAs in the treatment of a subject suffering from various medical conditions.

Molecules and compositions are discussed herein at length, and any of said molecules and/or compositions may be beneficially employed in the treatment of a subject suffering from any of said conditions.

The siRNA compounds of the present invention possess structures and modifications which may for example increase activity, increase stability, and or minimize toxicity; the novel modifications of the siRNAs of the present invention are beneficially applied to double stranded RNA useful in preventing or attenuating target gene expression, in particular the target genes discussed herein.

According to one aspect provided herein are inhibitory oligonucleotide compounds comprising unmodified and/or modified nucleotides. One strand of the compound comprises at least one 3' overhang comprising at least one non-nucleotide moiety, preferably two non-nucleotide moieties. The compounds disclosed herein preferably comprise unmodified ribonucleotides and modified ribonucleotides and or one or more unconventional moiety. In some embodiments at least one of N or N' is selected from the group consisting of a sugar modification, a base modification and an internucleotide linkage modification. In some embodiments the compounds disclosed herein include at least one modified nucleotide including DNA, LNA (locked nucleic acid) including ENA (ethylene-bridged nucleic acid; PNA (peptide nucleic acid); arabinoside; PACE (phosphonoacetate and derivatives thereof), mirror nucleotide, or nucleotides with a 6 member sugar analog (e.g. hexose or morpholino).

In one embodiment the compound comprises at least one modified ribonucleotide having a 2' modification on the sugar moiety ("2' sugar modification"). In certain embodiments the compound comprises 2'O-alkyl or 2'-fluoro or 2'O-allyl or any other 2' sugar modification, optionally on alternate positions. One possible 2' modification is 2' O-methyl (2' methoxy, 2'OMe).

Other stabilizing modifications are also possible (e.g. modified nucleotides added to a 3' or 5' terminus of an oligomer). In some embodiments the backbone of the oligonucleotides is modified and comprises phosphate-D-ribose entities but may also contain thiophosphate-D-ribose entities, phosphodiester L-ribose entities, triester, thioate, 2'-5' bridged backbone (also may be referred to as 5'-2'), PACE modified internucleotide linkage or any other type of modification.

The invention has been described in an illustrative manner, and it is to be understood that the terminology used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry is useful for detection of cells containing specific DNA and mRNA sequences (Testoni et al., Blood 1996, 87:3822.) Methods of performing RT-PCR are also well known in the art.

Sequence Listing

The Sequence Listing filed electronically herewith is hereby incorporated by reference in its entirety (File Name: 217_PCT2_ST25.txt; Date Created: Jan. 6, 2011; File Size: 6.00 Kb.)

Example 1

Generation of Nucleic Acid Molecules and In Vitro Testing of Modified siRNA Compounds Using proprietary algorithms and the known sequence of a target nucleotide, for example the mRNA of a target gene, the sense and antisense sequences of many potential siRNA nucleic acid molecules are generated. Nucleic acid molecules are depicted in 5' to 3' orientation, and the sense and complementary antisense sequences are depicted on the same line in the tables, unless otherwise noted.

Table A provides exemplary, non-limiting, nucleic acid sequences useful in generating nucleic acid molecules disclosed herein.

TABLE A

|  | Sense 5'>3' | SEQ ID NO | Antisense 5'>3' | SEQ ID NO |
|---|---|---|---|---|
| CASP2_4 | GCCAGAAUGUGGAACUCCU | 1 | AGGAGUUCCACAUUCUGGC | 2 |
| MYD88_11 | GAAUGUGACUUCCAGACCA | 3 | UGGUCUGGAAGUCACAUUC | 4 |

TABLE A-continued

|  | Sense 5'>3' | SEQ ID NO | Antisense 5'>3' | SEQ ID NO |
|---|---|---|---|---|
| RAC1_2 | GAGUCCUGCAUCAUUUGAA | 5 | UUCAAAUGAUGCAGGACUC | 6 |
| RHOA_29 | UCGACAGCCCUGAUAGUUU | 7 | AAACUAUCAGGGCUGUCGA | 8 |
| RHOA_48 | CAGAAGUCAUCUUGCUACA | 9 | UGUAGCAAGAUGACUUCUG | 10 |
| RHOA_50 | GUGGCAGAGUUACAGUUCA | 11 | UGAACUGUAACUCUGCCAC | 12 |
| RHOA_58 | GUGGCAGAGUUACAGUUCU | 13 | AGAACUGUAACUCUGCCAC | 14 |
| RHOA_60 | CAUCGACAGCCCUGAUAGA | 15 | UCUAUCAGGGCUGUCGAUG | 16 |
| RHOA_61 | GAUCUUCGGAAUGAUGAGA | 17 | UCUCAUCAUUCCGAAGAUC | 18 |
| RHOA_70 | CAUCGACAGCCCUGAUAGU | 19 | ACUAUCAGGGCUGUCGAUG | 20 |
| RHOA_75 | UCGACAGCCCUGAUAGUUA | 21 | UAACUAUCAGGGCUGUCGA | 22 |
| TLR2_37 | GGUGGAGAACCUUAUGGUC | 23 | GACCAUAAGGUUCUCCACC | 24 |
| TLR2_46 | AGAUAAUGAACACCAAGAC | 25 | GUCUUGGUGUUCAUUAUCU | 26 |
| CASP2_25 | GAAUGUGGAACUCCUCAAC | 27 | GUUGAGGAGUUCCACAUUC | 28 |

Activity:

Single stranded oligonucleotides (sense strand and antisense strand) are synthesized using standard synthesis procedures. DMT-propane-Diol phosphoramidite ChemGenes; CLP-9908) is coupled at a concentration of 0.05M. Duplexes are generated by annealing complementary single stranded oligonucleotides. In a laminar flow hood, a ~500 µM Stock Solution of single stranded oligonucleotide is prepared by diluting in WFI (water for injection, Norbrook). Actual ssRNA concentrations are determined by diluting each 500 µM ssRNA 1:200 using WFI, and measuring the OD using Nano Drop. The procedure is repeated 3 times and the average concentration is calculated. The Stock Solution was then diluted to a final concentration of 250 µM. Complementary single strands were annealed by heating to 85° C. and allowing to cool to room temperature over at least 45 minutes. Duplexes were tested for complete annealing by testing 5 µl on a 20% polyacrylamide gel and staining Samples were stored at −80° C.

The double stranded nucleic acid molecules disclosed herein were tested for activity as follows: About 1.5-2×10$^5$ tested cells (HeLa cells and/or 293T cells for siRNA targeting human genes and NRK52 (normal rat kidney proximal tubule cells) cells and/or NMuMG cells (mouse mammary epithelial cell line) for siRNA targeting the rat/mouse gene) were seeded per well in 6 wells plate (70-80% confluent).

About 24 hours later, cells were transfected with modified siRNA compounds using the Lipofectamine™ 2000 reagent (Invitrogen) at final concentrations of from 0.001 nM to about 50 nM. The cells were incubated at 37° C. in a $CO_2$ incubator for 72 h.

As positive control for transfection PTEN-Cy3 labeled modified siRNA compounds are used. GFP siRNA compounds are used as negative control for siRNA activity.

At 72 h after transfection cells are harvested and RNA was extracted from cells. Transfection efficiency is tested by fluorescent microscopy.

The percent of inhibition of gene expression using specific preferred siRNA structures is determined using qPCR analysis of a target gene in cells expressing the endogenous gene.

The IC50 value of the tested RNAi activity is determined by constructing a dose-response curve using the activity results obtained with the various final siRNA concentrations. The dose response curve is constructed by plotting the relative amount of residual target mRNA versus the logarithm of transfected siRNA concentration. The curve is calculated by fitting the best sigmoid curve to the measured data. The method for the sigmoid fit is also known as a 3-point curve fit.

$$Y = Bot + \frac{100 - Bot}{1 + 10^{(LogIC50-X) \times HillSlope}}$$

where Y is the residual target mRNA response, X is the logarithm of transfected siRNA concentration, Bot is the Y value at the bottom plateau, LogIC50 is the X value when Y is halfway between bottom and top plateaus and HillSlope is the steepness of the curve.

Serum Stability Experiments

The double stranded nucleic acid molecules were tested for duplex stability in human serum or human tissue extract, as follows:

siRNA molecules at final concentration of 7 uM are incubated at 37° C. in 100% human serum (Sigma Cat#H4522). (siRNA stock 100 uM diluted in human serum 1:14.29 or human tissue extract from various tissue types). Five ul (5 ul) are added to 15 ul 1.5xTBE-loading buffer at different time points (for example 0, 30 min, 1 h, 3 h, 6 h, 8 h, 10 h, 16 h and 24 h). Samples are immediately frozen in liquid nitrogen and are kept at −20° C.

Each sample is loaded onto a non-denaturing 20% acrylamide gel, prepared according to methods known in the art. The oligos are visualized with ethidium bromide under UV light.

In general, the siRNAs having specific sequences that are selected for in vitro testing are specific for human and a second species such as rat or rabbit genes.

Stability to Exonucleases

To study the stabilization effect of 3' non-nucleotide moieties on a nucleic acid molecule the sense strand, the antisense strand and the annealed siRNA duplex are incubated in cytosolic extracts prepared from different cell types. A protocol for testing stability in HCT116 cells is provided below.

Extract: HCT116 cytosolic extract (12 mg/ml).

Extract buffer: 25 mM Hepes pH-7.3 at 37° C.; 8 mM MgCl; 150 mM NaCl with 1 mM DTT was added fresh immediately before use.

Method: 3.5 ml of test siRNA (100 mM), were mixed with 46.5 ml contain 120 mg of HCT116 cytosolic extract. The 46.5 ml consists of 12 ml of HCT116 extract, and 34.5 ml of the extract buffer supplemented with DTT and protease inhibitors cocktail/100 (Calbiochem, setIII-539134). The final concentration of the siRNA in the incubation tube is 7 mM. The sample was incubated at 37° C., and at the indicated time point 5 ml were moved to fresh tube, mixed with 15 ml of 1×TBE-50% Glycerol loading buffer, and snap frozen in Liquid N2. The final concentration of the siRNA in the loading buffer is 1.75 mM (21 ng siRNA/ml). For Analyses by native PAGE and EtBr staining 50 ng are loaded per lane. For Northern analyses 1 ng of tested siRNA was loaded per lane. Other cell types include HeLa and hepatic stellate cells (HSC).

The applicants have shown that nucleic acid molecules which include the 3' terminal alkyl; or alkyl derivative overhang exhibit enhanced stability compared to a blunt ended nucleic acid molecules and nucleic acid molecules comprising 3' nucleotide overhangs.

Exemplary Compounds siRNA compounds comprising non-nucleotide moieties covalently attached to the 3' terminus were synthesized and tested as described above. FIG. 2 provides a table of compounds useful in RNAi comprising sequences and modifications disclosed herein. Legend for the modifications follows: a prefix "z" indicates a moiety (nucleotide or non-nucleotide) covalently attached to the 3' or 5' terminal nucleotide. For example zdT refers to a dT overhang; zdT;zdT refers to a dTdT overhang. A prefix "y" indicates a nucleotide substitution, for example yLdA refers to a L-deoxyriboadenine substituted for a ribonucleotide in the sense strand or antisense strand; and ydT refers to a deoxyribothymidine substituted for a ribonucleotide in the sense or antisense oligonucleotide. A prefix "m" refers to a 2'OMe sugar modified ribonucleotide. Additional codes are set forth hereinbelow in Table B.

TABLE B

| Code | Description |
| --- | --- |
| Ra | riboadenosine-3'-phosphate; 3'-adenylic acid |
| RC | ribocytidine-3'-phosphate; 3'-cytidylic acid |
| RG | riboguanosine-3'-phosphate; 3'-guanylic acid |
| RU | ribouridine-3'-phosphate; 3'-uridylic acid |
| mA | 2'-O-methyladenosine-3'-phosphate; 2'-O-methyl-3'-adenylic acid |
| mC | 2'-O-methylcytidine-3'-phosphate; 2'-O-methyl-3'-cytidylic acid |
| mG | 2'-O-methylguanosine-3'-phosphate; 2'-O-methyl-3'-guanylic acid |
| mU | 2'-O-methyluridine-3'-phosphate; 2'-O-methyl-3'-uridylic acid |
| dA | deoxyriboadenosine-3'-phosphate; 2'-deoxyribo-3'-adenylic acid |
| dC | deoxyribocytidine-3'-phosphate; 2'-deoxyribo-3'-cytidylic acid |
| dG | deoxyriboguanosine-3'-phosphate; 2'-deoxyribo-3'-guanylic acid |
| dT | thymidine-3'-phosphate; 3'-thymidylic acid |
| rA2p | riboadenosine-2'-phosphate; 2'-adenylic acid |
| rC2p | ribocytidine-2'-phosphate; 2'-cytidylic acid |
| rG2p | riboguanosine-2'-phosphate; 2'-guanylic acid |
| rU2p | ribouridine-2'-phosphate; 2'-uridylic acid |
| LdA | L-deoxyriboadenosine-3'-phosphate (mirror image dA) |
| LdC | L-deoxyribocytidine-3'-phosphate (mirror image dC) |
| LdG | L-deoxyriboguanosine-3'-phosphate (mirror image dG) |

TABLE B-continued

| Code | Description |
|---|---|
| LdT | L-deoxyribothymidine-3'-phosphate (mirror image dT) |
| DB | abasic deoxyribose-3'-phosphate; 1,2-dideoxy-D-ribofuranose-3-phosphate; 1,4-anhydro-2-deoxy-D-ribitol-3-phosphate |
| zidB | Inverted abasic deoxyribose-5'-phosphate at terminus; 5' = 5'-5' idAb; At 3' = 3'-3' idAb |
| P | 5' phosphate |
| S | 5' phosphorothioate |
| $ | lacking a 3' linker (used together with above nucleotides at the 3' end of the sequence) |
| 3mN2p | 3'-O-methyl ribo-nucleotide-2'-phosphate |
| yC3p | substitute a ribonucleotide with 3-Hydroxypropane-1-phosphate |
| ydA | substitute a ribonucleotide with deoxyriboAdenosine-3'-phosphate; |
| ydT | substitute a ribonucleotide with deoxyriboThymidine-3'-phosphate; |
| ydU | substitute a ribonucleotide with deoxyUridine |
| yLdA | substitute a ribonucleotide with L-deoxyriboAdenosine-3'-phosphate |
| yLdC | substitute a ribonucleotide with L-deoxyriboCytidine-3'-phosphate |
| yLdG | substitute a ribonucleotide with L-deoxyriboGuanosine-3'-phosphate |
| ymA | substitute a ribonucleotide with 2'-O-methylAdenosine-3'-phosphate; |
| ymC | substitute a ribonucleotide with 2'-O-methylCytidine-3'-phosphate; |
| ymU | substitute a ribonucleotide with 2'-O-methylUridine-3'-phosphate; |
| yrA | substitute a ribonucleotide with riboAdenosine-3'-phosphate; |
| yrC | substitute a ribonucleotide with riboCytidine-3'-phosphate; |
| yrG | substitute a ribonucleotide with riboGuanosine-3'-phosphate; |
| yrU | substitute a ribonucleotide with riboUridine-3'-phosphate; |
| zC3p | $(CH_2)3$-Pi = 3-Hydroxypropane-1-phosphate (C3Pi) |
| zC3p; zC3p | $(CH_2)3$-Pi x2; = 3-Hydroxypropane-1-phosphate; (C3Pi-C3Pi) |
| zc3p; zc3p; zc3p | $(CH_2)3$-Pi x3; = 3-Hydroxypropane-1-phosphate; (C3Pi-C3Pi-C3Pi) |
| zc3p; zc3ps | $(CH_2)3$-Pi; $(CH_2)$-3'phosphorothioate (C3Pi-C3Ps) |
| zC3p; zrB | $(CH_2)3$-Pi; ribo-Abasic-3'-Pi |
| zC3p; zrG | $(CH_2)3$-Pi_rG |
| zC6Np | Amino-C6-Phosphate |
| zC6Np; zrC; zrA | Amino-C6-Phosphate_rCrA |
| zdB; zdB | abasic deoxyribose-3'-phosphate x2 (dAb-dAb) |
| ZdT | Deoxy-Thymidine-3'-Phosphate |
| zdT; zdT | dTdT overhang at 3' |
| ZidB | Inverted abasic deoxyribose-5'-phosphate; At 5' = 5'-5' idAb; At 3' = 3'-3' idAb |
| ZidT | Inverted-Deoxy-Thymidine-5'-Phosphate |
| ZiLd | Inverted L-DNA |
| ZirB | Inverted abasic ribose-5'-phosphate |
| zirB; zirB | Inverted abasic ribose-5'-phosphate x2 |
| zirB; zrC; zrA | Inverted abasic ribose-3'-phosphate_rCrA |
| ZLdA | L-deoxyriboAdenosine-3'-phosphate |
| ZLdC | L-deoxyriboCytidine-3'-phosphate |
| ZLdT | L-deoxyriboThymidine-3'-phosphate |
| ZmC | 2'-O-methylcytidine-3'-ethoxyphosphate |
| ZmU | 2'-O-methyluridine-3'-ethoxyphosphate |
| ZOle | Oleic acid |
| zrA; zrG | rArG |
| zrB; zrB | abasic ribose-3'-phosphate x2 |
| zrC; zrA | rC; rA |
| zrU; zrG | rUrG |
| zrU; zrU | rUrU |

In the following tables, the codes used in the column labeled "Sense 5→3 Antisense 5→3" are the codes shown in Table B. The columns labeled as "sense modifications" and "antisense modifications" provide a brief description of the positional modifications used in each of the sense and antisense strands, for example 20-C3; C3 refers to a 3' C3Pi-C3OH terminal overhang and 20-dTdT refers to a 3' dTdT terminal overhang (beginning at position 20 on a 19-mer), 2,4,6,8,10,12,14,16,18-2'-OMe refers to 2'OMe sugar modified ribonucleotides in positions 2, 4, 6, 8, 10, 12, 14, 16, 18.

TABLE 1

| No. | compound name | stability in hHSC extract | Sense 5->3<br>Antisense 5->3 | sense modifications | antisense modifications |
|---|---|---|---|---|---|
| 1 | RAC1_2_S710 | <3 h | rG; rA; rG; rU; rC; rC; rU; rG; rC; rA; rU; rC; rA; rU; rU; rU; rG; rA; rA$<br>rU; rU; rC; rA; rA; rA; rU; rG; rA; rU; rG; rC; rA; rG; rG; rA; rC; rU; rC$ | — | — |
| 2 | RAC1_2_S1231 | 6 h-12 h | rG; rA; rG; rU; rC; rC; rU; rG; rC; rA; rU; rC; rA; rU; rU; rU; rG; rA; rA; zc3p; zc3p$ | 20-C3; C3 | 20-C3; C3 |

TABLE 1-continued

| No. | compound name | stability in hHSC extract | Sense 5->3<br>Antisense 5->3 | sense modifications | antisense modifications |
|---|---|---|---|---|---|
| 3 | RAC1_2_S709 | 6 h-12 h | rU; rU; rC; rA; rA; rA; rU; rG; rA; rU; rG; rC; rA; rG; rG; rA; rC; rU; rC; zc3p; zc3p$<br>rG; rA; rG; rU; rC; rC; rU; rG; rC; rA; rU; rC; rA; rU; rU; rU; rG; rA; rA; zdT; zdT$ | 20-dTdT | 20-dTdT |
| 4 | RAC1_2_S1759 | 6 h-12 h | rU; rU; rC; rA; rA; rA; rU; rG; rA; rU; rG; rC; rA; rG; rG; rA; rC; rU; rC; zdT; zdT$<br>rG; rA; rG; rU; rC; rC; rU; rG; rC; rA; rU; rC; rA; rU; rU; rU; rG; rA; rA; zmU; zmU$<br>rU; rU; rC; rA; rA; rA; rU; rG; rA; rU; rG; rC; rA; rG; rG; rA; rC; rU; rC; zmU; zmU$ | 20-mU; mU | 20-mU; mU |

The data presented in Table 1 shows that C3Pi-C3OH 3' terminal overhang (2) improves siRNA nuclease resistance in cell extracts compared to blunt unmodified siRNA (1). The stabilizing effect of the C3-C3 is similar to the dTdT (3) and 2'OMe U (4) 3' terminal overhangs. RAC1_2 sequences are set forth in SEQ ID NOS:5 and 6.

TABLE 2

| No | compound name | stability of sense strand in HCT116 | Patent Sense 5->3<br>Antisense 5->3 | sense modifications | antisense modifications |
|---|---|---|---|---|---|
| 1 | CASP2_4_S1152 | 24 h | rG; rC; rC; rA; rG; rA; rA; rU; rG; rU; rG; rG; rA; rA; rC; rU; rC; rC; rU; zc3p; zc3p$<br>rA; rG; rG; rA; rG; rU; rU; rC; rC; rA; rC; rA; rU; rU; rC; rU; rG; rG; rC$ | 20-C3; C3 | —<br>(unmodified) |
| 2 | CASP2_4_S1153 | 24 h | zidB; rG; rC; rC; rA; rG; rA; rA; rU; rG; rU; rG; rG; rA; rA; rC; rU; rC; rC; rU; zidB$<br>rA; rG; rG; rA; rG; rU; rU; rC; rC; rA; rC; rA; rU; rU; rC; rU; rG; rG; rC$ | 0,20-cap-idAb | |
| 3 | CASP2_4_S710 | 1 h | rG; rC; rC; rA; rG; rA; rA; rU; rG; rU; rG; rG; rA; rA; rC; rU; rC; rC; rU$<br>rA; rG; rG; rA; rG; rU; rU; rC; rC; rA; rC; rA; rU; rU; rC; rU; rG; rG; rC$ | — | — |

The data in Table 2 shows that C3-C3 3' terminal overhang (1) and a strand comprising 5' and 3' inverted deoxy abasic moieties (2) improves strand nuclease resistance in cell extract when compared to unmodified strand (3). CASP2_4 sequences are set forth in SEQ ID NOS:1 and 2.

TABLE 3

Figure 4:
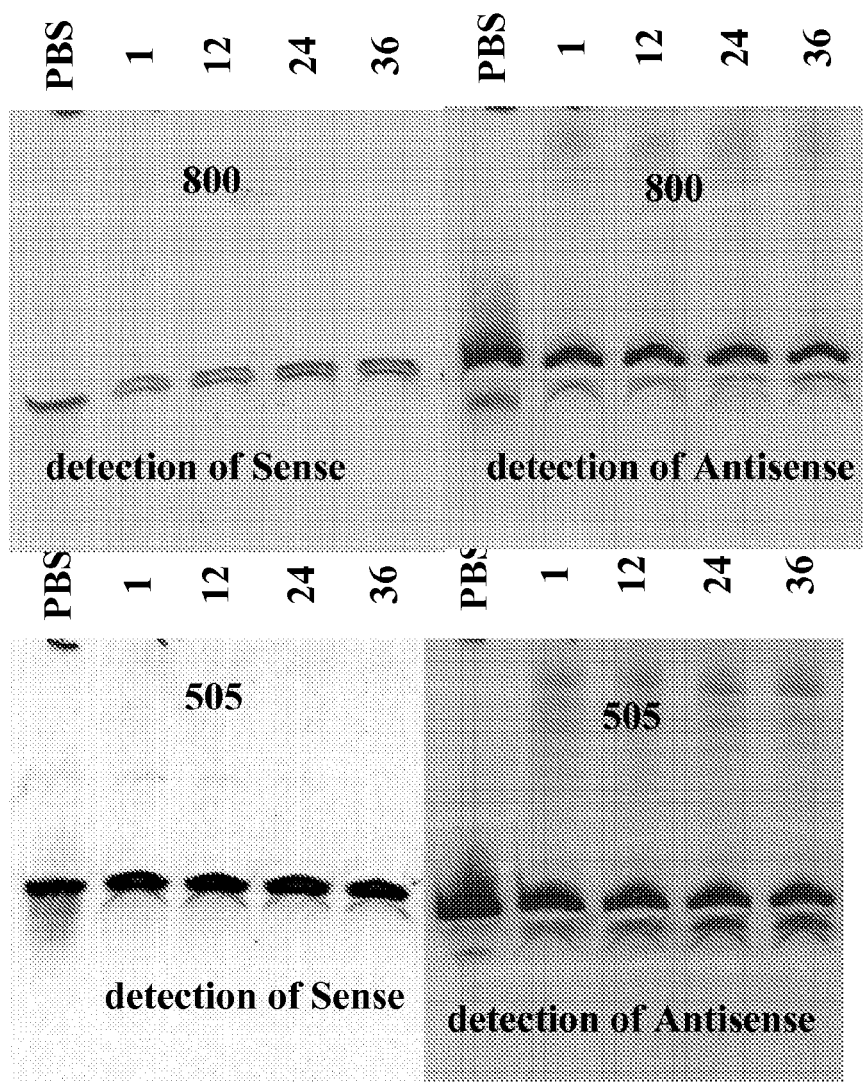
FIG. 4 provides stability data for two double stranded molecules, S505 which is a blunt ended 19-mer duplex (compound 5 in Table 3 in the Examples), and S800 which is a 19-mer duplex comprising a non-nucleotide C3C3 3' terminus overhang (C3Pi-C3OH, compound 7 in Table 3 in the Examples). The two compounds are nuclease stable in cell extract for at least 36 hours, yet S800 has an IC50 value of about 0.17 nM and S505 has an IC50 value of 1.1 nM. The sequences used in generating the two compounds are set forth in SEQ ID NOS:1 and 2 (sense strand and antisense strand, respectively).

| No. | Compound name | IC50, nM | stability in cell extract, hours (FIG. 4) | Sense 5->3<br>Antisense 5->3 | sense modifications | antisense modifications |
|---|---|---|---|---|---|---|
| 1 | RAC1_2_S73 | 0.207 | | rG; mA; rG; mU; rC; mC; rU; mG; rC; mA; rU; mC; rA; mU; rU; mU; rG; mA; rA$<br>mU; rU; mC; rA; mA; rA; mU; rG; mA; rU; mG; rC; mA; rG; mG; rA; mC; rU; mC$ | 2,4,6,8,10,12, 14,16,18-2'-OMe-3'-Pi | 1,3,5,7,9,11,13, 15,17,19-2'-OMe-3'-Pi |
| 2 | RAC1_2_S1005 | 0.067 | | rG; mA; rG; mU; rC; mC; rU; mG; rC; mA; rU; mC; rA; mU; rU; mU; rG; mA; rA; zidB$<br>mU; rU; mC; rA; mA; rA; mU; rG; mA; rU; mG; rC; mA; rG; mG; rA; mC; rU; mC; zidB$ | 2,4,6,8,10,12, 14,16,18-2'-OMe-3'-Pi; 20-cap-idAb | 1,3,5,7,9,11,13, 15,17,19-2'-OMe-3'-Pi; 20-cap-idAb |
| 3 | RAC1_2_S1154 | 0.082 | | rG; mA; rG; mU; rC; mC; rU; mG; rC; mA; rU; mC; rA; mU; rU; mU; rG; mA; rA; zc3p; zc3p$ | 2,4,6,8,10,12, 14,16,18-2'-OMe-3'-Pi; 20- | 1,3,5,7,9,11,13, 15,17,19-2'-OMe-3'-Pi; 20- |

TABLE 3-continued

| No. | Compound name | IC50, nM | stability in cell extract, hours (FIG. 4) | Sense 5->3 Antisense 5->3 | sense modifications | antisense modifications |
|---|---|---|---|---|---|---|
| 4 | RAC1_2_S1156 | 0.174 | | mU; rU; mC; rA; mA; rA; mU; rG; mA; rU; mG; rC; mA; rG; mG; rA; mC; rU; mC; zc3p; zc3p$<br>rG; mA; rG; mU; rC; mC; rU; mG; rC; mA; rU; mC; rA; mU; rU; mU; rG; mA; rA$ | C3; C3<br><br>2,4,6,8,10,12, 14,16,18-2'-OMe-3'-Pi | C3; C3<br><br>1,3,5,7,9,11,13, 15,17,19-2'-OMe-3'-Pi; 20-C3; C3 |
| 5 | CASP2_4_S505 | 1.1 | 36 | mU; rU; mC; rA; mA; rA; mU; rG; mA; rU; mG; rC; mA; rG; mG; rA; mC; rU; mC; zc3p; zc3p$<br>rG; rC; rC; rA; rG; rA; rA; rU; rG; rU; rG; rG; rA; rA; rC; rU; rC; LdC; rU$<br>rA; mG; rG; mA; rG; mU; rU; mC; rC; rA; mC; rA; mU; rU; mC; rU; mG; rG; mC$ | 18-L-DNA-3'-Pi | 2,4,6,8,11,13, 15,17,19-2'-OMe-3'-Pi |
| 6 | CASP2_4_S796 | 0.202 | | rG; rC; rC; rA; rG; rA; rA; rU; rG; rU; rG; rG; rA; rA; rC; rU; rC; LdC; rU$<br>rA; mG; rG; mA; rG; mU; rU; mC; rC; rA; mC; rA; mU; rU; mC; rU; mG; rG; mC; zdT; zdT$ | 18-L-DNA-3'-Pi | 2,4,6,8,11,13, 15,17,19-2'-OMe-3'-Pi; 20-dTdT |
| 7 | CASP2_4_S800 | 0.169 | 36 | rG; rC; rC; rA; rG; rA; rA; rU; rG; rU; rG; rG; rA; rA; rC; rU; rC; LdC; rU$<br>rA; mG; rG; mA; rG; mU; rU; mC; rC; rA; mC; rA; mU; rU; mC; rU; mG; rG; mC; zc3p; zc3p$ | 18-L-DNA-3'-Pi | 2,4,6,8,11,13, 15,17,19-2'-OMe-3'-Pi; 20-C3; C3 |
| 8 | CASP2_4_S802 | 0.216 | | rG; rC; rC; rA; rG; rA; rA; rU; rG; rU; rG; rG; rA; rA; rC; rU; rC; LdC; rU$<br>rA; mG; rG; mA; rG; mU; rU; mC; rC; rA; mC; rA; mU; rU; mC; rU; mG; rG; mC; zc3p; zrB$ | 18-L-DNA-3'-Pi | 2,4,6,8,11,13, 15,17,19-2'-OMe-3'-Pi; 20-C3; rAb |

The data provided in Table 3 shows that 1) introduction of C3-C3 moieties (3, 4 and 7), inverted deoxy abasic (2), C3-ribo abasic (8) at 3' end of antisense or on both antisense and sense strand improves siRNA activity compared to a blunt ended compounds (1 and 5) and is more active than the same compound with 3' dTdT overhangs (6); and that 2) the improved activity of the compound comprising the 3' terminal C3-C3 is not due to increased stability in cell extract since both compounds (5 and 7) are highly stable (at least 36 h).

TABLE 4

| No. | Compound name | concentration | % Residual target mRNA | Sense 5->3 Antisense 5->3 | sense modifications | antisense modifications |
|---|---|---|---|---|---|---|
| 1 | RAC1_2_S73 | 40 nM<br>5 nM | 25<br>35 | rG; mA; rG; mU; rC; mC; rU; mG; rC; mA; rU; mC; rA; mU; rU; mU; rG; mA; rA$<br>mU; rU; mC; rA; mA; rA; mU; rG; mA; rU; mG; rC; mA; rG; mG; rA; mC; rU; mC$ | 2,4,6,8,10,12, 14,16,18-2'-OMe-3'-Pi | 1,3,5,7,9,11,13,15, 17,19-2'-OMe-3'-Pi |
| 2 | RAC1_2_S1154 | 40 nM<br>5 nM | 12<br>32 | rG; mA; rG; mU; rC; mC; rU; mG; rC; mA; rU; mC; rA; mU; rU; mU; rG; mA; rA; zc3p; zc3p$<br>mU; rU; mC; rA; mA; rA; mU; rG; mA; rU; mG; rC; mA; rG; mG; rA; mC; rU; mC; zc3p; zc3p$ | 2,4,6,8,10,12, 14,16,18-2'-OMe-3'-Pi; 20-C3; C3 | 1,3,5,7,9,11,13,15, 17,19-2'-OMe-3'-Pi; 20-C3; C3 |
| 3 | RAC1_2_S1155 | 40 nM<br>5 nM | 32<br>50 | rG; mA; rG; mU; rC; mC; rU; mG; rC; mA; rU; mC; rA; mU; rU; mU; rG; mA; rA; zc3p; zc3p$<br>mU; rU; mC; rA; mA; rA; mU; rG; mA; rU; mG; rC; mA; rG; mG; rA; mC; rU; mC$ | 2,4,6,8,10,12, 14,16,18-2'-OMe-3'-Pi; 20-C3; C3 | 1,3,5,7,9,11,13,15, 17,19-2'-OMe-3'-Pi |
| 4 | RAC1_2_S1156 | 40 nM<br>5 nM | 24<br>44 | rG; mA; rG; mU; rC; mC; rU; mG; rC; mA; rU; mC; rA; mU; rU; mU; rG; mA; rA$<br>mU; rU; mC; rA; mA; rA; mU; rG; mA; rU; mG; rC; mA; rG; mG; rA; mC; rU; mC; zc3p; zc3p$ | 2,4,6,8,10,12, 14,16,18-2'-OMe-3'-Pi | 1,3,5,7,9,11,13,15, 17,19-2'-OMe-3'-Pi; 20-C3; C3 |

Data in Table 4 shows that the most pronounced activity increase is obtained when C3C3 is present at the 3' termini of both antisense and sense strands (2) compared to blunt (1) and to C3-C3 on only one of the strands (3 or 4).

TABLE 5

| No. | Compound name | Concentration | % Residual target mRNA | Sense 5->3<br>Antisense 5->3 | sense modifications | antisense modifications |
|---|---|---|---|---|---|---|
| 1 | CASP2_4_S953 | 20 nM<br>5 nM<br>1 nM | 30<br>17<br>13 | rG; rC; rC; rA; rG; rA; rA; rU; rG;<br>rU; rG; rG; rA; rA; rC; rU; rC;<br>LdC; rU$<br>rA; mG; rG; mA; rG; mU; rU;<br>mC; rC; rA; mC; rA; mU; rU;<br>mC; rU; mG; rG; mC; zc3p; zc3p | 18-L-DNA-3'-Pi | 2,4,6,8,11,13,15,<br>17,19-2'-OMe-<br>3'-Pi; 20-<br>C3; C3; Phosphate |
| 2 | CASP2_4_S1145 | 20 nM<br>5 nM<br>1 nM | 65<br>43<br>26 | rG; rC; rC; rA; rG; rA; rA; rU; rG;<br>rU; rG; rG; rA; rA; rC; rU; rC;<br>LdC; rU$<br>rA; mG; rG; mA; rG; mU; rU;<br>mC; rC; rA; mC; rA; mU; rU;<br>mC; rU; mG; rG; mC; zc3p$ | 18-L-DNA-3'-Pi | 2,4,6,8,11,13,15,<br>17,19-2'-OMe-<br>3'-Pi; 20-<br>C3 |
| 3 | CASP2_4_S1146 | 20 nM<br>5 nM<br>1 nM | 57<br>43<br>26 | rG; rC; rC; rA; rG; rA; rA; rU; rG;<br>rU; rG; rG; rA; rA; rC; rU; rC;<br>LdC; rU$<br>rA; mG; rG; mA; rG; mU; rU;<br>mC; rC; rA; mC; rA; mU; rU;<br>mC; rU; mG; rG; mC; zc3p; zc3p;<br>zc3p$ | 18-L-DNA-3'-Pi | 2,4,6,8,11,13,15,<br>17,19-2'-OMe-<br>3'-Pi; 20-<br>C3; C3; C3 |
| 4 | CASP2_4_S1147 | 20 nM<br>5 nM<br>1 nM | 48<br>26<br>13 | rG; rC; rC; rA; rG; rA; rA; rU; rG;<br>rU; rG; rG; rA; rA; rC; rU; rC;<br>LdC; rU$<br>rA; mG; rG; mA; rG; mU; rU;<br>mC; rC; rA; mC; rA; mU; rU;<br>mC; rU; mG; rG; mC; zc3p; zc3ps | 18-L-DNA-3'-Pi | 2,4,6,8,11,13,15,<br>17,19-2'-OMe-<br>3'-Pi; 20-<br>C3; C3-3'ps;<br>Phosphate |
| 5 | CASP2_4_S505 | 20 nM<br>5 nM<br>1 nM | 52<br>48<br>22 | rG; rC; rC; rA; rG; rA; rA; rU; rG;<br>rU; rG; rG; rA; rA; rC; rU; rC;<br>LdC; rU$<br>rA; mG; rG; mA; rG; mU; rU;<br>mC; rC; rA; mC; rA; mU; rU;<br>mC; rU; mG; rG; mC$ | 18-L-DNA-3'-Pi | 2,4,6,8,11,13,15,<br>17,19-2'-OMe-<br>3'-Pi |

Data in Table 5 shows that 1) the presence of a C3OH (2) or C3Pi-C3Pi-C3OH (3) moiety on the antisense strand does not improve activity compared to blunt siRNA (5) and 2) the presence of C3Pi-C3Pi (1) and C3Pi-C3Ps (4) moieties on the antisense strand improves activity compared to blunt ended compounds and the effect is more pronounced with C3Pi-C3Pi.

TABLE 6

| No. | Compound name | concentration | Residual target mRNA % | Sense 5->3<br>Antisense 5->3 | sense modifications | antisense modifications |
|---|---|---|---|---|---|---|
| 1 | CASP2_25_S1005 | 50<br>20<br>5 | 15<br>35<br>45 | rG; mA; rA; mU; rG; mU; rG; mG; rA;<br>mA; rC; mU; rC; mC; rU; mC; rA; mA;<br>rC; zidB$<br>mG; rU; mU; rG; mA; rG; mG; rA; mG;<br>rU; mU; rC; mC; rA; mC; rA; mU; rU;<br>mC; zidB$ | 2,4,6,8,10,12,<br>14,16,18-<br>2'-OMe-3'-<br>Pi; 20-cap-<br>idAb | 1,3,5,7,9,11,13,<br>15,17,19-2'-<br>OMe-3'-Pi; 20-<br>cap-idAb |
| 2 | CASP2_25_S1006 | 50<br>20<br>5 | 38<br>38<br>81 | rG; mA; rA; mU; rG; mU; rG; mG; rA;<br>mA; rC; mU; rC; mC; rU; mC; rA; mA;<br>rC; zidB$<br>mG; rU; mU; rG; mA; rG; mG; rA; mG;<br>rU; mU; rC; mC; rA; mC; rA; mU; rU;<br>mC$ | 2,4,6,8,10,12,<br>14,16,18-<br>2'-OMe-3'-<br>Pi; 20-cap-<br>idAb | 1,3,5,7,9,11,13,<br>15,17,19-2'-<br>OMe-3'-Pi |
| 3 | CASP2_25_S1007 | 50<br>20<br>5 | 24<br>46<br>96 | rG; mA; rA; mU; rG; mU; rG; mG; rA;<br>mA; rC; mU; rC; mC; rU; mC; rA; mA;<br>rC$<br>mG; rU; mU; rG; mA; rG; mG; rA; mG;<br>rU; mU; rC; mC; rA; mC; rA; mU; rU;<br>mC; zidB$ | 2,4,6,8,10,12,<br>14,16,18-<br>2'-OMe-3'-<br>Pi | 1,3,5,7,9,11,13,<br>15,17,19-2'-<br>OMe-3'-Pi; 20-<br>cap-idAb |
| 4 | CASP2_25_S73 | 50<br>20<br>5 | 20<br>56<br>64 | rG; mA; rA; mU; rG; mU; rG; mG; rA;<br>mA; rC; mU; rC; mC; rU; mC; rA; mA;<br>rC$ | 2,4,6,8,10,12,<br>14,16,18-<br>2'-OMe-3'- | 1,3,5,7,9,11,13,<br>15,17,19-2'-<br>OMe-3'-Pi |

TABLE 6-continued

| Compound No. | name | concentration | Residual target mRNA % | Sense 5->3 Antisense 5->3 | sense modifications | antisense modifications |
|---|---|---|---|---|---|---|
| | | | | mG; rU; mU; rG; mA; rG; mG; rA; mG; rU; mU; rC; mC; rA; mC; rA; mU; rU; mC$ | | Pi |

Data in table 6 shows that a compound with an inverted deoxy abasic moiety on both sense and antisense strand (1) was more active then blunt ended compound (4) or compound with inverted abasic on one of the strands (2 or 3).

TABLE 7

| No. | Compound name | Concentration | Residual target mRNA % | Sense 5->3 Antisense 5->3 | Sense Description | Antisense Description |
|---|---|---|---|---|---|---|
| 1 | CASP2_4_S1001 | 50<br>20<br>5 | 18<br>22<br>43 | rG; mC; rC; mA; rG; mA; rA; mU; rG; mU; rG; mG; rA; mA; rC; mU; rC; mC; rU; zidB$<br>rA; mG; rG; mA; rG; mU; rU; mC; rC; rA; mC; rA; mU; rU; mC; rU; mG; rG; mC$ | 2,4,6,8,10,12,14,16,18-2'-OMe-3'-Pi; 20-cap-idAb | 2,4,6,8,11,13,15,17,19-2'-OMe-3'-Pi |
| 2 | CASP2_4_S1002 | 50<br>20<br>5 | 28<br>35<br>50 | rG; mC; rC; mA; rG; mA; rA; mU; rG; mU; rG; mG; rA; mA; rC; mU; rC; mC; rU$<br>rA; mG; rG; mA; rG; mU; rU; mC; rC; rA; mC; rA; mU; rU; mC; rU; mG; rG; mC; zidB$ | 2,4,6,8,10,12,14,16,18-2'-OMe-3'-Pi | 2,4,6,8,11,13,15,17,19-2'-OMe-3'-Pi; 20-cap-idAb |
| 3 | CASP2_4_S1000 | 50<br>20<br>5 | 16<br>21<br>44 | rG; mC; rC; mA; rG; mA; rA; mU; rG; mU; rG; mG; rA; mA; rC; mU; rC; mC; rU; zidB$<br>rA; mG; rG; mA; rG; mU; rU; mC; rC; rA; mC; rA; mU; rU; mC; rU; mG; rG; mC; zidB$ | 2,4,6,8,10,12,14,16,18-2'-OMe-3'-Pi; 20-cap-idAb | 2,4,6,8,11,13,15,17,19-2'-OMe-3'-Pi; 20-cap-idAb |
| 4 | CASP2_4_S1003 | 50<br>20<br>5 | 11<br>18<br>26 | zidB; rG; rC; rC; rA; rG; rA; rA; rU; rG; rU; rG; rG; rA; rA; rC; rU; rC; rC; rU; zidB$<br>rA; mG; rG; mA; rG; mU; rU; mC; rC; rA; mC; rA; mU; rU; mC; rU; mG; rG; mC; zidB$ | 0,20-cap-idAb | 2,4,6,8,11,13,15,17,19-2'-OMe-3'-Pi; 20-cap-idAb |
| 5 | CASP2_4_S1004 | 50<br>20<br>5 | 23<br>36<br>32 | zidB; rG; rC; rC; rA; rG; rA; rA; rU; rG; rU; rG; rG; rA; rA; rC; rU; rC; rC; rU; zidB$<br>rA; mG; rG; mA; rG; mU; rU; mC; rC; rA; mC; rA; mU; rU; mC; rU; mG; rG; mC$ | 0,20-cap-idAb | 2,4,6,8,11,13,15,17,19-2'-OMe-3'-Pi |

Data in Table 7 shows that double stranded RNA compounds having a terminal cap (inverted deoxyabsic mioiety) at both the 3' terminus of the antisense strand and 3' terminus of the sense strand exhibit enhanced activity when compared to a dsRNA compound having a 3' terminal cap covalently attached to the 3' termunis of the antisense strand (compare compounds 2 and 3 and compounds 4 and 5).

TABLE 8

| Compound No | name | concentration | Residual target mRNA % | Sense 5->3 Antisense 5->3 | Sense Description | Antisense Description |
|---|---|---|---|---|---|---|
| 1 | Myd88_11_S1262 | 20 nM<br>5 nM<br>1 nM<br>0.5 nM<br>0.1 nM | 7<br>7<br>20<br>16<br>45 | rG; rA; rA; rU; rG; rU; rG; rA; rC; rU; rU; rC; rC; rA; rG2p; rA2p; rC2p; rC2p; rA$<br>mU; rG; rG; mU; mC; mU; rG; rG; mA; rA; rG; mU; mC; rA; mC; rA; mU; mU; mC; zc3p; zc3p$ | 15,16,17,18-2'-5'-bridge | 1,4,5,6,9,12,13,15,17,18,19-2'-OMe-3'-Pi; 20-C3; C3 |
| 2 | Myd88_11_S1266 | 20 nM<br>5 nM<br>1 nM<br>0.5 nM<br>0.1 nM | 11<br>11<br>9<br>10<br>126 | rG; rA; rA; rU; rG; rU; rG; rA; rC; rU; rU; rC; rC; rA; rG2p; rA2p; rC2p; rC2p; rA2p<br>mU; rG; rG; mU; mC; mU; rG; rG; mA; rA; rG; mU; mC; rA; mC; rA; mU; mU; mC; zc3p; zc3p$ | 15,16,17,18,19-2'-5'-bridge; Phosphate | 1,4,5,6,9,12,13,15,17,18,19-2'-OMe-3'-Pi; 20-C3; C3 |

TABLE 8-continued

| Compound No | name | concentration | Residual target mRNA % | Sense 5->3 Antisense 5->3 | Sense Description | Antisense Description |
|---|---|---|---|---|---|---|
| 3 | Myd88_11_S1270 | 20 nM | 5 | zc3p; rG; rA; rA; rU; rG; rU; rG; | 15,16,17,18,19- | 1,4,5,6,9,12, |
| | | 5 nM | 6 | rA; rC; rU; rU; rC; rC; rA; rG2p; | 2'-5'- | 13,15,17,18, |
| | | 1 nM | 10 | rA2p; rC2p; rC2p; rA2p | bridge; 0-cap- | 19-2'-OMe- |
| | | 0.5 nM | 31 | mU; rG; rG; mU; mC; mU; rG; | C3; Phosphate | 3'-Pi; 20- |
| | | 0.1 nM | 47 | rG; mA; rA; rG; mU; mC; rA; | | C3; C3 |
| | | | | mC; rA; mU; mU; mC; zc3p; zc3p$ | | |
| 4 | Myd88_11_S1274 | 20 nM | 6 | zc6Np; rG; rA; rA; rU; rG; rU; rG; | 15,16,17,18,19- | 1,4,5,6,9,12, |
| | | 5 nM | 8 | rA; rC; rU; rU; rC; rC; rA; rG2p; | 2'-5'- | 13,15,17,18, |
| | | 1 nM | 15 | rA2p; rC2p; rC2p; rA2p | bridge; 0-cap- | 19-2'-OMe- |
| | | 0.5 nM | 22 | mU; rG; rG; mU; mC; mU; rG; | AmC6; | 3'-Pi; 20- |
| | | 0.1 nM | 63 | rG; mA; rA; rG; mU; mC; rA; | Phosphate | C3; C3 |
| | | | | mC; rA; mU; mU; mC; zc3p; zc3p$ | | |
| 5 | Myd88_11_S1276 | 20 nM | 11 | rG; rA; rA; rU; rG; rU; rG; rA; rC; | — | 1,4,5,6,9,12, |
| | | 5 nM | 20 | rU; rU; rC; rC; rA; rG; rA; rC; | | 13,15,17,18, |
| | | 0.5 nM | 57 | rC; rA$ | | 19-2'-OMe- |
| | | | | mU; rG; rG; mU; mC; mU; rG; | | 3'-Pi; 20- |
| | | | | rG; mA; rA; rG; mU; mC; rA; | | C3; C3 |
| | | | | mC; rA; mU; mU; mC; zc3p; zc3p$ | | |
| 6 | Myd88_11_S1159 | 20 nM | 12 | zidB; rG; rA; rA; rU; rG; rU; rG; | 15,16,17,18- | 1,4,5,6,9,12, |
| | | 5 nM | 9 | rA; rC; rU; rU; rC; rC; rA; rG2p; | 2'-5'-bridge; 0- | 13,15,17,18, |
| | | 1 nM | | rA2p; rC2p; rC2p; rA$ | cap-idAb | 19-2'-OMe- |
| | | 0.5 nM | 24 | mU; rG; rG; mU; mC; mU; rG; | | 3'-Pi; 20- |
| | | 0.1 nM | 57 | rG; mA; rA; rG; mU; mC; rA; | | C3; C3 |
| | | | | mC; rA; mU; mU; mC; zc3p; zc3p$ | | |
| 7 | Myd88_11_S1224 | 20 nM | 6 | zc3p; rG; rA; rA; dT; rG; dT; rG; | 4,6,9,10,11,12, | 1,4,5,6,9,12, |
| | | 5 nM | 13 | rA; dC; dT; dT; dC; dC; rA; rG; | 13,17,18- | 13,15,17,18, |
| | | 1 nM | 33 | rA; dC; dC; rA$ | DNA-3'-Pi; 0- | 19-2'-OMe- |
| | | 0.5 nM | 37 | mU; rG; rG; mU; mC; mU; rG; | cap-C3 | 3'-Pi; 20- |
| | | 0.1 nM | 88 | rG; mA; rA; rG; mU; mC; rA; | | C3; C3 |
| | | | | mC; rA; mU; mU; mC; zc3p; zc3p$ | | |
| 8 | RAC1_2_S1324 | 20 nM | 39 | rG; mA; rG; mU; rC; mC; rU; | 2,4,6,8,10,12, | 1,3,5,7,9,11, |
| | | 5 nM | 21 | mG; rC; mA; rU; mC; rA; mU; | 14,16,18-2'- | 13,15,17,19- |
| | | 1.25 nM | 9 | rU; mU; rG; mA; rA; zc3p; zc3p$ | OMe-3'- | 2'-OMe-3'- |
| | | 0.31 nM | 27 | mU; rU; mC; rA; mA; rA; mU; | Pi; 20-C3; C3 | Pi; 20- |
| | | | | rG; mA; rU; mG; rC; mA; rG; | | C3; C3; |
| | | | | mG; rA; mC; rU; mC; zc3p; zc3p | | Phosphate |
| 9 | RAC1_2_S1323 | 20 nM | 68 | rG; mA; rG; mU; rC; mC; rU; | 2,4,6,8,10,12, | 1,3,5,7,9,11, |
| | | 5 nM | 26 | mG; rC; mA; rU; mC; rA; mU; | 14,16,18-2'- | 13,15,17,19- |
| | | 1.25 nM | 10 | rU; mU; rG; mA; rA$ | OMe-3'-Pi | 2'-OMe-3'- |
| | | 0.1 nM | 6 | mU; rU; mC; rA; mA; rA; mU; | | Pi; 20- |
| | | | | rG; mA; rU; mG; rC; mA; rG; | | C3; C3; |
| | | | | mG; rA; mC; rU; mC; zc3p; zc3p | | Phosphate |

Data in Table 8 shows that double stranded RNA compounds comprising a 3' terminal C3Pi-C3OH overhang covalently attached to the 3' terminus of the antisense strand (guide strand) (Z=two C3 moieties) show excellent activity (greater than 80% knock down at 20 nM) irrespective of the modifications on the complementary sense strand (see compounds 1-7).

Compounds 1-7 utilize sequences set forth in SEQ ID NOS:3 and 4 and comprise a common antisense strand (SEQ ID NO:4) that includes two 3' terminal C3 moieties (C3Pi-C3OH) covalently attached to the 3' terminal nucleotide and different sense strands which include various modifications disclosed in the present application. Compound 1 sense strand includes unmodified ribonucleotides in positions 1-14 and 19 and 2'5' ribonucleotides in positions 15-18. Compound 2 sense strand includes unmodified ribonucleotides in positions 1-14 and 2'5' ribonucleotides in positions 15-19 and includes a terminal phosphate (P(O)$_3$). Compound 3 sense strand includes unmodified ribonucleotides in positions 1-14 and 2'5' ribonucleotides in positions 15-19 and includes a 3' terminal C3Pi. Compound 4 sense strand includes unmodified ribonucleotides in positions 1-14 and 2'5' ribonucleotides in positions 15-19 and includes a 3' terminal amino C6 moiety covalently attached to the 3' terminal nucleotide. Compound 5 sense strand includes unmodified ribonucleotides in positions 1-19 (each N' is unmodified). Compound 6 sense strand includes unmodified ribonucleotides in positions 1-14 and 19 and 2'5' ribonucleotides in positions 15-18 and includes a 3' terminal inverted abasic moiety covalently attached to the 3' terminal nucleotide. Compound 7 sense strand includes unmodified ribonucleotides in positions 1-3,5,7-8, 14-16 and 19 and deoxyribonucleotides in positions 4, 6, 9, 10-13 and 17-18 and includes a 3' terminal phosphate (Pi) and a C3OH moiety covalently attached at the 5' terminus of the inverted abasic moiety covalently attached to the 3' terminal nucleotide.

Compound 9 having two C3 moieties covalently attached to the 3' terminus of the sense strand and of the antisense strand is more active than a similar compound (8) having two C3 moieties covalently attached to the 3' terminus of the antisense strand.

Example 2

Delivery of Modified Nucleic Acid Molecules Targeting CASP2 to the Retina

Assessment of Target Cell siRNA Delivery, Target Cell Gene Knockdown Activity and Specificity of Cleavage of Target Gene mRNA Knock Down of Target Gene is Measured in Target Tissue for Example Following Intravitreal Injection into the Rat Retina.

Background Different structural modifications were made in the siRNA targeting the CASP2 gene, which are tested for exonuclease resistance. The aim of this study is to examine the in vivo distribution and activity of the oligonucleotides including these modifications as described below.

```
S1003    inv-dAb-GCCAGAAUGUGGAACUCCU-inv-dAb

AGGAGUUCCACAUUCUGGC-inv-dAb

S800     GCCAGAAUGUGGAACUCCU

AGGAGUUCCACAUUCUGGC-C3Pi-C3OH
```

Description of the test material (S1003): RNA duplex with the following structure: Sense strand non-modified 19 mer with inverted-Abasic as 5' and 3'-cap. Anti-Sense strand 19-mer with 2'O-Me at positions 2, 4, 6, 8, 11, 13, 15, 17 & 19 and with inverted Abasic as 3'-cap, Annealed. Quantity supplied: 336 µg Storage Conditions: −80° C.

Description of the test material (S800): RNA duplex with the following structure: Sense strand 19-mer with L-DNA at position 18. Anti-Sense strand 19-mer with 2'OMe at positions 2, 4, 6, 8, 11, 13, 15, 17 & 19 and two (CH2)3 propanediol at 3' end (C3Pi-C3OH). Quantity supplied: 840 µg. Storage Conditions: −80° C.

CNL: RNA duplex having same modifications as S800 without a C3Pi-C3OH moiety attached to the 3' terminus.

Animals: Age: 6-8 week old male rats. 180-220 gr

Group Size: n=4/10; Total number of animals: 112

Animal Husbandry Diet: Animals were provided an ad libitum commercial rodent diet (Harlan Teklad diet for rodents), and free access to drinking water.

Environment:
(i) Acclimatization of at least 5 days.
(ii) All the animals were confined in a limited access facility with environmentally controlled housing conditions throughout the entire study period, and maintained in accordance with HBI approved standard operating procedures (SOPs). Automatically controlled environmental conditions are set to maintain temperature at 20-24° C. with a relative humidity (RH) of 30-70%, a 12-hr light/12-hr dark cycle and 15-30 air changes/hr in the study room. Temperature, RH and the light cycle were monitored by the control computer.

Experimental Design is Provided in Table 2-1

| Group No. | Delivery Route Unilateral (LE) | SiRNA Type | Dose regime µg/10 µl/eye | Time point (days) | Group Size |
|---|---|---|---|---|---|
| I | IVT | S1003 | 20 µg/10 µl | 1 | 4 |
| II | IVT | S1003 | 20 µg/10 µl | 3 | 4 |
| III | IVT | S1003 | 20 µg/10 µl | 7 | 4 |
| IV | IVT | S800 | 20 µg/10 µl | 1 | 10 |
| V | IVT | S800 | 20 µg/10 µl | 3 | 10 |
| VI | IVT | S800 | 20 µg/10 µl | 7 | 10 |
| VII | IVT | CNL | 20 µg/10 µl | 1 | 10 |
| VIII | IVT | CNL | 20 µg/10 µl | 3 | 10 |
| IX | IVT | CNL | 20 µg/10 µl | 7 | 10 |
| X | IVT | Vehicle | 10 µl | 1 | 10 |
| XI | IVT | Vehicle | 10 µl | 3 | 10 |
| XII | IVT | Vehicle | 10 µl | 7 | 10 |
| XIII | Intact | — N/A | — N/A | N/A | 10 |

Study design: All animals from experimental groups I-XII were injected IVT unilaterally into the Left Eye (LE)) at dose of 20 µg of test article or control (CNL) in 10 µl PBS vehicle or 10 µl vehicle only. Experimental group XIII will be used as intact control. The termination step will be accomplished according to the study design (1 day, 3 days and 7 days after IVT treatment).

Anesthesia: Animals were anesthetized with an Isoflurane special circuit system (Stoelting, USA). Pupils will be dilated with Mydramid (0.5% tropicamide) eye drops. For additional topical anesthesia, will be used Localin (OXYBUPROCAINE HYDROCHLORIDE 0.4%). The Lacromycin (Gentamycin Sulfate (Equivalent to 0.3% Gentamycin base) ophthalmic solution to prevent/decrease post surgery inflammatory process.

Intravitreal injection was performed under a dissecting microscope. A 30/33-gauge needle was used to make a punch incision 1 mm posterior to the temporal limbus, and a syringe needle (30/33-gauge Insulin syringe 0.3 ml, PIC 0.8 mm, Italy) was inserted through the incision, 1.5 mm deep, as observed through the dilated pupil.

Scheduled euthanasia All animals were deeply anesthetized (Equithesine 4 ml/kg I.P) and euthanized (decapitated) according to the study design (Table, Termination).

Tissue Collection: Both eyes from all animals were enucleated and stored on ice. The eyes will be dissected using a microscope, and gross pathologies will be graded according to sample grading scale (see appendix 5 for "Eye Pathology Score"). The cornea will be punctured using a 27/30G needle, to remove aqueous humor from the anterior chamber. Using a microsurgical blade, a cut will be made along the limbus, and the cornea and the lens removed. The remaining eyecup will be opened by a sagittal cut through the sclera. The retina will be extracted from the eyecup, rinsed in PBS and separated. Using fine-tip forceps the retina will be collected into the appropriate test tube, frozen in liquid nitrogen, and transferred to the Molecular Biology Unit for extraction of total RNA.

Evaluation

Knockdown activity of the siRNA targeting CASP2 in the rat retina was determined by CASP2 mRNA expression level quantification using the qPCR method. CASP2_4 siRNA cleavage site on the target gene will be verified by RACE and siRNA quantitation in the retina was performed by S&L qPCR (stem and loop qPCR).

Samples RNA Isolation: RNA were processed from retina samples according to standard procedures for total RNA isolation with EZRNA, by double extraction. CASP2_4 siRNA quantification by qPCR: The delivery of the CASP2_4 siRNA in the retina was measured by qPCR siRNA quantification. qPCR was performed according to standard methods using SYBR Green method on Applied Biosystem 7300 PCR System. CASP2_4 siRNA directed cleavage of CASP2 mRNA in rat retina was determined by the detection of the cleavage product using the RACE (Rapid Amplification of cDNA Ends) method in the respective experimental groups. If evidence of the expected cleavage product is shown, the siRNA cleavage site on the target gene will be verified by sequence analysis and optionally the cleavage product will be quantified using qPCR. CASP2 mRNA quantification by qPCR: after cDNA is prepared CASP2 knock down will be verified by CASP2 mRNA quantification by qPCR. qPCR will be performed according to standard methods standard methods using SYBR Green method on Applied Biosystem 7300 PCR System.

Preliminary Results

Preliminary results indicate that the S800 is taken up more efficiently into the retinal cells than S1003. Results are shown in Table 2-2, below

TABLE 2-2

| eye | Structure | Days | N | Mean | Std |
|---|---|---|---|---|---|
| Left | CASP2_4_S1003 | 1 | 4 | 3.54 | 5.29 |
| | CASP2_4_S1003 | 3 | 4 | 0.44 | 0.67 |
| | CASP2_4_S1003 | 7 | 4 | 0.27 | 0.17 |
| | CASP2_4_S800 | 1 | 10 | 26.16 | 17.65 |
| | CASP2_4_S800 | 3 | 10 | 1.52 | 1.93 |
| | CASP2_4_S800 | 7 | 10 | 0.81 | 0.74 |
| | CASP2_4 CNL | 1 | 10 | 2.53 | 2.31 |
| | CASP2_4 CNL | 3 | 10 | 1.06 | 0.76 |
| | CASP2_4 CNL | 7 | 9 | 0.10 | 0.08 |
| Right | CASP2_4_S1003 | 1 | 4 | 0.01 | 0.00 |
| | CASP2_4_S1003 | 3 | 3 | 0.01 | 0.01 |
| | CASP2_4_S1003 | 7 | 4 | 0.02 | 0.02 |
| | CASP2_4_S800 | 1 | 10 | 0.14 | 0.26 |
| | CASP2_4_S800 | 3 | 10 | 0.18 | 0.41 |
| | CASP2_4_S800 | 7 | 10 | 0.10 | 0.09 |
| | CASP2_4 CNL | 1 | 10 | 0.05 | 0.07 |
| | CASP2_4 CNL | 3 | 10 | 0.01 | 0.01 |
| | CASP2_4 CNL | 7 | 9 | 0.01 | 0.01 |

Example 3

Delivery of Modified Nucleic Acid Molecules Targeting MYD88 to the Retina

Assessment of Target Cell siRNA DeliveryThe objectives of the study are:

1.1 To determine delivery of MYD88_11 siRNA of different structures and modifications to the rat retina 4 hours, one day and three days following unilateral Intravitreal (IVT) injections.

1.2 To determine knockdown activity of the MYD88_11 siRNA of different structures targeting MYD88 by means of qPCR of MYD88 mRNA after IVT injection in the rat eyes 4 hours, one day and three days after IVT injections.

Background Different structural modifications were made in the siRNA targeting the CASP2 gene, which are tested for exonuclease resistance. The aim of this study is to examine the in vivo distribution of double stranded RNA oligonucleotides with modifications as disclosed herein, specifically the modifications described below.

MYD88_11 S505    5' GAAUGUGACUUCCAGAC<u>c</u>A

5' U<u>GGUCUGGAAGUCACA</u>UUC

MYD88_11 S1159   5' idAb-GAAUGUGACUUCCA*GACC*A

5' U<u>GGUCUGGAAGUCACA</u>UUC-C3Pi-

C3OH

MYD88_11 S1270   5' OHC3-GAAUGUGACUUCCA*GACCA*-Pi

5' U<u>GGUCUGGAAGUCACA</u>UUC-C3Pi-

C3OH

Description of the test material 5505: RNA duplex with the following structure: Sense strand Non-modified 19 mer with one L-DNA moiety in position 18 (lower case bold).

Anti-Sense strand 19-mer with 2'O-Me at positions 2, 4, 6, 8, 11, 13, 15, 17 & 19 Annealed. Storage Conditions: −80° C.

Description of the test material S1159: RNA duplex with the following structure: Sense strand 19-mer with inverted-Abasic as 5' cap and 2'-5' bridged RNA at positions 15-18 The antisense strand is a 19-mer with 2'O-Me at positions 1, 4-6, 9, 12-13, 15, 17-19 and two constitutive unites of 1,3-Propanediol bond by phosphodiester bond at the 3' end).

Annealed. Storage Conditions: −80° C.

Description of the test material S1270: RNA duplex with the following structure: Sense strand 19-mer with 2'5' nucleotides in positions 15-19 and a terminal phosphate (Pi). Anti-Sense strand 19-mer with 2'OMe at positions 1, 4, 5, 6, 9, 12, 13, 15, 17-19 and two (CH2)3 propanediol at 3' end (C3Pi-C3OH). Annealed. Storage Conditions: −80° C.

Animals: Age: 8-10 week old male rats. 180-220 gr

Group Size: n=4/8; Total number of animals: 104

Animal Husbandry Diet: Animals were provided an ad libitum commercial rodent diet (Harlan Teklad diet for rodents), and free access to drinking water.

Environment:

(i) Acclimatization of at least 5 days.

(ii) All the animals were confined in a limited access facility with environmentally controlled housing conditions throughout the entire study period, and maintained in accordance with HBI approved standard operating procedures (SOPs). Automatically controlled environmental conditions are set to maintain temperature at 20-24° C. with a relative humidity (RH) of 30-70%, a 12-hr light/12-hr dark cycle and 15-30 air changes/hr in the study room. Temperature, RH and the light cycle were monitored by the control computer.

Study design: All animals from experimental groups 1-12 were injected IVT unilaterally into the Left Eye (LE)) at dose of 20 μg of test article or 10 μl PBS vehicle only. Experimental group 13 was used as intact control. The termination step was accomplished according to the study design (4 hours, 1 day, and 7 days after IVT treatment).

Experimental Design is Provided in Table 3-1

TABLE 3-1

| Group No. | Delivery Route Unilateral (LE) | SiRNA Type | Dose regime μg/eye | Time point (hours) | Group Size |
|---|---|---|---|---|---|
| 1 | IVT | MYD88_11_S505 | 20 μg/10 μl | 4 | 8 |
| 2 | IVT | MYD88_11_S505 | 20 μg/10 μl | 24 | 8 |
| 3 | IVT | MYD88_11_S505 | 20 μg/10 μl | 168 | 8 |
| 4 | IVT | MYD88_11_S1159 | 20 μg/10 μl | 4 | 8 |
| 5 | IVT | MYD88_11_S1159 | 20 μg/10 μl | 24 | 8 |
| 6 | IVT | MYD88_11_S1159 | 20 μg/10 μl | 168 | 8 |
| 7 | IVT | MYD88_11_S1270 | 20 μg/10 μl | 4 | 8 |
| 8 | IVT | MYD88_11_S1270 | 20 μg/10 μl | 24 | 8 |
| 9 | IVT | MYD88_11_S1270 | 20 μg/10 μl | 168 | 8 |
| 10 | IVT | PBS | 10 μl | 4 | 8 |
| 11 | IVT | PBS | 10 μl | 24 | 8 |
| 12 | IVT | PBS | 10 μl | 168 | 8 |
| 13 | Intact | — N/A | — N/A | N/A | 8 |

Study design: All animals from experimental groups 1-12 were injected IVT unilaterally into the Left Eye (LE)) at dose of 20 μg of test article or 10 μl PBS vehicle only. Experimental group 13 was used as intact control. The termination step was accomplished according to the study design (4 hours, 1 day, and 7 days after IVT treatment).

Anesthesia: Animals were anesthetized with an Isoflurane special circuit system (Stoelting, USA) working setup: 3-4.5% Isoflurane in $O_2$ at 600-800 ml/min $O_2$ flow rate. Pupils were dilated with Mydramid (0.5% tropicamide) eye drops. For additional topical anesthesia, will be used Localin (OXYBUPROCAINE HYDROCHLORIDE 0.4%). The Lacromycin (Gentamycin Sulfate (Equivalent to 0.3% Gentamycin base) ophthalmic solution to prevent/decrease post surgery inflammatory process.

Intravitreal injection was performed under a dissecting microscope. A 30/33-gauge needle was used to make a punch incision 1 mm posterior to the temporal limbus, and a syringe needle (30/33-gauge Insulin syringe 0.3 ml,PIC 0.8 mm, Italy) was inserted through the incision, 1.5 mm deep, as observed through the dilated pupil.

Scheduled euthanasia All animals were deeply anesthetized (Equithesine 4 ml/kg I.P) and euthanized (decapitated) according to the study design (Table, Termination).

Tissue Collection: Both eyes from all animals were enucleated and stored on ice. The eyes will be dissected using a microscope, and gross pathologies will be graded according to sample grading scale (see appendix 5 for "Eye Pathology Score"). The cornea will be punctured using a 27/30G needle, to remove aqueous humor from the anterior chamber. Using a microsurgical blade, a cut will be made along the limbus, and the cornea and the lens removed. The remaining eyecup will be opened by a sagittal cut through the sclera. The retina will be extracted from the eyecup, rinsed in PBS and separated. Using fine-tip forceps the retina will be collected into the appropriate test tube, frozen in liquid nitrogen, and total RNA was extracted.

Evaluation siRNA quantitation in the retina will be performed by Stem & Loop qPCR and Knockdown activity of the siRNA targeting MYD88 in the rat retina will be determined by MYD88 mRNA expression level quantification using qPCR.

RNA Isolation: RNA was processed from retina samples according to standard procedures using the EZ RNA kit.

MYDD88 siRNA quantification by qPCR: The delivery of the MYDD88 siRNA in the retina was measured by qPCR siRNA quantification (S&L). qPCR was performed according to standard procedures using the SYBR Green method on Applied Biosystem 7300 PCR System.

MYDD88 mRNA quantification by qPCR: cDNA was prepared using standard procedures and MYDD88 knock down will be verified by MYD88 mRNA quantification by qPCR. qPCR will be performed using SYBR Green method on Applied Biosystem 7300 PCR System.

Preliminary Results are provided in table 3-2, hereinbelow.

Delivery of the C3C3 modified compounds (S1159 and S1270) to retinal ganglion cells was significantly higher than delivery of the compound having blunt ends (S505) (see data provided in the "Median" column. Values are given as femtomolar).

TABLE 3-2

| retina | struct | termination | Delivery | N | Mean | S.D. | Median | p. value |
|---|---|---|---|---|---|---|---|---|
| Left | MYD88_11_S1159 | 4 | IVT | 8 | 174 | 121 | 148 | <.0001 |
|  | MYD88_11_S1270 |  |  | 8 | 442 | 219 | 466 |  |
|  | MYD88_11_S505 |  |  | 8 | 52 | 38 | 38 |  |
|  | MYD88_11_S1159 | 24 |  | 6 | 9 | 19 | 2 | 0.2928 |
|  | MYD88_11_S1270 |  |  | 5 | 37 | 74 | 5 |  |
|  | MYD88_11_S505 |  |  | 8 | 2 | 3 | 0 |  |
|  | MYD88_11_S1159 | 168 |  | 6 | 2 | 1 | 1 | 0.0034 |
|  | MYD88_11_S1270 |  |  | 5 | 3 | 2 | 2 |  |
|  | MYD88_1_S505 |  |  | 6 | 0 | 0 | 0 |  |
| Right | MYD88_11_S1159 | 4 | IVT | 4 | 2 | 1 | 1 | 0.0015 |
|  | MYD88_11_S1270 |  |  | 0 | * |  |  |  |
|  | MYD88_11_S505 |  |  | 7 | 0 | 0 | 0 |  |
|  | MYD88_11_S1159 | 24 |  | 4 | 14 | 23 | 2 | 0.3023 |
|  | MYD88_11_S1270 |  |  | 5 | 6 | 10 | 2 |  |
|  | MYD88_11_S505 |  |  | 6 | 0 | 0 | 0 |  |
|  | MYD88_11_S1159 | 168 |  | 7 | 6 | 10 | 1 | 0.2943 |
|  | MYD88_11_S1270 |  |  | 4 | 3 | 2 | 2 |  |
|  | MYD88_11_S505 |  |  | 7 | 0 | 0 | 0 |  |

Example 4

Model Systems of Acute Renal Failure (ARF)

ARF is a clinical syndrome characterized by rapid deterioration of renal function that occurs within days. Without being bound by theory the acute kidney injury may be the result of renal ischemia-reperfusion injury such as renal ischemia-reperfusion injury in patients undergoing major surgery such as major cardiac surgery. The principal feature of ARF is an abrupt decline in glomerular filtration rate (GFR), resulting in the retention of nitrogenous wastes (urea, creatinine) Recent studies, support that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum.

Testing an active siRNA compound was performed using an animal model for ischemia-reperfusion-induced ARF, as indicated in PCT patent application publication No. WO/2009/044392.

An existing siRNA can be advantageously modified and future siRNA can be designed and produced to provide active nucleic acid molecules. In a non-limiting example siRNA compounds which utilize the oligonucleotide pairs set forth in Tables B (B1-B74), Tables C($C_1$-$C_4$) and Tables D (D1-D34) of PCT Patent Publication No. WO/2009/044392, in particular siRNAs directed to specific proapoptotic genes, in particular to genes TP53BP2, LRDD, CYBA, ATF3, CASP2, HRK, CIQBP, BNIP3, MAPK8, MAPK14, RAC1, GSK3B, P2RX7, TRPM2, PARG, CD38, STEAP4, BMP2, CX43, TYROBP, CTGF, and SPP1) and further include and least one 3' overhang according to the present invention are tested in the above model system and found to be protective against ischemia reperfusion.

Example 5

Model Systems of Pressure Sores or Pressure Ulcers

Pressure sores or pressure ulcers including diabetic ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleoli, and heels are especially susceptible; other sites may be involved depending on the patient's situation.

Testing the active inhibitors of the invention (such as siRNA compounds) for treating pressure sore, ulcers and similar wounds is performed in the mouse model as described in Reid et al., J. Surg. Res. 116:172-180, 2004.

An additional rabbit model is described by Mustoe et al, JCI, 1991. 87(2):694-703; Ahn and Mustoe, Ann Pl Surg, 1991. 24(1):17-23, and is used for testing the siRNA compounds designed and synthesized as disclosed herein. An existing siRNA can be advantageously modified and future siRNA can be designed and produced to provide active nucleic acid molecules. In some embodiments siRNA compounds which utilize the oligonucleotide pairs set forth in Tables B (B1-B74), Tables C($C_1$-$C_4$) and Tables D (D1-D34) of PCT patent application publication No. WO/2009/044392, and specifically compounds directed to genes CIQBP, RAC1, GSK3B, P2RX7, TRPM2, PARG, CD38, STEAP4, BMP2, CX43, or TYROBP and further include and least one 3' non-nucleotide overhang according to the present invention are tested in animal models where it is shown that these siRNA compounds treat and prevent pressure sores and ulcers.

Example 6

Model Systems of Chronic Obstructive Pulmonary Disease (COPD)

Chronic obstructive pulmonary disease (COPD) is characterized mainly by emphysema, which is permanent destruction of peripheral air spaces, distal to terminal bronchioles. Emphysema is also characterized by accumulation of inflammatory cells such as macrophages and neutrophils in bronchioles and alveolar structures. Emphysema and chronic bronchitis may occur as part of COPD or independently.

Testing the active inhibitors of the invention (such as siRNA) for treating COPD/emphysema/chronic bronchitis is performed in animal models such as those disclosed as follows:

Starcher and Williams, 1989. Lab. Animals, 23:234-240; Peng, et al., 2004; Am J Respir Crit. Care Med, 169:1245-1251; Jeyaseelan et al., 2004. Infect. Immunol, 72: 7247-56. Additional models are described in PCT patent publication WO 2006/023544 assigned to the assignee of the present application, which is hereby incorporated by reference into this application.

An existing siRNA can be advantageously modified and future siRNA can be designed and produced to provide active nucleic acid molecules. In some embodiments siRNA compounds which utilize the oligonucleotide pairs set forth in Tables B (B1-B74), Tables C($C_1$-$C_4$) and Tables D (D1-D34) of PCT patent application publication No. WO/2009/044392, and in particular to siRNA to genes CIQBP, BNIP3, GSK3B, P2RX7, TRPM2, PARG, CD38, STEAP4, BMP2, CX43, TYROBP, CTGF, and DUOX1 and further include and least one 3' overhang as disclosed herein are tested in these animal models, which show that these siRNA compounds may treat and/or prevent emphysema, chronic bronchitis and COPD.

Example 7

Model Systems of Spinal Cord Injury

Spinal cord injury, or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases which can affect the spinal cord include polio, spina bifida, tumors and Friedreich's ataxia.

An existing siRNA can be advantageously modified and future siRNA can be designed and produced to provide active nucleic acid molecules. In some embodiments siRNA compounds which utilize the oligonucleotide pairs set forth in 7 Tables B (B1-B74), Tables C($C_1$-$C_4$) and Tables D (D1-D34) of PCT patent application publication No. WO/2009/044392, and in particular siRNA directed to genes LRDD, CYBA, ATF3, CASP2, HRK, CIQBP, BNIP3, MAPK8, MAPK14, RAC1, GSK3B, P2RX7, TRPM2, PARG, CD38, STEAP4, BMP2, CX43, TYROBP, CTGF, and RHOA and further include and least one 3' overhang as disclosed herein are tested in this animal model, which show that these siRNA compounds promote functional recovery following spinal cord injury and thus may be used to treat spinal cord injury.

Example 8

Model systems of Glaucoma

Testing the active inhibitors of the invention (such as siRNA) for treating or preventing glaucoma is done in the animal model for example as described by Pease et al., J. Glaucoma, 2006, 15(6):512-9 (Manometric calibration and comparison of TonoLab and TonoPen tonometers in rats with experimental glaucoma and in normal mice).

An existing siRNA can be advantageously modified and future siRNA can be designed and produced to provide active nucleic acid molecules. In some embodiments siRNA compounds which utilize the oligonucleotide pairs set forth in Tables B (B1-B74), Tables C (C1-C4) and Tables D (D1-D34) of PCT patent application publication No. WO/2009/044392, in particular to genes TP53BP2, LRDD, CYBA, ATF3, CASP2, HRK, BNIP3, MAPK8, MAPK14, RAC1, and RHOA and further include and least one 3' non-nucleotide overhang as disclosed herein are tested in this animal model which show that these siRNA compounds treat and/or prevent glaucoma.

Example 8A

Model Systems of Ischemic Optic Neuropathy (ION)

An animal model for Ischemic optic neuropathy was established in adults Wistar rats using a protocol of optic nerve crush injury. Seven days prior to the optic nerve crush, the retinal ganglion cells (RGC) are selectively labelled by application of the retrograde tracer FluoroGold (2%, Fluorochrome, Englewood, Colo.) to the superior colliculus. The tracer is transported by retrograde transport along RGC axons resulting in complete and specific labeling of all RGCs within 1 week post injection of the fluorescent tracer. The animals are subjected to the optic nerve crush injury 7 days post retrograde tracing. The orbital optic nerve is exposed through a supraorbital approach and all axons in the optic nerve are transected by crushing with forceps for 10 seconds, 2 mm from the lamina cribrosa. A single dose of 20 µg/5 µl of PBS of an siRNA compound according to the invention is microinjected into the vitreous body 2 mm anterior to the nerve head, using a glass micropipette at the time of the optic nerve crush. The survival of RGCs is determined 7 days following the optic nerve crush by counting FluoroGold-labelled RGCs on flat-mounted retinas. The experimental animals are perfused transcardially with 4% paraformaldehyde at 1 week after the optic nerve crash. Both retinas are dissected out, fixed for an additional 30 min and flat-mounted on a glass slide for ganglion cell layer quantification. The number of fluorescent RGCs is counted in 16 distinct areas in each retina and the percent of survival of the RGCs is determined compared to samples obtained from rats which did not undergo optic nerve crush injury at all or samples obtained from rats which were injected with PBS, control siRNA or GFP siRNA along with the optic nerve crush injury. Microglia cells that may have incorporated FluoroGold after phagocytosis of dying RGCs were distinguished by their characteristic morphology and excluded from quantitative analyses.

Another model of optic nerve axotomy where the entire population of RGCs are axotomized by transecting the optic nerve close to the eye is useful for testing the compounds and compositions of the present invention. (Cheng L, et al. *J. Neurosci.* May 15, 2002 2002; 22:3977-3986).

Example 9

Model Systems of Ischemia/Reperfusion Injury Following Lung Transplantation in Rats Testing the active inhibitors of the invention (such as siRNA) for treating or preventing ischemia/reperfusion injury or hypoxic injury following lung transplantation is done in one or more of the experimental animal models, for example as described by Mizobuchi et al., 2004. J. Heart Lung Transplant, 23:889-93; Huang, et al., 1995. J. Heart Lung Transplant. 14: S49; Matsumura, et al., 1995. Transplantation 59: 1509-1517; Wilkes, et al., 1999. Transplantation 67:890-896; Naka, et al., 1996. Circulation Research, 79: 773-783.

An existing siRNA can be advantageously modified and future siRNA can be designed and produced to provide active nucleic acid molecules. In some embodiments siRNA compounds which utilize the oligonucleotide pairs set forth in Tables B (B1-B74), Tables C (C1-C4) and Tables D (D1-D34) of PCT patent application publication No. WO/2009/044392, and in particular to TP53BP2, LRDD, CYBA, CASP2, BNIP3, RAC1, and DUOX1 and further include and least one 3' non-nucleotide overhang as disclosed herein are tested in these animal models, which show that these siRNA compounds treat and/or prevent ischemia-reperfusion injury following lung transplantation and thus may be used in conjunction with transplant surgery.

Example 10

Model Systems of Acute Respiratory Distress Syndrome

Testing the active inhibitors of the invention (such as siRNA) for treating acute respiratory distress syndrome is done in the animal model as described by Chen et al (J Biomed Sci. 2003; 10(6 Pt 1):588-92. siRNA compounds according to Tables B (B1-B74), Tables C (C1-C4) and Tables D (D1-D34) of PCT patent application publication No. WO/2009/044392, in particular to genes CYBA, HRK, BNIP3, MAPK8, MAPK14, RAC1, GSK3B, P2RX7, TRPM2, PARG, SPP1, and DUOX1 and further include and least one 3' overhang as disclosed herein are tested in this animal model which shows that these siRNAs treat and/or prevent acute respiratory distress syndrome and thus may be used to treat this condition.

Example 11

Animal Models of Osteoarthritis (OA)

Collagen induced arthritis (CIA): CIA in mice is described in Trentham et al. (1977. J. Exp. Med. 146: 857-868). Adjuvant-induced arthritis (AA):AA is described in Kong et al., (1999. Nature, 402:304-308). A menisectomy model is described in Han et al., (1999. Nagoya J Med Sci 62(3-4): 115-26).

The effect of different siRNA inhibitors, such as siRNA to SSP1, on different parameters related to OA such as chondrocyte proliferation, terminal differentiation and development of arthritis, is evaluated using one or more of the above models, in addition to in vitro models known in the art. siRNA compounds directed to specific proapoptotic genes, in particular to SSP1, and further include and least one 3' overhang as disclosed herein are tested in these animal models which show that these siRNAs treat and/or prevent OA and thus may be used to treat this condition.

Example 12

Rat Model Systems for Transplantation-Associated Acute Kidney Injury

Warm Ischemia—

In test rats a left nephrectomy is performed, followed by auto transplantation that results in a warm kidney graft preservation period of 45 minutes. Following auto transplantation, a right nephrectomy is performed on the same animal. Chemically modified siRNA to a target is administered intravenously via the femoral vein either before harvesting of the kidney graft (mimicking donor treatment) ("pre"), or after the kidney autotransplantation (mimicking recipient treatment), or both before harvest and after transplantation (combined donor and recipient treatment) ("pre-post").

Cold Ischemia—

A left nephrectomy is performed on a donor animal, followed by a cold preservation (on ice) of the harvested kidney for a period of 5 hours. At the end of this period, the recipient rat will undergo a bilateral nephrectomy, followed by transplantation of the cold-preserved kidney graft. The total warm ischemia time (including surgical procedure) is about 30 minutes. Chemically modified siRNA is administered intravenously via the femoral vein, either to the donor animal prior to the kidney harvest ("pre"), or to the recipient animal 15 minutes ("post 15 min") or 4 hours (post 4 hrs) post-transplantation.

To assess the efficacy of siRNA in improvement of post-transplantation renal function, serum creatinine levels are measured on days 1, 2, and 7 post-transplantation in both warm and cold ischemia models.

What is claimed is:

1. A double-stranded nucleic acid molecule comprising a sense strand and an antisense strand, wherein the antisense strand comprises a non-nucleotide overhang covalently attached via a phosphodiester or a phosphorothioate linkage to the 3' or to the 2' position of the sugar residue of the 3' terminal nucleotide,
wherein the non-nucleotide overhang is selected from the group consisting of C3Pi, C3Ps, C3Pi-C3OH, C3Pi-C3Pi, C3Pi-C3Ps, C3Ps-C3OH, C3Ps-C3Pi, C3Ps-C3Ps, C3Pi-C3Pi-C3OH, C3Ps-C3Ps-C3OH, C3Pi-C3Ps-C3OH, C3Ps-C3Pi-C3OH, C3Pi-C3Pi-C3Pi, C3Ps-C3Ps-C3Ps, C3Pi-C3Ps-C3Ps, C3Ps-C3Pi-C3Ps, C3Ps-C3Ps-C3Pi, C3Pi-C3Pi-C3Ps, C3Ps-C3Pi-C3Pi, C3Pi-C3Ps-C3Pi, C3Pi-C3Ps-C3Pi, C3Pi-rAb, C3Pi-dAb, C3Ps-rAb, C3Ps-dAb, rAbPi-C3OH, rAbPi-C3Pi, rAbPs-C3OH, rAbPs-C3Pi, dAbPi-C3OH, dAbPi-C3Pi, dAbPs-C3OH and dAbPs-C3Pi; and wherein each Pi is a phosphodiester linkage and each Ps is a phosphorothioate linkage;

or a pharmaceutically acceptable salt of such molecule.

2. The double-stranded nucleic acid molecule of claim 1 having structure (A1)

```
(A1)    5'        (N)x-Z 3'    (antisense strand)

3'     Z'-(N')y-z" 5'  (sense strand)
``` wherein each of N and N' is an unmodified ribonucleotide, a modified ribonucleotide, or an unconventional moiety;
wherein each of (N)x and (N')y is an oligonucleotide in which each consecutive N or N' is joined to the next N or N' by a covalent bond;
wherein Z comprises a non-nucleotide overhang covalently attached via a phosphate based linkage to the 3' position or the 2' position of the sugar residue of the 3' terminal nucleotide in the antisense strand;
wherein Z comprises a non-nucleotide overhang selected from the group consisting of C3Pi, C3Pi-C3OH, C3Pi-C3Pi, C3Pi-C3Ps, C3Ps, C3Ps-C3OH, C3Ps-C3Pi, C3Ps-C3Ps, C3Pi-C3Pi-C3OH, C3Ps-C3Ps-C3OH, C3Pi-C3Ps-C3OH, C3Ps-C3Pi-C3OH, C3Pi-C3Pi-C3Pi, C3Ps-C3Ps-C3Ps, C3Pi-C3Ps-C3Ps, C3Ps-C3Pi-C3Ps, C3Ps-C3Ps-C3Pi, C3Pi-C3Pi-C3Ps, C3Ps-C3Pi-C3Pi, C3Pi-C3Ps-C3Pi, C3Pi-rAb, C3Pi-dAb, C3Ps-rAb, C3Ps-dAb, rAbPi-C3OH, rAbPi-C3Pi, rAbPs-C3OH, rAbPs-C3Pi, dAbPi-C3OH, dAbPi-C3Pi, dAbPs-C3OH and dAbPs-C3Pi;
wherein each Pi is a phosphodiester linkage and each Ps is a phosphorothioate linkage;
wherein Z' is present or absent; but if present, Z' is an inorganic phosphate or a non-nucleotide overhang selected from the group consisting of an abasic moiety, an inverted abasic moiety and an alkyl moiety or a derivative thereof or a combination thereof; covalently attached via a phosphate based linkage to the 3' position or the 2' position of the sugar residue of the 3' terminal nucleotide in the sense strand;
wherein z" may be present or absent, but if present is a capping moiety covalently attached at the 5' terminus of (N')y;
wherein each of x and y is independently an integer between 18 and 40;
wherein the sequence of (N')y has complementarity to the sequence of (N)x; and wherein the sequence of (N)x has complementarity to a consecutive sequence in a target RNA;
or a pharmaceutically acceptable salt of such molecule.

3. The molecule of claim 2, wherein x=y=19.

4. The molecule of claim 2, wherein Z' is present.

5. The molecule of claim 2, wherein Z comprises a non-nucleotide overhang selected from the group consisting of C3Pi-C3OH, C3Pi-C3Pi, C3Pi-C3Ps, C3Ps-C3Pi, C3Ps-C3OH and C3Ps-C3Ps.

6. The molecule of claim 4, wherein Z' is a non-nucleotide overhang selected from the group consisting of C3OH, C3Pi and C3Ps, wherein Pi is a phosphodiester linkage and Ps is a phosphorothioate linkage.

7. A composition comprising the molecule of claim 1 or a pharmaceutically acceptable salt of such molecule, and a pharmaceutically acceptable carrier.

8. A method for treating a subject suffering from a disease or disorder associated with expression of a target gene comprising administering to the subject the molecule of claim 1 or a pharmaceutically acceptable salt of such molecule, in an amount effective to down-regulate expression of the target gene, thereby treating the subject.

9. The molecule of claim 1, wherein the non-nucleotide overhang is covalently attached to the 3' position of the sugar residue of the 3' terminal nucleotide such that the 3' terminal nucleotide has one of the following structures:

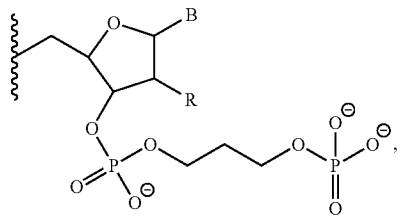

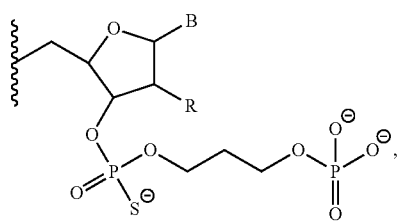

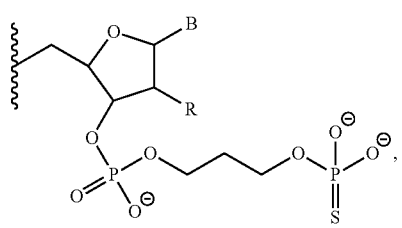

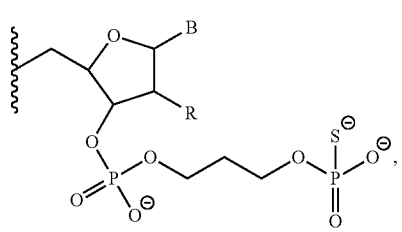

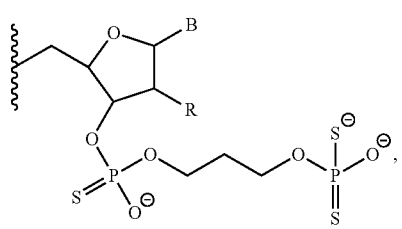

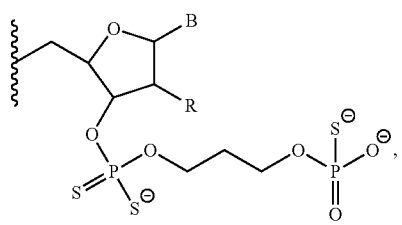

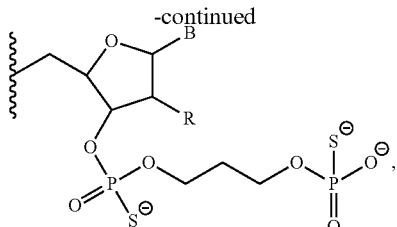

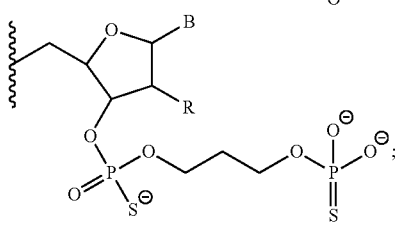

wherein B is a nucleotide base and R is H, OH or a 2' sugar modification.

10. The molecule of claim 1, wherein the non-nucleotide overhang is selected from the group consisting of C3Pi-C3OH, C3Pi-C3Pi, C3Pi-C3Ps, C3Ps-C3OH, C3Ps-C3Pi and C3Ps-C3Ps.

11. The molecule of claim 1, wherein the non-nucleotide overhang is selected from the group consisting of —C3Pi-C3Pi-C3OH, —C3Ps-C3Ps-C3OH, —C3Pi-C3Ps-C3OH, —C3Ps-C3Pi-C3OH, —C3Pi-C3Pi-C3Pi, —C3Ps-C3Ps-C3Ps, —C3Pi-C3Ps-C3Ps, —C3Ps-C3Pi-C3Ps, —C3Ps-C3Ps-C3Pi, —C3Pi-C3Pi-C3Ps, —C3Ps-C3Pi-C3Pi and —C3Pi-C3Ps-C3Pi.

12. The molecule of claim 1, wherein the non-nucleotide overhang is selected from the group consisting of —C3Pi-rAb, —C3Pi-dAb, —C3Ps-rAb and —C3Ps-dAb.

13. The molecule of claim 1, further comprising a non-nucleotide overhang covalently attached to the 3' terminal nucleotide in the sense strand, wherein the non-nucleotide overhang covalently attached to the 3' terminal nucleotide in the sense strand is selected from the group consisting of propanol, a C3 alkyl moiety linked to a phosphodiester and a C3 alkyl moiety linked to a phosphorothioate.

14. The molecule of claim 13, wherein the non-nucleotide overhang covalently attached to the 3' terminal nucleotide in the sense strand is propanol; and wherein the 3' terminal sugar residue has the following structure:

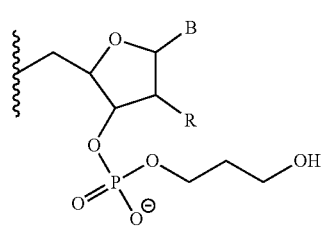

wherein B is a nucleotide base and R is H, OH or a 2' sugar modification.

15. The molecule of claim 13, wherein the non-nucleotide overhang covalently attached to the 3' terminal nucleotide in the sense strand is C3 alkyl moiety linked to a phosphodiester; and wherein the 3' terminal sugar residue has the following structure:

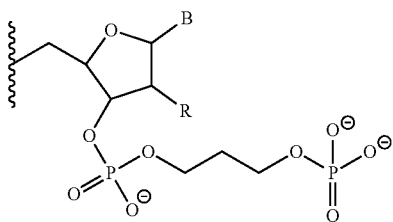

wherein B is a nucleotide base and R is H, OH or a 2' sugar modification.

16. The molecule of claim 13, wherein the non-nucleotide overhang covalently attached to the 3' terminal nucleotide in the antisense strand is selected from the group consisting of C3Pi-C3OH, C3Pi-C3Pi, C3Pi-C3Ps, C3Ps-C3OH, C3Ps-C3Pi and C3Ps-C3Ps; and wherein each Pi is a phosphodiester linkage and each Ps is a phosphorothioate linkage.

17. The molecule of claim 16, wherein the non-nucleotide overhang covalently attached to the 3' terminal nucleotide in the antisense strand is C3Pi-C3OH; and wherein the 3' terminal sugar residue has the following structure:

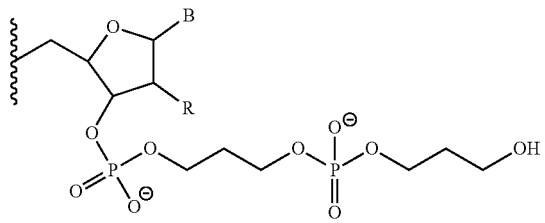

wherein B is a nucleotide base and R is H, OH or a 2' sugar modification.

18. The molecule of claim 16, wherein the non-nucleotide overhang covalently attached to the 3' terminal nucleotide in the antisense strand is C3Pi-C3Pi; and wherein the 3' terminal sugar residue has the following structure:

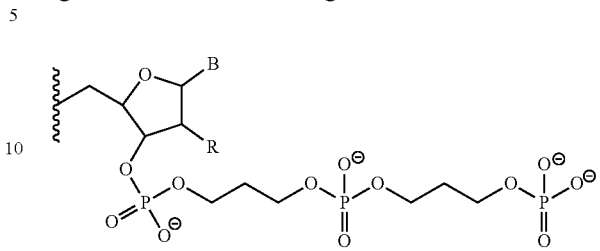

wherein B is a nucleotide base and R is H, OH or a 2' sugar modification.

19. The double stranded nucleic acid molecule of claim 2, wherein each of x and y is independently an integer between 18 and 27.

20. The double stranded nucleic acid molecule of claim 19, wherein x=y.

21. The double stranded nucleic acid molecule of claim 4, wherein Z' is a non-nucleotide overhang is selected from the group consisting of C3OH, C3Pi, C3Pi-C3OH, C3Pi-C3Pi, C3Pi-C3Ps, C3Ps, C3Ps-C3OH, C3Ps-C3Pi, C3Ps-C3Ps, C3Pi-C3Pi-C3OH, C3Ps-C3Ps-C3OH, C3Pi-C3Ps-C3OH, C3Ps-C3Pi-C3OH, C3Pi-C3Pi-C3Pi, C3Ps-C3Ps-C3Ps, C3Pi-C3Ps-C3Ps, C3Ps-C3Pi-C3Ps, C3Ps-C3Ps-C3Pi, C3Pi-C3Pi-C3Ps, C3Ps-C3Pi-C3Pi, C3Pi-C3Ps-C3Pi, C3Pi-rAb, C3Pi-dAb, C3Ps-rAb, C3Ps-dAb, rAbPi-C3OH, rAbPi-C3Pi, rAbPs-C3OH, rAbPs-C3Pi, dAbPi-C3OH, dAbPi-C3Pi, dAbPs-C3OH and dAbPs-C3Pi.

22. The double stranded nucleic acid molecule of claim 4, wherein Z' is an inorganic phosphate.

* * * * *

```
                              SEQUENCE LISTING

<160> NUMBER OF SEQ ID NOS: 28

<210> SEQ ID NO 1
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 1
gccagaaugu ggaacuccu                                                    19

<210> SEQ ID NO 2
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 2
aggaguucca cauucuggc                                                    19

<210> SEQ ID NO 3
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 3
gaaugugacu uccagacca                                                    19

<210> SEQ ID NO 4
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 4
uggucuggaa gucacauuc                                                    19

<210> SEQ ID NO 5
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 5
gaguccugca ucauuugaa                                                    19

<210> SEQ ID NO 6
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 6
uucaaaugau gcaggacuc                                                    19
```

```
<210> SEQ ID NO 7
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 7
ucgacagccc ugauaguuu                                                19

<210> SEQ ID NO 8
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 8
aaacuaucag ggcugucga                                                19

<210> SEQ ID NO 9
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 9
cagaagucau cuugcuaca                                                19

<210> SEQ ID NO 10
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 10
uguagcaaga ugacuucug                                                19

<210> SEQ ID NO 11
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 11
guggcagagu uacaguuca                                                19

<210> SEQ ID NO 12
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 12
ugaacuguaa cucugccac                                                19

<210> SEQ ID NO 13
<211> LENGTH: 19
<212> TYPE: RNA
<213> ORGANISM: ARTIFICIAL
<220> FEATURE:
```

<223> OTHER INFORMATION: Chemically Synhtesized

<400> SEQUENCE: 13
guggcagagu uacaguucu                                                      19

<210> SEQ ID NO 14
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 14
agaacuguaa cucugccac                                                      19

<210> SEQ ID NO 15
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 15
caucgacagc ccugauaga                                                      19

<210> SEQ ID NO 16
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 16
ucuaucaggg cugucgaug                                                      19

<210> SEQ ID NO 17
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 17
gaucuucgga augaugaga                                                      19

<210> SEQ ID NO 18
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 18
ucucaucauu ccgaagauc                                                      19

<210> SEQ ID NO 19
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 19
caucgacagc ccugauagu                                                      19

```
<210> SEQ ID NO 20
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 20
acuaucaggg cugucgaug                                                   19

<210> SEQ ID NO 21
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 21
ucgacagccc ugauaguua                                                   19

<210> SEQ ID NO 22
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 22
uaacuaucag ggcugucga                                                   19

<210> SEQ ID NO 23
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 23
gguggagaac cuuaugguc                                                   19

<210> SEQ ID NO 24
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 24
gaccauaagg uucuccacc                                                   19

<210> SEQ ID NO 25
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 25
agauaaugaa caccaagac                                                   19

<210> SEQ ID NO 26
<211> LENGTH: 19
<212> TYPE: RNA
<213> ORGANISM: ARTIFICIAL
<220> FEATURE:
<223> OTHER INFORMATION: Chemically Synhtesized
```

```
<400> SEQUENCE: 26
gucuuggugu ucauuaucu                                                    19

<210> SEQ ID NO 27
<211> LENGTH: 19
<212> TYPE: RNA
<213> ORGANISM: ARTIFICIAL
<220> FEATURE:
<223> OTHER INFORMATION: Chemically Synhtesized

<400> SEQUENCE: 27
gaauguggaa cuccucaac                                                    19

<210> SEQ ID NO 28
<211> LENGTH: 19
<212> TYPE: RNA
<213> ORGANISM: Artificial Sequence
<220> FEATURE:
<223> OTHER INFORMATION: Chemically Synhtesized

<400> SEQUENCE: 28
guugaggagu uccacauuc                                                    19
```